(12) United States Patent
Reigan et al.

(10) Patent No.: US 11,851,436 B2
(45) Date of Patent: Dec. 26, 2023

(54) FUSED BICYCLIC PYRIMIDINE DERIVATIVES AND USES THEREOF

(71) Applicant: The Regents of the University of Colorado, A Body Corporate, Denver, CO (US)

(72) Inventors: Philip Reigan, Castle Rock, CO (US); Kimberly A. Casalvieri, Arvada, CO (US)

(73) Assignee: THE REGENTS OF THE UNIVERSITY OF COLORADO, A BODY CORPORATE, Denver, CO (US)

( * ) Notice: Subject to any disclaimer, the term of this patent is extended or adjusted under 35 U.S.C. 154(b) by 0 days.

(21) Appl. No.: 17/831,469

(22) Filed: Jun. 3, 2022

(65) Prior Publication Data

US 2023/0029430 A1    Jan. 26, 2023

Related U.S. Application Data

(60) Provisional application No. 63/196,432, filed on Jun. 3, 2021.

(51) Int. Cl.
  *C07D 487/04* (2006.01)
  *A61P 35/00* (2006.01)

(52) U.S. Cl.
  CPC ............ *C07D 487/04* (2013.01); *A61P 35/00* (2018.01)

(58) Field of Classification Search
  CPC .............................. C07D 487/04; A61P 35/00
  See application file for complete search history.

(56) References Cited

FOREIGN PATENT DOCUMENTS

CN    103936742 A  *  1/2017  .......... C07D 473/32

OTHER PUBLICATIONS

Camille G. Wermuth, Molecular Variations Based on Isosteric Replacements, The Practice of Medicinal Chemistry, (1996), 203-237 (Year: 1996) (Year: 1996).*
Sulzmaier FJ, Ramos JW. RSK isoforms in cancer cell invasion and metastasis. Cancer Res. Oct. 13, 2013;73(20):6099-105. doi: 10.1158/0008-5472.CAN-13-1087. Epub Oct. 4, 2013. PMID: 24097826; PMCID: PMC3801100. (Year: 2013).*

* cited by examiner

*Primary Examiner* — Joseph R Kosack
*Assistant Examiner* — David M Shim
(74) *Attorney, Agent, or Firm* — Snell & Wilmer L.L.P.

(57) ABSTRACT

The present disclosure relates to a compound of Formula (0):

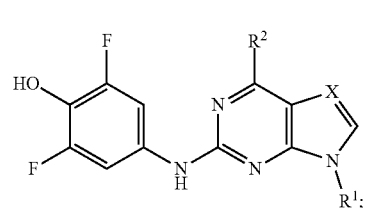

a stereoisomer thereof, a prodrug thereof, or a pharmaceutically acceptable salt thereof. The present disclosure also relates to uses of the compound.

18 Claims, 6 Drawing Sheets

BI-D1870

LJH685

LJI308

2,6-difluoro-4-(4-(4-(4-methylpiperazin-1-yl)phenyl)-1H-pyrrolo[2,3-c]pyridin-5-yl)phenol

FUSED BICYCLIC PYRIMIDINE DERIVATIVES AND USES THEREOF

CROSS-REFERENCE TO RELATED APPLICATIONS

This application claims priority to and the benefit of U.S. Provisional Application No. 63/196,432, filed Jun. 3, 2021, which is incorporated herein by reference in its entirety.

BACKGROUND

The 90-kDA ribosomal s6 kinases are a family of Ser/Thr protein kinases that are downstream effectors of the Ras/Raf/MEK/ERK signaling pathway. In humans, four RSK isoforms, RSK1, RSK2, RSK3 and RSK4, have been identified, along with two structurally related homologs known as mitogen- and stress-activated kinases 1 and 2 (MSK1/2). The RSKs phosphorylate a range of substrates involved in transcription, translation, cell cycle regulation and cell survival. The RSK1-4 isoforms are ubiquitously expressed in normal cell lines and tissues. Aberrant expression and/or activity of RSKs have been associated with several cancer types, including, but not limited to, breast cancer, colorectal cancer, head and neck squamous cell carcinoma (HNSCC), leukemia, lung cancer, malignant melanoma, multiple myeloma, acute myeloid leukemia, ovarian carcinoma and prostate cancer. More specifically, increased expression and activity of RSK1 and RSK2 in some cancer types has been linked to tumor growth and survival, indicating that RSK1 and RSK2 could be targeted by anticancer therapies. Conversely, RSK3 and RSK4 have been reported to act as tumor suppressors. However, current RSK inhibitors target more than one RSK isoform and show poor pharmacokinetic profiles, limiting their efficacy as anticancer agents. Accordingly, there is a need in the art for improved inhibitors of RSK proteins, including RSK2 inhibitors. The present disclosure addresses this need.

SUMMARY

In some aspects, the present disclosure provides a compound of Formula (0):

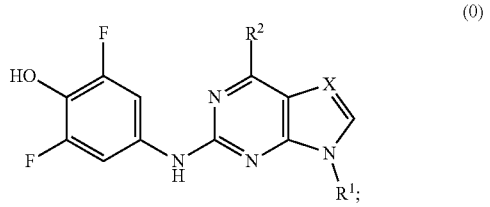

(0)

a stereoisomer thereof, a prodrug thereof, or a pharmaceutically acceptable salt thereof, wherein:
X is N or CH;
$R^1$ is H, $C_1$-$C_6$ alkyl, or $C_5$-$C_{10}$ aryl, wherein the $C_5$-$C_{10}$ aryl is optionally substituted with one or more $R^{1a}$;
each $R^{1a}$ independently is -$T^1$-$R^{1b}$;
each $T^1$ independently is absent, —O—*, —($C_1$-$C_6$ alkyl)-*, or —O—($C_1$-$C_6$ alkyl)-*, wherein * denotes attachment to $R^{1b}$;
each $R^{1b}$ independently is —OH, —C(=O)OH, —C(=O)O—($C_1$-$C_6$ alkyl), $C_5$-$C_{10}$ aryl, or 3- to 8-membered heterocycloalkyl, wherein the $C_5$-$C_{10}$ aryl or 3- to 8-membered heterocycloalkyl is optionally substituted with one or more OH or $C_1$-$C_6$ alkyl;
$R^2$ is H or 3- to 8-membered heterocycloalkyl optionally substituted with one or more $R^{2a}$;
each $R^{2a}$ independently is —$NH_2$, —NH(C=O)O—($C_1$-$C_6$ alkyl), —C(=O)OH, or —C(=O)NH—$R^{2b}$; or
each $R^{2b}$ independently is $C_1$-$C_6$ alkyl or —($C_1$-$C_6$ alkyl)-($C_5$-$C_{10}$ aryl), wherein the $C_1$-$C_6$ alkyl or —($C_1$-$C_6$ alkyl)-($C_5$-$C_{10}$ aryl) is optionally substituted with one or more halogen or OH.

In some embodiments, at most one of $R^1$ and $R^2$ is H.

In some aspects, the present disclosure provides a compound being an isotopic derivative (e.g., isotopically labeled compound) of any one of the compounds of the Formulae disclosed herein.

In some aspects, the present disclosure provides a method of preparing a compound disclosed herein.

In some aspects, the present disclosure provides a pharmaceutical composition comprising at least one compound of each of the formulae described herein, or a pharmaceutically acceptable salt or solvate thereof, and one or more pharmaceutically acceptable carriers or excipients.

In some aspects, the present disclosure provides a method for modulating RSK activity in a subject, the method comprising administering to the subject a therapeutically effective amount of at least one compound of the present disclosure, or a pharmaceutically acceptable salt thereof.

In some aspects, the present disclosure provides at least one compound of the present disclosure, or a pharmaceutically acceptable salt thereof, for use in modulating RSK activity in a subject.

In some aspects, the present disclosure provides the use of at least one compound of the present disclosure, or a pharmaceutically acceptable salt thereof, in the manufacture of a medicament for modulating RSK activity in a subject.

In some aspects, the present disclosure provides a method of treating or preventing cancer in a subject, the method comprising administering to the subject a therapeutically effective amount of at least one compound of the present disclosure, or a pharmaceutically acceptable salt thereof.

In some aspects, the present disclosure provides at least one compound of the present disclosure, or a pharmaceutically acceptable salt thereof, for use in the treatment or prevention of cancer in a subject.

In some aspects, the present disclosure provides the use of at least one compound of the present disclosure, or a pharmaceutically acceptable salt thereof, for the manufacture of a medicament for the treatment or prevention of cancer in a subject.

Unless otherwise defined, all technical and scientific terms used herein have the same meaning as commonly understood by one of ordinary skill in the art to which this disclosure belongs. In the specification, the singular forms also include the plural unless the context clearly dictates otherwise. Although methods and materials similar or equivalent to those described herein can be used in the practice or testing of the present disclosure, suitable methods and materials are described below. All publications, patent applications, patents and other references mentioned herein are incorporated by reference. The references cited herein are not admitted to be prior art to the claimed invention. In the case of conflict, the present specification, including definitions, will control. In addition, the materials, methods and examples are illustrative only and are not intended to be limiting. In the case of conflict between the chemical structures and names of the compounds disclosed herein, the chemical structures will control.

Other features and advantages of the disclosure will be apparent from the following detailed description and claims.

DETAILED DESCRIPTION

Figure 1:
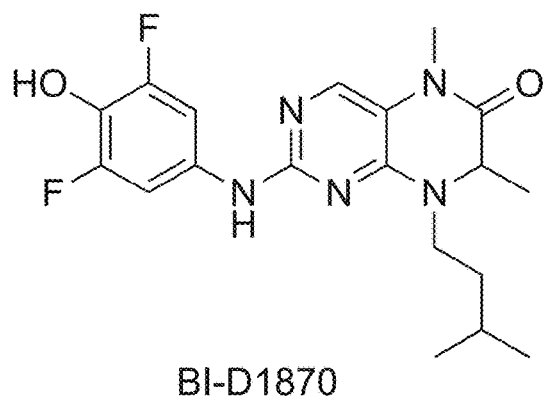
FIG. 1 is a graph showing chemical structures of several known RSK inhibitors: BI-D1870, LJH685, LJ1308, and azaindole 2,6-difluoro-4-(4-(4-(4-methylpiperazin-1-yl)phenyl)-1H-pyrrolo[2,3-c]pyridin-5-yl)phenol.
Figure 1:
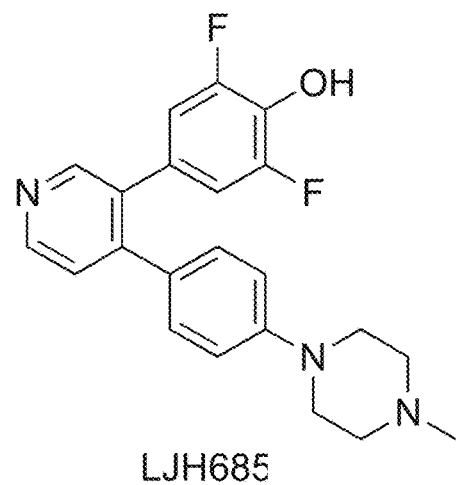
Figure 1:
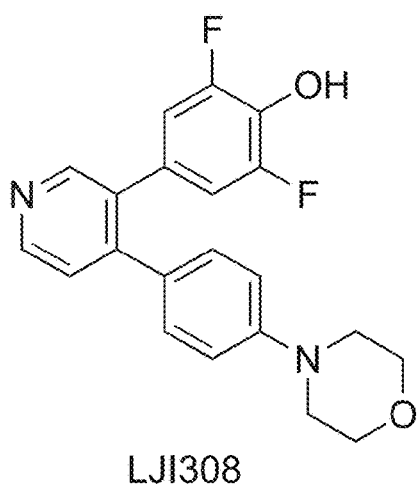
Figure 1:
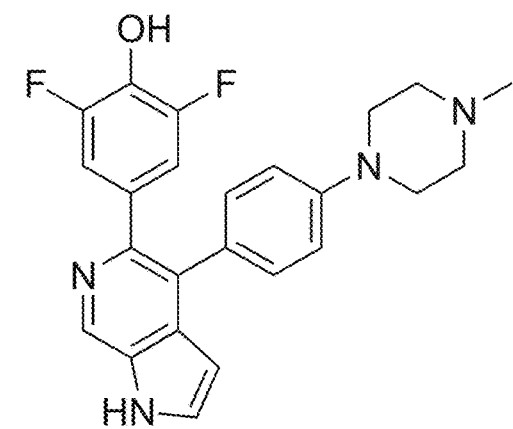

The p90 ribosomal S6 kinases are a family of highly conserved serine/threonine kinases that act as downstream effectors of the Ras/Raf/MEK/ERK signaling pathway. In humans, four RSK isoforms, RSK1, RSK2, RSK3 and RSK4, have been identified, along with two structurally related homologs known as mitogen- and stress-activated kinases 1 and 2 (MSK1/2).

RSK proteins comprise two functionally distinct kinase domains: an N-terminal kinase domain (NTKD) and a C-terminal kinase domain (CTKD). The NTKD and CTKD are connected by a regulatory linker domain. Activation of RSK proteins requires the sequential phosphorylation by ERK1/2 at the CTKD, autophosphorylation of the linker domain, and 3-phosphoinositide-dependent protein kinase 1 (PDK1)-mediated phosphorylation at the NTKD. More specifically, the CTKD of RSK proteins is involved in RSK autophosphorylation and is homologous to the calcium/calmodulin-dependent protein kinases (CaMKs), whereas the NTKD shares homology with the AGC kinase family and is responsible for RSK substrate phosphorylation. Although the four isoforms of the RSK family share a high degree of sequence homology (73-80% amino acid identity), particularly in the kinase domain (78-90%), there is increasing evidence of isoform specificity among the RSK isoforms in mediating distinct cellular processes.

Aberrant expression and/or activity of RSKs have been associated with several different types of cancer, including, but not limited to breast cancer, colorectal cancer, head and neck squamous cell carcinoma (HNSCC), leukemia, lung cancer, malignant melanoma, multiple myeloma, acute myeloid leukemia (AML), ovarian carcinoma and prostate cancer. More specifically, activity of RSK1 and/or RSK2 is hypothesized to promoter tumor growth and survival, while RSK3 and RSK4 are hypothesized to act as tumor suppressors through multiple cellular mechanisms. Accordingly, RSK proteins, and more specifically RSK1 and RSK2, have emerged as potential targets for anti-cancer therapy.

For example, RSK2 has been found to be aberrantly activated in acute myeloid leukemia (AML) cells. For example, RSK2 activity is required for the initiation and progression of FLT3/ITD-induced AML. Moreover, RSK2 has been reported to phosphorylate cAMP response-element binding protein (CREB), a nuclear transcription factor critical for hematopoietic cell proliferation, differentiation and survival. Approximately 60% of patients with AML express CREB at high levels and this is associated with increased risk of relapse and decreased survival. The phosphorylation of CREB by RSK2 promotes cell survival by increasing the transcription of Bcl-2, Bcl-cL and induced myeloid leukemia cell differentiation protein (MCL-1). Accordingly, without wishing to be bound by theory, targeting RSK2 using a small molecule inhibitor could be a potential therapeutic strategy for the treatment of AML.

Moreover, recent research has proposed that AMPK and/or MCL-1 may contribute to venetoclax resistance in AML cells (see Guiéze et al. *Cancel Cell*, 2019, 36(4): 369-384.e13, the contents of which are incorporated herein by reference in their entirety for all purposes). Without wishing to be bound by theory, given that RSK2 can modulate MCL-1 activity via GSK3 and its transcription via CREB (see Cook et al. *The FEBS Journal*, 2017, 284, 4177-4195, the contents of which are incorporated herein by reference in their entirety for all purposes), inhibition of RSK2 could be used to overcome venetoclax resistance in AML cells.

However, inhibition of RSK proteins for the treatment of cancer has been hampered by the fact that existing RSK inhibitors show little isoform specificity and act as pan-RSK inhibitors. Moreover, many existing RSK inhibitors exhibit poor pharmacokinetic profiles, further hampering their effectiveness in the clinic. For example, while BI-D1870 is remarkably selective for the RSKs as compared to other kinases, it has displayed high clarence and short plasma half-life in in vivo models, which has limited its evaluation in advanced preclinical in vivo cancer models. Thus, there is a need in the art for improved RSK inhibitors, including RSK2 inhibitors.

Compounds of the Present Disclosure

In some aspects, the present disclosure provides a compound of Formula (0):

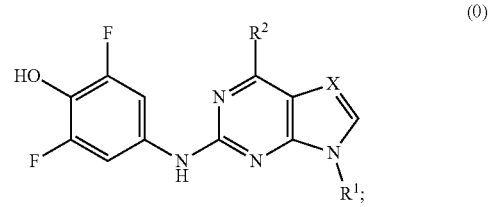

a stereoisomer thereof, a prodrug thereof, or a pharmaceutically acceptable salt thereof, wherein:
X is N or CH;
$R^1$ is H, $C_1$-$C_6$ alkyl, or $C_5$-$C_{10}$ aryl, wherein the $C_5$-$C_{10}$ aryl is optionally substituted with one or more $R^{1a}$;
each $R^{1a}$ independently is -$T^1$-$R^{1b}$;
each $T^1$ independently is absent, —O—*, —($C_1$-$C_6$ alkyl)-*, or —O—($C_1$-$C_6$ alkyl)-*, wherein * denotes attachment to $R^{1b}$;

each R$^{1b}$ independently is —OH, —C(=O)OH, —C(=O)O—(C$_1$-C$_6$ alkyl), C$_5$-C$_{10}$ aryl, or 3- to 8-membered heterocycloalkyl, wherein the C$_5$-C$_{10}$ aryl or 3- to 8-membered heterocycloalkyl is optionally substituted with one or more OH or C$_1$-C$_6$ alkyl;

R$^2$ is H or 3- to 8-membered heterocycloalkyl optionally substituted with one or more R$^{2a}$;

each R$^{2a}$ independently is —NH$_2$, —NH(C=O)O—(C$_1$-C$_6$ alkyl), —C(=O)OH, or —C(=O)NH—R$^{2b}$; or each R$^{2b}$ independently is C$_1$-C$_6$ alkyl or —(C$_1$-C$_6$ alkyl)-(C$_5$-C$_{10}$ aryl), wherein the C$_1$-C$_6$ alkyl or —(C$_1$-C$_6$ alkyl)-(C$_5$-C$_{10}$ aryl) is optionally substituted with one or more halogen or OH.

In some embodiments, at most one of R$^1$ and R$^2$ is H.

In some aspects, the present disclosure provides a compound of Formula (I):

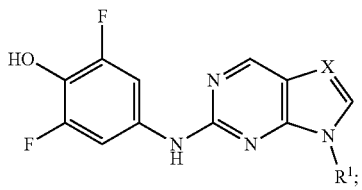

(I)

a stereoisomer thereof, a prodrug thereof, or a pharmaceutically acceptable salt thereof, wherein:

X is N or CH;

R$^1$ is H, C$_1$-C$_6$ alkyl, or C$_5$-C$_{10}$ aryl, wherein the C$_5$-C$_{10}$ aryl is optionally substituted with one or more R$^{1a}$;

each R$^{1a}$ independently is -T$^1$-R$^{1b}$;

each T$^1$ independently is absent, —O—*, —(C$_1$-C$_6$ alkyl)-*, or —O—(C$_1$-C$_6$ alkyl)-*, wherein * denotes attachment to R$^{1b}$; and each R$^{1b}$ independently is —OH, —C(=O)OH, —C(=O)O—(C$_1$-C$_6$ alkyl), C$_5$-C$_{10}$ aryl, or 3- to 8-membered heterocycloalkyl, wherein the C$_5$-C$_{10}$ aryl or 3- to 8-membered heterocycloalkyl is optionally substituted with one or more OH or C$_1$-C$_6$ alkyl.

In some aspects, the present disclosure provides a compound of Formula (II):

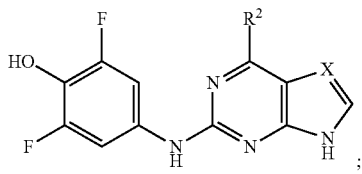

(II)

a stereoisomer thereof, a prodrug thereof, or a pharmaceutically acceptable salt thereof, wherein:

X is N or CH;

R$^2$ is H or 3- to 8-membered heterocycloalkyl optionally substituted with one or more R$^{2a}$;

each R$^{2a}$ independently is —NH$_2$, —NH(C=O)O—(C$_1$-C$_6$ alkyl), —C(=O)OH, or —C(=O)NH—R$^2$b; or each R$^{2b}$ independently is C$_1$-C$_6$ alkyl or —(C$_1$-C$_6$ alkyl)-(C$_5$-C$_{10}$ aryl), wherein the C$_1$-C$_6$ alkyl or —(C$_1$-C$_6$ alkyl)-(C$_5$-C$_{10}$ aryl) is optionally substituted with one or more halogen or OH.

It is understood that, for a compound of the present disclosure, variables X, R$^1$, R$^{1a}$, T$^1$, R$^{1b}$, R$^2$, R$^{2a}$, and R$^{2b}$ can each be, where applicable, selected from the groups described herein, and any group described herein for any of variables X, R$^1$, R$^{1a}$, T$^1$, R$^{1b}$, R$^2$, R$^{2a}$, and R$^{2b}$ can be combined, where applicable, with any group described herein for one or more of the remainder of variables X, R$^1$, R$^{1a}$, T$^1$, R$^{1b}$, R$^2$, R$^{2a}$, and R$^{2b}$.

Variables X R, R$^{1a}$, T$^1$, R$^{1b}$, R$^2$, R$^{2a}$, and R$^{2b}$.

In some embodiments, X is N.

In some embodiments, X is CH.

In some embodiments, R$^1$ is H.

In some embodiments, R$^1$ is C$_1$-C$_6$ alkyl, or C$_5$-C$_{10}$ aryl, wherein the C$_5$-C$_{10}$ aryl is optionally substituted with one or more R$^{1a}$.

In some embodiments, R$^1$ is C$_1$-C$_6$ alkyl.

In some embodiments, R$^1$ is methyl, ethyl, propyl, butyl, pentyl, or hexyl.

In some embodiments, R$^1$ is pentyl (e.g., 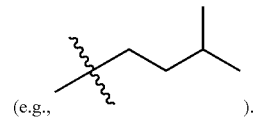 [SMILES: *CCC(C)C] ).

In some embodiments, R$^1$ is C$_5$-C$_{10}$ aryl optionally substituted with one or more R$^{1a}$.

In some embodiments, R$^1$ is phenyl optionally substituted with one or more R$^{1a}$.

In some embodiments, at least one T$^1$ independently absent.

In some embodiment, at least one R$^{1a}$ is R$^{1b}$.

In some embodiments, at least one R$^{1a}$ is —OH, —C(=O)OH, —C(=O)O—(C$_1$-C$_6$ alkyl), C$_5$-C$_{10}$ aryl, or 3- to 8-membered heterocycloalkyl, wherein the C$_5$-C$_{10}$ aryl or 3- to 8-membered heterocycloalkyl is optionally substituted with one or more OH or C$_1$-C$_6$ alkyl.

In some embodiments, at least one T$^1$ is —O—*, —(C$_1$-C$_6$ alkyl)-*, or —O—(C$_1$-C$_6$ alkyl)-*.

In some embodiments, at least one R$^{1a}$ is —O—R$^{1b}$, —(C$_1$-C$_6$ alkyl)-R$^{1b}$, or —O—(C$_1$-C$_6$ alkyl)-R$^{1b}$.

In some embodiments, at least one R$^{1b}$ is —OH, —C(=O)OH, or —C(=O)O—(C$_1$-C$_6$ alkyl).

In some embodiments, at least one R$^{1b}$ is —OH.

In some embodiments, at least one R$^{1b}$ is —C(=O)OH.

In some embodiments, at least one R$^{1b}$ is —C(=O)O—(C$_1$-C$_6$ alkyl).

In some embodiments, at least one R$^{1b}$ is C$_5$-C$_{10}$ aryl or 3- to 8-membered heterocycloalkyl, wherein the C$_5$-C$_{10}$ aryl or 3- to 8-membered heterocycloalkyl is optionally substituted with one or more OH or C$_1$-C$_6$ alkyl.

In some embodiments, at least one R$^{1b}$ is C$_5$-C$_{10}$ optionally substituted with one or more OH or C$_1$-C$_6$ alkyl.

In some embodiments, at least one R$^{1b}$ is phenyl optionally substituted with one or more OH or C$_1$-C$_6$ alkyl.

In some embodiments, at least one R$^{1b}$ is phenyl.

In some embodiments, at least one R$^{1b}$ is phenyl substituted with one or more OH.

In some embodiments, at least one R$^{1b}$ is 3- to 8-membered heterocycloalkyl optionally substituted with one or more OH or C$_1$-C$_6$ alkyl.

In some embodiments, at least one R$^{1b}$ is diazinanyl or morpholinyl, wherein the diazinanyl or morpholinyl is optionally substituted with one or more OH or C$_1$-C$_6$ alkyl.

In some embodiments, at least one R$^{1b}$ is diazinanyl or morpholinyl.

In some embodiments, at least one $R^{1b}$ is diazinanyl or morpholinyl, wherein the diazinanyl or morpholinyl is substituted with one or more $C_1$-$C_6$ alkyl.

In some embodiments, $R^2$ is H.

In some embodiments, $R^2$ is 3- to 8-membered heterocycloalkyl optionally substituted with one or more $R^{2a}$.

In some embodiments, $R^2$ is piperidinyl optionally substituted with one or more $R^{2a}$.

In some embodiments, $R^2$ is

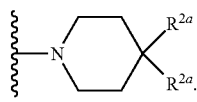

In some embodiments, at least one $R^{2a}$ is —$NH_2$ or —NH(C=O)O—($C_1$-$C_6$ alkyl).

In some embodiments, at least one $R^{2a}$ is —$NH_2$.

In some embodiments, $R^2$ is

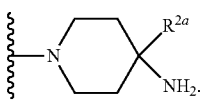

In some embodiments, at least one $R^{2a}$ is —NH(C=O)O—($C_1$-$C_6$ alkyl).

In some embodiments, at least one $R^{2a}$ is —C(=O)OH or —C(=O)NH—$R^{2b}$.

In some embodiments, at least one $R^{2a}$ is —C(=O)OH.

In some embodiments, at least one $R^{2a}$ is —C(=O)NH—$R^{2b}$.

In some embodiments, $R^2$ is

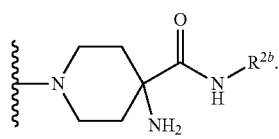

In some embodiments, at least one $R^{2b}$ is $C_1$-$C_6$ alkyl optionally substituted with one or more halogen or OH.

In some embodiments, at least one $R^{2b}$ is $C_1$-$C_6$ alkyl optionally substituted with one or more OH.

In some embodiments, at least one $R^{2b}$ is $C_1$-$C_6$ alkyl substituted with one or more OH.

In some embodiments, at least one $R^{2b}$ is

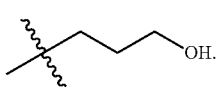 [SMILES: *CCCO]

In some embodiments, at least one $R^{2b}$ is —($C_1$-$C_6$ alkyl)-($C_5$-$C_{10}$ aryl) optionally substituted with one or more halogen or OH.

In some embodiments, at least one $R^{2b}$ is —($C_1$-$C_6$ alkyl)-phenyl optionally substituted with one or more halogen or OH.

In some embodiments, at least one $R^{2b}$ is

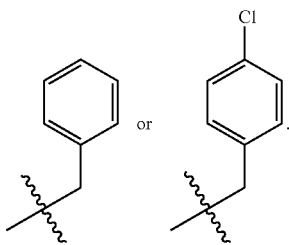 [SMILES: *Cc1ccccc1 ; *Cc1ccc(Cl)cc1]

In some embodiments, at least one $R^{2b}$ is

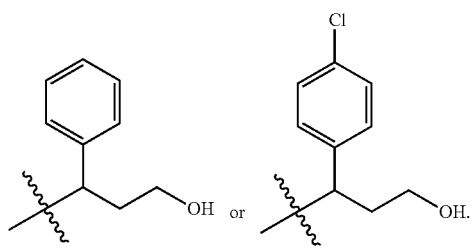 [SMILES: *C(CCO)c1ccccc1 ; *C(CCO)c1ccc(Cl)cc1 ; "or"]

In some embodiments, at least one $R^{2b}$ is

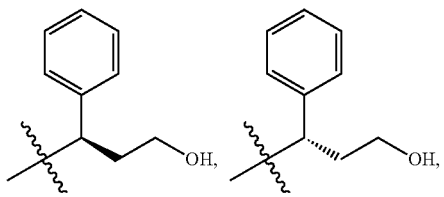

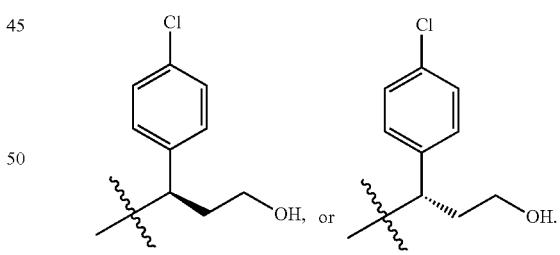

In some embodiments, $R^2$ is

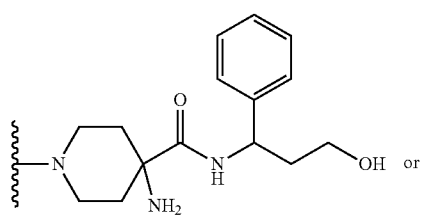

9

-continued

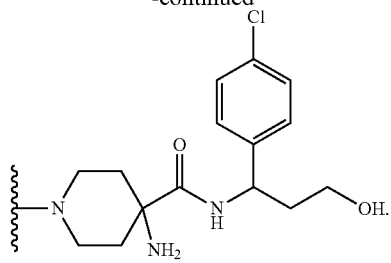

In some embodiments, $R^2$ is

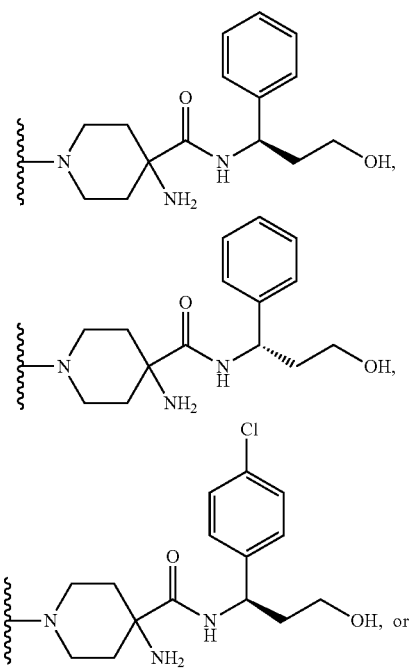

10

-continued

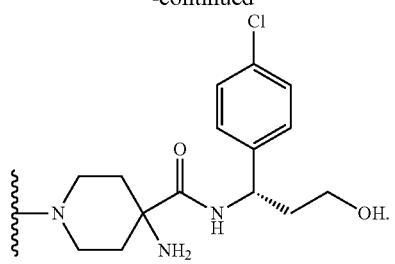

Exemplary Embodiments of the Compounds

In some embodiments, the compound is selected from the compounds described in Tables A1-A2, stereoisomers thereof, prodrugs thereof, and pharmaceutically acceptable salts thereof.

In some embodiments, the compound is selected from the compounds described in Table A1, stereoisomers thereof, prodrugs thereof, and pharmaceutically acceptable salts thereof.

In some embodiments, the compound is selected from the compounds described in Table A1 and pharmaceutically acceptable salts thereof.

In some embodiments, the compound is selected from the compounds described in Table A1.

In some embodiments, the compound is selected from the compounds described in Table A2, stereoisomers thereof, prodrugs thereof, and pharmaceutically acceptable salts thereof.

In some embodiments, the compound is selected from the compounds described in Table A2 and pharmaceutically acceptable salts thereof.

In some embodiments, the compound is selected from the compounds described in Table A2.

TABLE A1

| Compound No. | Structure |
|---|---|
| A1-1 | 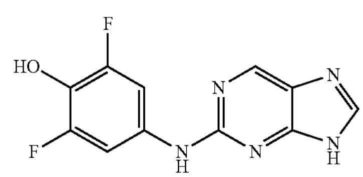 [SMILES: Oc1c(F)cc(Nc2ncc3nc[nH]c3n2)cc1F] |
| A1-2 | 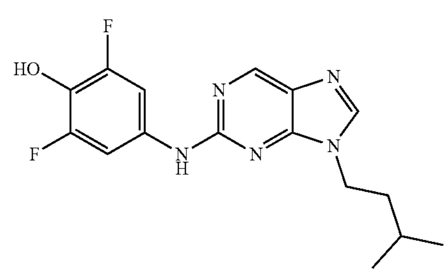 [SMILES: CC(C)CCn1cnc2cnc(Nc3cc(F)c(O)c(F)c3)nc21] |

TABLE A1-continued
| Compound No. | Structure |
|---|---|
| A1-3 | 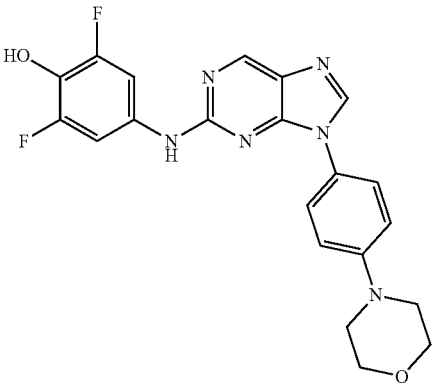 |
| A1-4 | 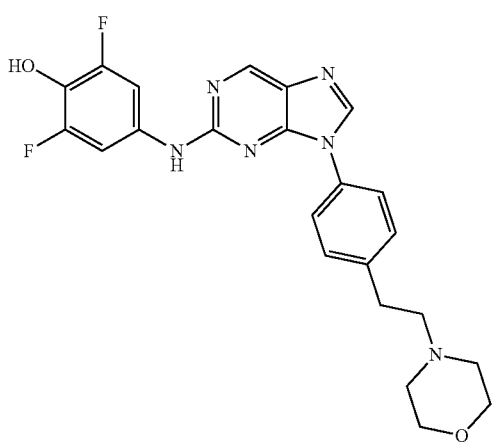 [SMILES: Oc1c(F)cc(Nc2ncc3ncn(-c4ccc(CCN5CCOCC5)cc4)c3n2)cc1F] |
| A1-5 | 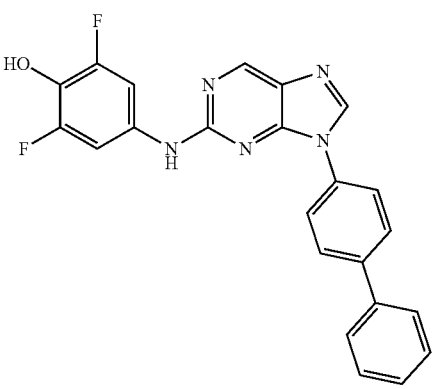 [SMILES: Oc1c(F)cc(Nc2ncc3ncn(-c4ccc(-c5ccccc5)cc4)c3n2)cc1F] |

TABLE A1-continued

| Compound No. | Structure |
|---|---|
| A1-6 | 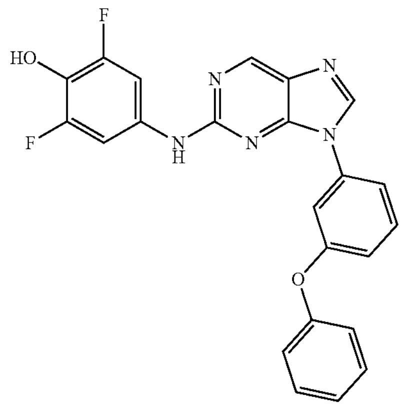 [SMILES: Oc1c(F)cc(Nc2ncc3ncn(-c4cccc(Oc5ccccc5)c4)c3n2)cc1F] |
| A1-7 | 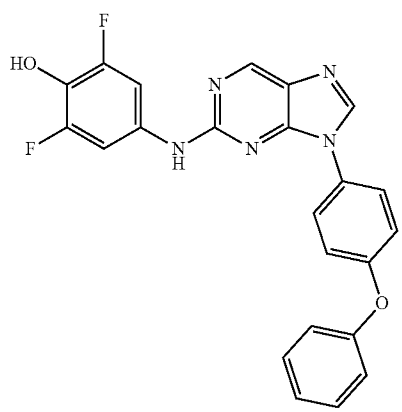 [SMILES: Oc1c(F)cc(Nc2ncc3ncn(-c4ccc(Oc5ccccc5)cc4)c3n2)cc1F] |
| A1-8 | 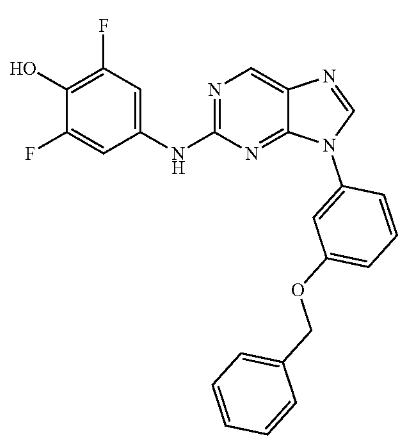 [SMILES: Oc1c(F)cc(Nc2ncc3ncn(-c4cccc(OCc5ccccc5)c4)c3n2)cc1F] |

TABLE A1-continued

| Compound No. | Structure |
| --- | --- |
| A1-9 | 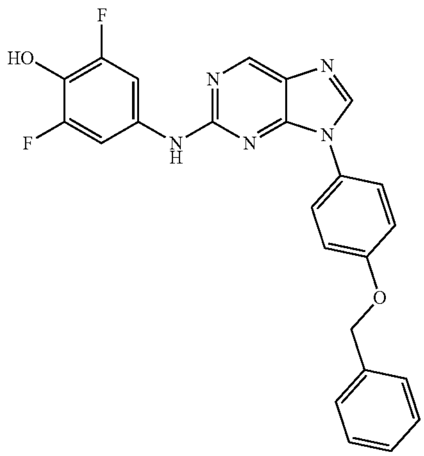 [SMILES: Oc1c(F)cc(Nc2ncc3ncn(-c4ccc(OCc5ccccc5)cc4)c3n2)cc1F] |
| A1-10 | 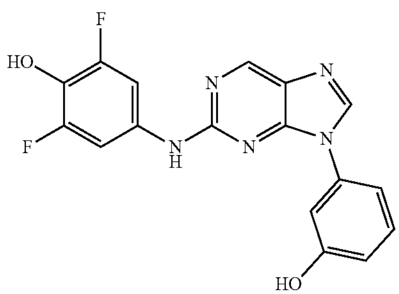 [SMILES: Oc1cccc(-n2cnc3cnc(Nc4cc(F)c(O)c(F)c4)nc32)c1] |
| A1-11 | 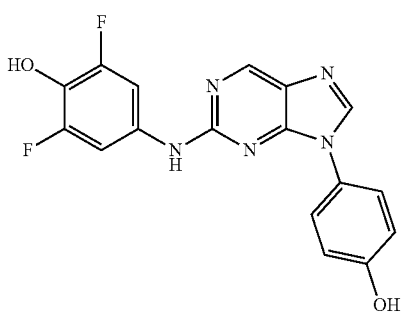 [SMILES: Oc1ccc(-n2cnc3cnc(Nc4cc(F)c(O)c(F)c4)nc32)cc1] |
| A1-12 | 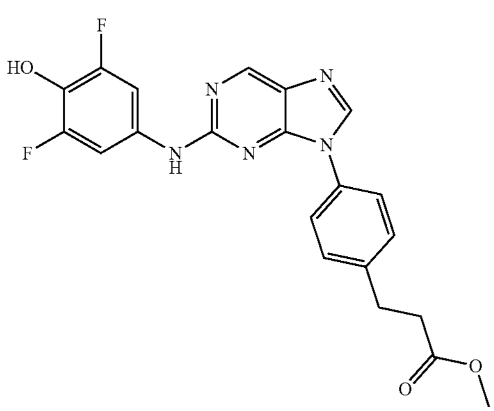 [SMILES: COC(=O)CCc1ccc(-n2cnc3cnc(Nc4cc(F)c(O)c(F)c4)nc32)cc1] |

TABLE A1-continued
| Compound No. | Structure |
|---|---|
| A1-13 | 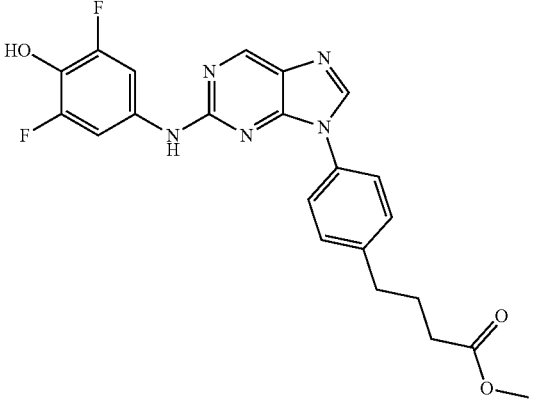 [SMILES: COC(=O)CCCc1ccc(-n2cnc3cnc(Nc4cc(F)c(O)c(F)c4)nc32)cc1] |
| A1-14 | 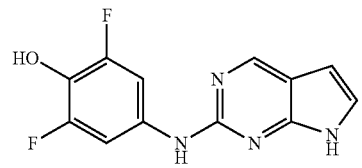 |
| A1-15 | 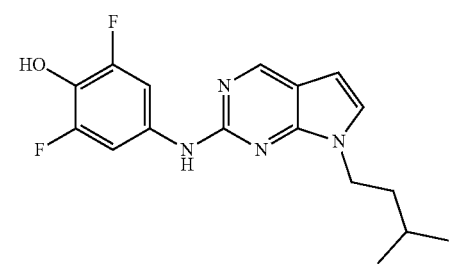 |
| A1-16 | 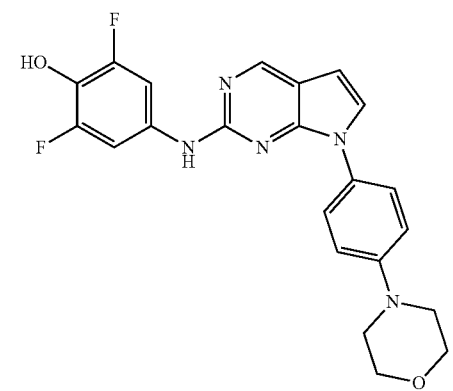 [SMILES: Oc1c(F)cc(Nc2ncc3ccn(-c4ccc(N5CCOCC5)cc4)c3n2)cc1F] |

TABLE A1-continued

| Compound No. | Structure |
|---|---|
| A1-17 | [Structure: 3,5-difluoro-4-hydroxyphenyl-NH-pyrrolopyrimidine with N-(4-(4-methylpiperazin-1-yl)phenyl) substituent] |

TABLE A2

| Compound No. | Structure |
|---|---|
| A2-1 | [Structure: piperidine-4-carboxamide with 4-amino and N-(3-hydroxy-1-(4-chlorophenyl)propyl), N-linked to pyrrolopyrimidine bearing 3,5-difluoro-4-hydroxyphenylamino] |
| A2-2 | [Structure: same as A2-1 with (S)-configuration at the benzylic carbon] |
| A2-3 | [Structure: same as A2-1 with (R)-configuration at the benzylic carbon] |

In some aspects, the present disclosure provides a compound which is an isotopic derivative (e.g., isotopically labeled compound) of any one of the compounds of the Formulae disclosed herein.

It is understood that the isotopic derivative can be prepared using any of a variety of art-recognized techniques. For example, the isotopic derivative can generally be prepared by carrying out the procedures disclosed in the Schemes and/or in the Examples herein, by substituting an isotopically labeled reagent for a non-isotopically labeled reagent.

In some embodiments, the isotopic derivative is a deuterium labeled compound.

In some embodiments, the isotopic derivative is a deuterium labeled compound of any one of the compounds of the Formulae disclosed herein.

The term "isotopic derivative", as used herein, refers to a derivative of a compound in which one or more atoms are isotopically enriched or labelled. For example, an isotopic derivative of a compound is isotopically enriched with regard to, or labelled with, one or more isotopes as compared to the corresponding compound. In some embodiments, the compound is a $^2$H labeled compound. In some embodiments, the compound is a $^{13}$C labeled compound or a $^{14}$C labeled compound. In some embodiments, the compound is a $^{18}$F labeled compound.

It is understood that the isotopic derivatives can be prepared using any of a variety of art-recognized techniques. For example, the isotopic derivatives can generally be prepared by carrying out the procedures disclosed in the Schemes and/or in the Examples described herein, by substituting an isotope labeled reagent for a non-isotope labeled reagent.

It is also understood that isotopical substitution may afford certain therapeutic advantages resulting from greater metabolic stability, e.g., increased in vivo half-life or reduced dosage requirements.

It is to be understood that the compounds of any one of the Formulae disclosed herein and any pharmaceutically acceptable salts thereof, comprise stereoisomers, mixtures of stereoisomers, polymorphs of all isomeric forms of said compounds.

It is to be understood that while compounds disclosed herein may be presented in one particular configuration. Such particular configuration is not to be construed as limiting the disclosure to one or another isomer, tautomer, regioisomer or stereoisomer, nor does it exclude mixtures of isomers, tautomers, regioisomers or stereoisomers. In some embodiments, the presentation of a compound herein in a particular configuration intends to encompass, and to refer to, each of the available isomers, tautomers, regioisomers, and stereoisomers of the compound, or any mixture thereof, while the presentation further intends to refer to the specific configuration of the compound.

It is to be understood that while compounds disclosed herein may be presented without specified configuration (e.g., without specified stereochemistry). Such presentation intends to encompass all available isomers, tautomers, regioisomers, and stereoisomers of the compound.

In some embodiments, the presentation of a compound herein without specified configuration intends to refer to each of the available isomers, tautomers, regioisomers, and stereoisomers of the compound, or any mixture thereof.

As used herein, the term "isomerism" means compounds that have identical molecular formulae but differ in the sequence of bonding of their atoms or in the arrangement of their atoms in space. Isomers that differ in the arrangement of their atoms in space are termed "stereoisomers." Stereoisomers that are not mirror images of one another are termed "diastereoisomers," and stereoisomers that are non-superimposable mirror images of each other are termed "enantiomers" or sometimes optical isomers. A mixture containing equal amounts of individual enantiomeric forms of opposite chirality is termed a "racemic mixture."

As used herein, the term "chiral centre" refers to a carbon atom bonded to four nonidentical substituents.

As used herein, the term "chiral isomer" means a compound with at least one chiral centre. Compounds with more than one chiral centre may exist either as an individual diastereomer or as a mixture of diastereomers, termed "diastereomeric mixture." When one chiral centre is present, a stereoisomer may be characterised by the absolute configuration (R or S) of that chiral centre. Absolute configuration refers to the arrangement in space of the substituents attached to the chiral centre. The substituents attached to the chiral centre under consideration are ranked in accordance with the Sequence Rule of Cahn, Ingold and Prelog. (Cahn et al., *Angew. Chem. Inter. Edit.* 1966, 5, 385; errata 511; Cahn et al., *Angew. Chem.* 1966, 78, 413; Cahn and Ingold, *J. Chem. Soc.* 1951 (London), 612; Cahn et al., *Experientia* 1956, 12, 81; Cahn, *J. Chem. Educ.* 1964, 41, 116).

As used herein, the term "geometric isomer" means the diastereomers that owe their existence to hindered rotation about double bonds or a cycloalkyl linker (e.g., 1,3-cyclobutyl). These configurations are differentiated in their names by the prefixes cis and trans, or Z and E, which indicate that the groups are on the same or opposite side of the double bond in the molecule according to the Cahn-Ingold-Prelog rules.

It is to be understood that the compounds of the present disclosure may be depicted as different chiral isomers or geometric isomers. It is also to be understood that when compounds have chiral isomeric or geometric isomeric forms, all isomeric forms are intended to be included in the scope of the present disclosure, and the naming of the compounds does not exclude any isomeric forms, it being understood that not all isomers may have the same level of activity.

It is to be understood that the structures and other compounds discussed in this disclosure include all atropic isomers thereof. It is also to be understood that not all atropic isomers may have the same level of activity.

As used herein, the term "atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

As used herein, the term "tautomer" is one of two or more structural isomers that exist in equilibrium and is readily converted from one isomeric form to another. This conversion results in the formal migration of a hydrogen atom accompanied by a switch of adjacent conjugated double bonds. Tautomers exist as a mixture of a tautomeric set in solution. In solutions where tautomerisation is possible, a chemical equilibrium of the tautomers will be reached. The exact ratio of the tautomers depends on several factors, including temperature, solvent and pH. The concept of tautomers that are interconvertible by tautomerisations is called tautomerism. Of the various types of tautomerism that are possible, two are commonly observed. In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose.

It is to be understood that the compounds of the present disclosure may be depicted as different tautomers. It should also be understood that when compounds have tautomeric forms, all tautomeric forms are intended to be included in the scope of the present disclosure, and the naming of the compounds does not exclude any tautomer form. It will be understood that certain tautomers may have a higher level of activity than others.

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric centre, for example, it is bonded to four different groups, a pair of enantiomers is possible. An enantiomer can be characterised by the absolute configuration of its asymmetric centre and is described by the R- and S-sequencing rules of Cahn and Prelog, or by the manner in which the molecule rotates the plane of polarised light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of this disclosure may possess one or more asymmetric centres; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 2001), for example by synthesis from optically active starting materials or by resolution of a racemic form. Some of the compounds of the disclosure may have geometric isomeric centres (E- and Z-isomers). It is to be understood that the present disclosure encompasses all optical, diastereoisomers and geometric isomers and mixtures thereof that possess inflammasome inhibitory activity.

The present disclosure also encompasses compounds of the disclosure as defined herein which comprise one or more isotopic substitutions.

It is to be understood that the compounds of any Formula described herein include the compounds themselves, as well as their salts, and their solvates, if applicable. A salt, for example, can be formed between an anion and a positively charged group (e.g., amino) on a substituted compound disclosed herein. Suitable anions include chloride, bromide, iodide, sulfate, bisulfate, sulfamate, nitrate, phosphate, citrate, methanesulfonate, trifluoroacetate, glutamate, glucuronate, glutarate, malate, maleate, succinate, fumarate, tartrate, tosylate, salicylate, lactate, naphthalenesulfonate, and acetate (e.g., trifluoroacetate).

As used herein, the term "pharmaceutically acceptable anion" refers to an anion suitable for forming a pharmaceutically acceptable salt. Likewise, a salt can also be formed between a cation and a negatively charged group (e.g., carboxylate) on a substituted compound disclosed herein. Suitable cations include sodium ion, potassium ion, magnesium ion, calcium ion, and an ammonium cation such as tetramethylammonium ion or diethylamine ion. The substituted compounds disclosed herein also include those salts containing quaternary nitrogen atoms.

It is to be understood that the compounds of the present disclosure, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

As used herein, the term "solvate" means solvent addition forms that contain either stoichiometric or non-stoichiometric amounts of solvent. Some compounds have a tendency to trap a fixed molar ratio of solvent molecules in the crystalline solid state, thus forming a solvate. If the solvent is water the solvate formed is a hydrate; and if the solvent is alcohol, the solvate formed is an alcoholate. Hydrates are formed by the combination of one or more molecules of water with one molecule of the substance in which the water retains its molecular state as $H_2O$.

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar or comparable in function and appearance, but not in structure origin to the reference compound.

As used herein, the term "derivative" refers to compounds that have a common core structure and are substituted with various groups as described herein.

As used herein, the term "bioisostere" refers to a compound resulting from the exchange of an atom or of a group of atoms with another, broadly similar, atom or group of atoms. The objective of a bioisosteric replacement is to create a new compound with similar biological properties to the parent compound. The bioisosteric replacement may be physicochemically or topologically based. Examples of carboxylic acid bioisosteres include, but are not limited to, acyl sulfonamides, tetrazoles, sulfonates and phosphonates. See, e.g., Patani and LaVoie, *Chem. Rev.* 96, 3147-3176, 1996.

It is also to be understood that certain compounds of any one of the Formulae disclosed herein may exist in solvated as well as unsolvated forms such as, for example, hydrated forms. A suitable pharmaceutically acceptable solvate is, for example, a hydrate such as hemi-hydrate, a mono-hydrate, a di-hydrate or a tri-hydrate. It is to be understood that the disclosure encompasses all such solvated forms that possess inflammasome inhibitory activity.

It is also to be understood that certain compounds of any one of the Formulae disclosed herein may exhibit polymorphism, and that the disclosure encompasses all such forms, or mixtures thereof, which possess inflammasome inhibitory activity. It is generally known that crystalline materials may be analysed using conventional techniques such as X-Ray Powder Diffraction analysis, Differential Scanning Calorimetry, Thermal Gravimetric Analysis, Diffuse Reflectance Infrared Fourier Transform (DRIFT) spectroscopy, Near Infrared (NIR) spectroscopy, solution and/or solid state nuclear magnetic resonance spectroscopy. The water content of such crystalline materials may be determined by Karl Fischer analysis.

Compounds of any one of the Formulae disclosed herein may exist in a number of different tautomeric forms and references to the compounds include all such forms. For the avoidance of doubt, where a compound can exist in one of several tautomeric forms, and only one is specifically described or shown, all others are nevertheless embraced. Examples of tautomeric forms include keto-, enol-, and enolate-forms, as in, for example, the following tautomeric pairs: keto/enol (illustrated below), imine/enamine, amide/imino alcohol, amidine/amidine, nitroso/oxime, thioketone/enethiol, and nitro/aci-nitro.

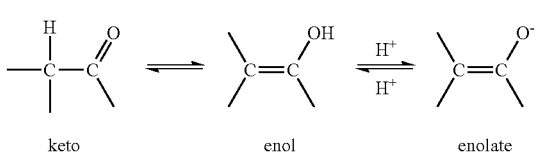

Compounds of any one of the Formulae disclosed herein containing an amine function may also form N-oxides. A reference herein to a compound that contains an amine function also includes the N-oxide. Where a compound contains several amine functions, one or more than one nitrogen atom may be oxidised to form an N-oxide. Particular examples of N-oxides are the N-oxides of a tertiary amine or a nitrogen atom of a nitrogen-containing heterocycle. N-oxides can be formed by treatment of the corresponding amine with an oxidising agent such as hydrogen peroxide or a peracid (e.g. a peroxycarboxylic acid), see for example Advanced Organic Chemistry, by Jerry March, 4th Edition, Wiley Interscience, pages. More particularly, N-oxides can be made by the procedure of L. W. Deady (Syn. Comm. 1977, 7, 509-514) in which the amine compound is reacted with meta-chloroperoxybenzoic acid (mCPBA), for example, in an inert solvent such as dichloromethane.

The compounds of any one of the Formulae disclosed herein may be administered in the form of a prodrug which is broken down in the human or animal body to release a compound of the disclosure. A prodrug may be used to alter the physical properties and/or the pharmacokinetic properties of a compound of the disclosure. A prodrug can be formed when the compound of the disclosure contains a suitable group or substituent to which a property-modifying group can be attached. Examples of prodrugs include derivatives containing in vivo cleavable alkyl or acyl substitutents at the ester or amide group in any one of the Formulae disclosed herein.

Accordingly, the present disclosure includes those compounds of any one of the Formulae disclosed herein as defined hereinbefore when made available by organic synthesis and when made available within the human or animal body by way of cleavage of a prodrug thereof. Accordingly, the present disclosure includes those compounds of any one of the Formulae disclosed herein that are produced by organic synthetic means and also such compounds that are produced in the human or animal body by way of metabolism of a precursor compound, that is a compound of any one of the Formulae disclosed herein may be a synthetically-produced compound or a metabolically-produced compound.

A suitable pharmaceutically acceptable prodrug of a compound of any one of the Formulae disclosed herein is one that is based on reasonable medical judgment as being suitable for administration to the human or animal body without undesirable pharmacological activities and without undue toxicity. Various forms of prodrug have been described, for example in the following documents: a) Methods in Enzymology, Vol. 42, p. 309-396, edited by K. Widder, et al. (Academic Press, 1985); b) Design of Prodrugs, edited by H. Bundgaard, (Elsevier, 1985); c) A Textbook of Drug Design and Development, edited by Krogsgaard-Larsen and H. Bundgaard, Chapter 5 "Design and Application of Pro-drugs", by H. Bundgaard p. 113-191 (1991); d) H. Bundgaard, Advanced Drug Delivery Reviews, 8, 1-38 (1992); e) H. Bundgaard, et al., Journal of Pharmaceutical Sciences, 77, 285 (1988); f) N. Kakeya, et al., Chem. Pharm. Bull., 32, 692 (1984); g) T. Higuchi and V. Stella, "Pro-Drugs as Novel Delivery Systems", A.C.S. Symposium Series, Volume 14; and h) E. Roche (editor), "Bioreversible Carriers in Drug Design", Pergamon Press, 1987.

A suitable pharmaceutically acceptable prodrug of a compound of any one of the Formulae disclosed herein that possesses a hydroxy group is, for example, an in vivo cleavable ester or ether thereof. An in vivo cleavable ester or ether of a compound of any one of the Formulae disclosed herein containing a hydroxy group is, for example, a pharmaceutically acceptable ester or ether which is cleaved in the human or animal body to produce the parent hydroxy compound. Suitable pharmaceutically acceptable ester forming groups for a hydroxy group include inorganic esters such as phosphate esters (including phosphoramidic cyclic esters). Further suitable pharmaceutically acceptable ester forming groups for a hydroxy group include $C_1$-$C_{10}$ alkanoyl groups such as acetyl, benzoyl, phenylacetyl and substituted benzoyl and phenylacetyl groups, $C_1$-$C_{10}$ alkoxycarbonyl groups such as ethoxycarbonyl, N,N—($C_1$-$C_6$ alkyl)$_2$carbamoyl, 2-dialkylaminoacetyl and 2-carboxyacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-($C_1$-$C_4$ alkyl)piperazin-1-ylmethyl. Suitable pharmaceutically acceptable ether forming groups for a hydroxy group include α-acyloxyalkyl groups such as acetoxymethyl and pivaloyloxymethyl groups.

A suitable pharmaceutically acceptable prodrug of a compound of any one of the Formulae disclosed herein that possesses a carboxy group is, for example, an in vivo cleavable amide thereof, for example an amide formed with an amine such as ammonia, a $C_{1-4}$alkylamine such as methylamine, a ($C_1$-$C_4$ alkyl)$_2$amine such as dimethylamine, N-ethyl-N-methylamine or diethylamine, a $C_1$-$C_4$ alkoxy-$C_2$-$C_4$ alkylamine such as 2-methoxyethylamine, a phenyl-$C_1$-$C_4$ alkylamine such as benzylamine and amino acids such as glycine or an ester thereof.

A suitable pharmaceutically acceptable prodrug of a compound of any one of the Formulae disclosed herein that possesses an amino group is, for example, an in vivo cleavable amide derivative thereof. Suitable pharmaceutically acceptable amides from an amino group include, for example an amide formed with $C_1$-$C_{10}$ alkanoyl groups such as an acetyl, benzoyl, phenylacetyl and substituted benzoyl and phenylacetyl groups. Examples of ring substituents on the phenylacetyl and benzoyl groups include aminomethyl, N-alkylaminomethyl, N,N-dialkylaminomethyl,morpholinomethyl,piperazin-1-ylmethyl and 4-($C_1$-$C_4$ alkyl)piperazin-1-ylmethyl.

The in vivo effects of a compound of any one of the Formulae disclosed herein may be exerted in part by one or more metabolites that are formed within the human or animal body after administration of a compound of any one of the Formulae disclosed herein. As stated hereinbefore, the in vivo effects of a compound of any one of the Formulae disclosed herein may also be exerted by way of metabolism of a precursor compound (a prodrug).

Suitably, the present disclosure excludes any individual compounds not possessing the biological activity defined herein.

Synthesis of the Compounds

In some aspects, the present disclosure provides a method of preparing a compound of the present disclosure.

In some aspects, the present disclosure provides a method of preparing a compound, comprising one or more steps as described herein.

In some aspects, the present disclosure provides a compound obtainable by, or obtained by, a method for preparing a compound as described herein.

In some aspects, the present disclosure provides an intermediate as described herein, being suitable for use in a method for preparing a compound as described herein.

The compounds of the present disclosure can be prepared by any suitable technique known in the art. Particular processes for the preparation of these compounds are described further in the accompanying examples.

In the description of the synthetic methods described herein and in any referenced synthetic methods that are used to prepare the starting materials, it is to be understood that all proposed reaction conditions, including choice of solvent, reaction atmosphere, reaction temperature, duration of the experiment and workup procedures, can be selected by a person skilled in the art.

It is understood by one skilled in the art of organic synthesis that the functionality present on various portions of the molecule must be compatible with the reagents and reaction conditions utilized.

It will be appreciated that during the synthesis of the compounds of the disclosure in the processes defined herein, or during the synthesis of certain starting materials, it may be desirable to protect certain substituent groups to prevent their undesired reaction. The skilled chemist will appreciate when such protection is required, and how such protecting groups may be put in place, and later removed. For examples of protecting groups see one of the many general texts on the subject, for example, 'Protective Groups in Organic Synthesis' by Theodora Green (publisher: John Wiley & Sons). Protecting groups may be removed by any convenient method described in the literature or known to the skilled chemist as appropriate for the removal of the protecting group in question, such methods being chosen so as to effect removal of the protecting group with the minimum disturbance of groups elsewhere in the molecule. Thus, if reactants include, for example, groups such as amino, carboxy or hydroxy it may be desirable to protect the group in some of the reactions mentioned herein.

By way of example, a suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed by, for example, hydrolysis with a suitable base such as an alkali metal hydroxide, for example lithium or sodium hydroxide. Alternatively an acyl group such as a tert-butoxycarbonyl group may be removed, for example, by treatment with a suitable acid as hydrochloric, sulphuric or phosphoric acid or trifluoroacetic acid and an arylmethoxycarbonyl group such as a benzyloxycarbonyl group may be removed, for example, by hydrogenation over a catalyst such as palladium on carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium, sodium hydroxide or ammonia. Alternatively an arylmethyl group such as a benzyl group may be removed, for example, by hydrogenation over a catalyst such as palladium on carbon.

A suitable protecting group for a carboxy group is, for example, an esterifying group, for example a methyl or an ethyl group which may be removed, for example, by hydrolysis with a base such as sodium hydroxide, or for example a tert-butyl group which may be removed, for example, by treatment with an acid, for example an organic acid such as trifluoroacetic acid, or for example a benzyl group which may be removed, for example, by hydrogenation over a catalyst such as palladium on carbon.

The resultant compounds can be isolated and purified using techniques well known in the art.

Conveniently, the reaction of the compounds is carried out in the presence of a suitable solvent, which is preferably inert under the respective reaction conditions. Examples of suitable solvents comprise but are not limited to hydrocarbons, such as hexane, petroleum ether, benzene, toluene or xylene; chlorinated hydrocarbons, such as trichlorethylene, 1,2-dichloroethane, tetrachloromethane, chloroform or dichloromethane; alcohols, such as methanol, ethanol, isopropanol, n-propanol, n-butanol or tert-butanol; ethers, such as diethyl ether, diisopropyl ether, tetrahydrofuran (THF), 2-methyltetrahydrofuran, cyclopentylmethyl ether (CPME), methyl tert-butyl ether (MTBE) or dioxane; glycol ethers, such as ethylene glycol monomethyl or monoethyl ether or ethylene glycol dimethyl ether (diglyme); ketones, such as acetone, methylisobutylketone (MIBK) or butanone; amides, such as acetamide, dimethylacetamide, dimethylformamide (DMF) or N-methylpyrrolidinone (NMP); nitriles, such as acetonitrile; sulphoxides, such as dimethyl sulphoxide (DMSO); nitro compounds, such as nitromethane or nitrobenzene; esters, such as ethyl acetate or methyl acetate, or mixtures of the said solvents or mixtures with water.

The reaction temperature is suitably between about $-100°$ C. and 300° C., depending on the reaction step and the conditions used.

Reaction times are generally in the range between a fraction of a minute and several days, depending on the reactivity of the respective compounds and the respective reaction conditions. Suitable reaction times are readily determinable by methods known in the art, for example reaction monitoring. Based on the reaction temperatures given above, suitable reaction times generally lie in the range between 10 minutes and 48 hours.

Moreover, by using the procedures described herein, in conjunction with ordinary skills in the art, additional compounds of the present disclosure can be readily prepared. Those skilled in the art will readily understand that known variations of the conditions and processes of the following preparative procedures can be used to prepare these compounds.

As will be understood by the person skilled in the art of organic synthesis, compounds of the present disclosure are readily accessible by various synthetic routes, some of which are exemplified in the accompanying examples. The skilled person will easily recognize which kind of reagents and reactions conditions are to be used and how they are to be applied and adapted in any particular instance—wherever necessary or useful—in order to obtain the compounds of the present disclosure. Furthermore, some of the compounds of the present disclosure can readily be synthesized by reacting other compounds of the present disclosure under suitable conditions, for instance, by converting one particular functional group being present in a compound of the present disclosure, or a suitable precursor molecule thereof, into another one by applying standard synthetic methods, like reduction, oxidation, addition or substitution reactions; those methods are well known to the skilled person. Likewise, the skilled person will apply—whenever necessary or useful—synthetic protecting (or protective) groups; suitable protecting groups as well as methods for introducing and removing them are well-known to the person skilled in the art of chemical synthesis and are described, in more detail, in, e.g., P.G.M. Wuts, T. W. Greene, "Greene's Protective Groups in Organic Synthesis", 4th edition (2006) (John Wiley & Sons).

General routes for the synthesis of the compound of the present disclosure are described in Schemes 1-2 below.

Scheme 1

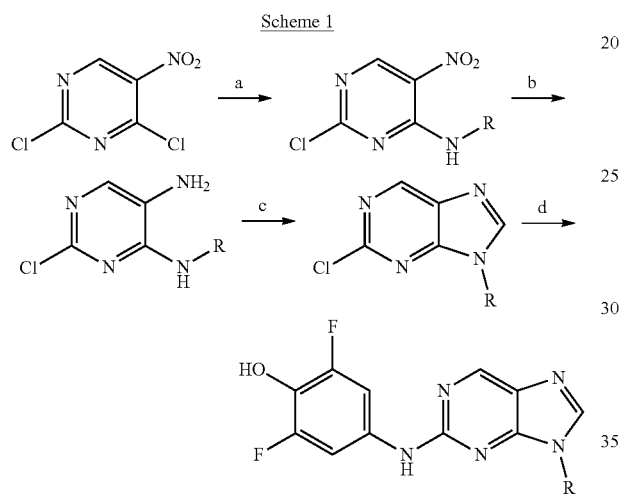

Reagents and Conditions: (a) aniline, DCM, −15° C., 10 min; (b) SnCl$_2$, EtOH, reflux, 2 h; (c) triethyl orthoformate, TFA, TFE, MW, 140° C., 1.5 h; (d) 4-amino-2,6-difluorophenol, TFA, TFE, MW, 140° C., 1.5 h.

In general, the purine compound was generated by first treating 2,4-dichloro-5-nitropyrimidine with the necessary aniline in order to selectively couple the aniline at the 4-position of the pyrimidine. The nitropyrimidine was then reduced to diamine (e.g., using tin(II) chloride), which were subsequently reacted with triethyl orthoformate (e.g., under microwave irradiation) to yield purine. 4-Amino-2,6-difluorophenol was coupled to the purine (e.g., using a trifluoroacetic acid (TFA) and trifluoroethanol-mediated SNAr reaction) to generate the final compound. Additionally, the purine may undergo a deprotection (e.g., a subsequent Pd-mediated benzyl deprotection) to generate its phenol analog.

Scheme 2

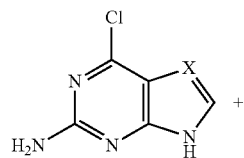

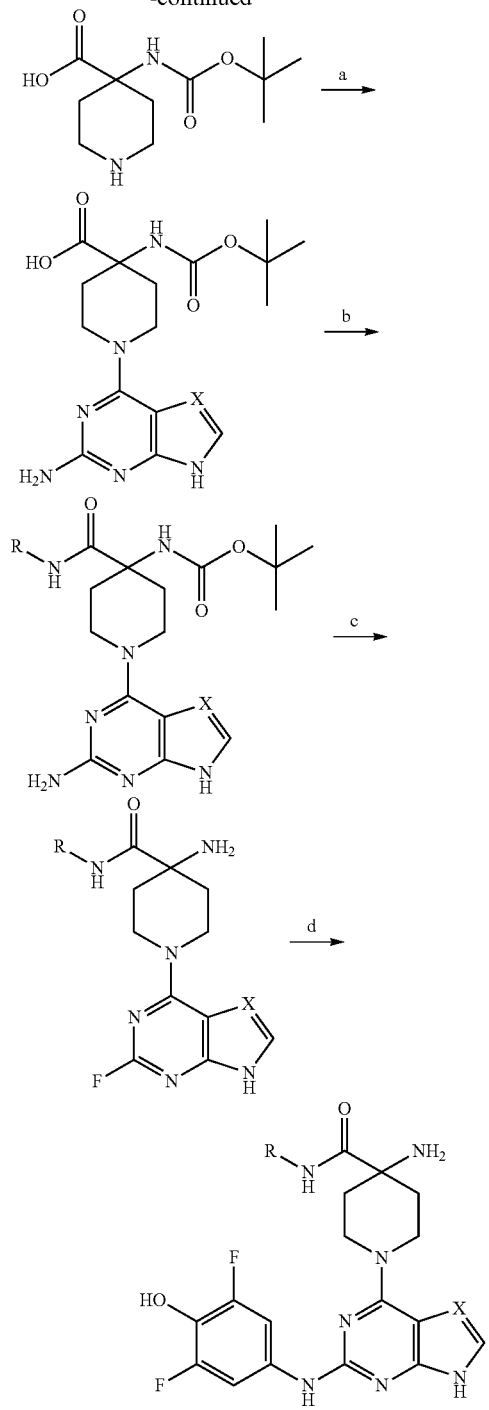

Reagents and Conditions: (a) NaHCO$_3$, MeCN/H$_2$O, reflux, 24 h; (b) amine, EDC, HBT, RT, 16 h; (c) HBF$_4$, 0° C., 1 h; (d) 4M HCl, RT, 16 h.

2-Amino-6-chloropurine was coupled with 4-(BOC-amino)piperidine-4-carboxylic acid to yield intermediate, subsequent BOC deprotection and coupling of the 4-amino-2,6-difluorophenol via TFA/TFE SNAr reaction yielded the desired compounds.

Biological Assays

Compounds designed, selected and/or optimised by methods described above, once produced, can be characterised using a variety of assays known to those skilled in the art to determine whether the compounds have biological activity. For example, the molecules can be characterised by conventional assays, including but not limited to those assays described below, to determine whether they have a predicted activity, binding activity and/or binding specificity.

Furthermore, high-throughput screening can be used to speed up analysis using such assays. As a result, it can be possible to rapidly screen the molecules described herein for activity, using techniques known in the art. General methodologies for performing high-throughput screening are described, for example, in Devlin (1998) High Throughput Screening, Marcel Dekker; and U.S. Pat. No. 5,763,263. High-throughput assays can use one or more different assay techniques including, but not limited to, those described below.

Pharmaceutical Compositions

In some aspects, the present disclosure provides a pharmaceutical composition comprising a compound of the present disclosure as an active ingredient. In some embodiments, the present disclosure provides a pharmaceutical composition comprising at least one compound of each of the formulae described herein, or a pharmaceutically acceptable salt or solvate thereof, and one or more pharmaceutically acceptable carriers or excipients. In some embodiments, the present disclosure provides a pharmaceutical composition comprising at least one compound selected from Tables A1 and A2.

As used herein, the term "composition" is intended to encompass a product comprising the specified ingredients in the specified amounts, as well as any product which results, directly or indirectly, from combination of the specified ingredients in the specified amounts.

The compounds of present disclosure can be formulated foral administration in forms such as tablets, capsules (each of which includes sustained release or timed release formulations), pills, powders, granules, elixirs, tinctures, suspensions, syrups and emulsions. The compounds of present disclosure on can also be formulated for intravenous (bolus or in-fusion), intraperitoneal, topical, subcutaneous, intramuscular or transdermal (e.g., patch) administration, all using forms well known to those of ordinary skill in the pharmaceutical arts.

The formulation of the present disclosure may be in the form of an aqueous solution comprising an aqueous vehicle. The aqueous vehicle component may comprise water and at least one pharmaceutically acceptable excipient. Suitable acceptable excipients include those selected from the group consisting of a solubility enhancing agent, chelating agent, preservative, tonicity agent, viscosity/suspending agent, buffer, and pH modifying agent, and a mixture thereof.

Any suitable solubility enhancing agent can be used. Examples of a solubility enhancing agent include cyclodextrin, such as those selected from the group consisting of hydroxypropyl-β-cyclodextrin, methyl-β-cyclodextrin, randomly methylated-β-cyclodextrin, ethylated-β-cyclodextrin, triacetyl-β-cyclodextrin, peracetylated-β-cyclodextrin, carboxymethyl-β-cyclodextrin, hydroxyethyl-β-cyclodextrin, 2-hydroxy-3-(trimethylammonio)propyl-β-cyclodextrin, glucosyl-β-cyclodextrin, sulfated β-cyclodextrin (S-β-CD), maltosyl-O-cyclodextrin, β-cyclodextrin sulfobutyl ether, branched-β-cyclodextrin, hydroxypropyl-γ-cyclodextrin, randomly methylated-γ-cyclodextrin, and trimethyl-γ-cyclodextrin, and mixtures thereof.

Any suitable chelating agent can be used. Examples of a suitable chelating agent include those selected from the group consisting of ethylenediaminetetraacetic acid and metal salts thereof, disodium edetate, trisodium edetate, and tetrasodium edetate, and mixtures thereof.

Any suitable preservative can be used. Examples of a preservative include those selected from the group consisting of quaternary ammonium salts such as benzalkonium halides (preferably benzalkonium chloride), chlorhexidine gluconate, benzethonium chloride, cetyl pyridinium chloride, benzyl bromide, phenylmercury nitrate, phenylmercury acetate, phenylmercury neodecanoate, merthiolate, methylparaben, propylparaben, sorbic acid, potassium sorbate, sodium benzoate, sodium propionate, ethyl p-hydroxybenzoate, propylaminopropyl biguanide, and butyl-p-hydroxybenzoate, and sorbic acid, and mixtures thereof.

The aqueous vehicle may also include a tonicity agent to adjust the tonicity (osmotic pressure). The tonicity agent can be selected from the group consisting of a glycol (such as propylene glycol, diethylene glycol, triethylene glycol), glycerol, dextrose, glycerin, mannitol, potassium chloride, and sodium chloride, and a mixture thereof.

The aqueous vehicle may also contain a viscosity/suspending agent. Suitable viscosity/suspending agents include those selected from the group consisting of cellulose derivatives, such as methyl cellulose, ethyl cellulose, hydroxyethylcellulose, polyethylene glycols (such as polyethylene glycol 300, polyethylene glycol 400), carboxymethyl cellulose, hydroxypropylmethyl cellulose, and cross-linked acrylic acid polymers (carbomers), such as polymers of acrylic acid cross-linked with polyalkenyl ethers or divinyl glycol (Carbopols—such as Carbopol 934, Carbopol 934P, Carbopol 971, Carbopol 974 and Carbopol 974P), and a mixture thereof.

In order to adjust the formulation to an acceptable pH (typically a pH range of about 5.0 to about 9.0, more preferably about 5.5 to about 8.5, particularly about 6.0 to about 8.5, about 7.0 to about 8.5, about 7.2 to about 7.7, about 7.1 to about 7.9, or about 7.5 to about 8.0), the formulation may contain a pH modifying agent. The pH modifying agent is typically a mineral acid or metal hydroxide base, selected from the group of potassium hydroxide, sodium hydroxide, and hydrochloric acid, and mixtures thereof, and preferably sodium hydroxide and/or hydrochloric acid. These acidic and/or basic pH modifying agents are added to adjust the formulation to the target acceptable pH range. Hence it may not be necessary to use both acid and base—depending on the formulation, the addition of one of the acid or base may be sufficient to bring the mixture to the desired pH range.

The aqueous vehicle may also contain a buffering agent to stabilise the pH. When used, the buffer is selected from the group consisting of a phosphate buffer (such as sodium dihydrogen phosphate and disodium hydrogen phosphate), a borate buffer (such as boric acid, or salts thereof including disodium tetraborate), a citrate buffer (such as citric acid, or salts thereof including sodium citrate), and ε-aminocaproic acid, and mixtures thereof.

The formulation may further comprise a wetting agent. Suitable classes of wetting agents include those selected from the group consisting of polyoxypropylene-polyoxyethylene block copolymers (poloxamers), polyethoxylated ethers of castor oils, polyoxyethylenated sorbitan esters (polysorbates), polymers of oxyethylated octyl phenol (Tyloxapol), polyoxyl 40 stearate, fatty acid glycol esters, fatty acid glyceryl esters, sucrose fatty esters, and polyoxyethylene fatty esters, and mixtures thereof.

Oral compositions generally include an inert diluent or an edible pharmaceutically acceptable carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavouring agent such as peppermint, methyl salicylate, orange flavoring.

According to a further aspect of the disclosure there is provided a pharmaceutical composition which comprises a compound of the disclosure as defined hereinbefore, or a pharmaceutically acceptable salt, hydrate or solvate thereof, in association with a pharmaceutically acceptable diluent or carrier.

The compositions of the disclosure may be in a form suitable foral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular, intraperitoneal or intramuscular dosing or as a suppository for rectal dosing).

The compositions of the disclosure may be obtained by conventional procedures using conventional pharmaceutical excipients, well known in the art. Thus, compositions intended foral use may contain, for example, one or more colouring, sweetening, flavouring and/or preservative agents.

An effective amount of a compound of the present disclosure for use in therapy is an amount sufficient to treat or prevent an inflammasome related condition referred to herein, slow its progression and/or reduce the symptoms associated with the condition.

An effective amount of a compound of the present disclosure for use in therapy is an amount sufficient to treat an inflammasome related condition referred to herein, slow its progression and/or reduce the symptoms associated with the condition.

The size of the dose for therapeutic or prophylactic purposes of a compound will naturally vary according to the nature and severity of the conditions, the age and sex of the animal or patient and the route of administration, according to well-known principles of medicine.

Uses of the Compounds

In some aspects, the present disclosure provides methods for modulating RSK activity in a subject, the method comprising administering to the subject a therapeutically effective amount of at least one compound of the present disclosure, or a pharmaceutically acceptable salt thereof.

In some aspects, the present disclosure provides at least one compound of the present disclosure, or a pharmaceutically acceptable salt thereof, for use in modulating RSK activity in a subject.

In some aspects, the present disclosure provides the use of at least one compound of the present disclosure, or a pharmaceutically acceptable salt thereof, in the manufacture of a medicament for modulating RSK activity in a subject.

In some aspects, the present disclosure provides methods for modulating RSK activity in at least one cell in vitro, the method comprising contacting that cell with at least one compound of the present disclosure, or a pharmaceutically acceptable salt thereof.

In some aspects, RSK can be RSK1, RSK2, RSK3 or RSK4. In some aspects, RSK can be RSK2.

In some aspects, modulating RSK activity comprises inhibiting RSK activity. In some aspects, modulating RSK activity comprises inhibiting RSK activity in a specific target cell, e.g. a tumor cell or a cancer cell. In some aspects, modulating RSK activity comprises inhibiting AMPK activity by at least about 10%, or at least about 20%, or at least about 30%, or at least about 40%, or at least about 50%, or at least about 60%, or at least about 70%, or at least about 80%, or at least about 90%, or at least about 99%.

In some aspects, the present disclosure provides methods of preventing, treating, or ameliorating cancer or preventing metastasis of cancer in a subject, the methods comprising administering a therapeutically effective amount of at least one compound of the present disclosure, or a pharmaceutically acceptable salt thereof. In these methods, the at least one compound of the present disclosure, or pharmaceutically acceptable salt thereof, may be administered to the subject within a pharmaceutical composition.

In some aspects, the present disclosure provides a method of treating or preventing cancer in a subject, the method comprising administering to the subject a therapeutically effective amount of at least one compound of the present disclosure, or a pharmaceutically acceptable salt thereof. In some aspects, the present disclosure provides at least one compound of the present disclosure, or a pharmaceutically acceptable salt thereof, for use in the treatment or prevention of cancer in a subject. In some aspects, the present disclosure provides the use of at least one compound of the present disclosure, or a pharmaceutically acceptable salt thereof, for the manufacture of a medicament for the treatment or prevention of cancer in a subject.

In some aspects, the subject can be a mammal. In some aspects, the subject can be a human. In some aspects, the subject can be a mouse.

In some aspects, the cancer can be acute myeloid leukemia.

In some aspects, the cancer can be breast cancer, colorectal cancer, head and neck squamous cell carcinoma (HNSCC), leukemia, lung cancer, malignant melanoma, multiple myeloma, acute myeloid leukemia, ovarian carcinoma or prostate cancer.

In some aspects, the cancer can be a carcinoma, a lymphoma, a blastoma, a sarcoma, a leukemia, a brain cancer, a breast cancer, a blood cancer, a bone cancer, a lung cancer, a skin cancer, a liver cancer, an ovarian cancer, a bladder cancer, a renal cancer, a kidney cancer, a gastric cancer, a thyroid cancer, a pancreatic cancer, an esophageal cancer, a prostate cancer, a cervical cancer, a uterine cancer, a stomach cancer, a soft tissue cancer, a laryngeal cancer, a small intestine cancer, a testicular cancer, an anal cancer, a vulvar cancer, a joint cancer, an oral cancer, a pharynx cancer or a colorectal cancer.

In some aspects, the cancer can be adrenocortical carcinoma, bladder urothelial carcinoma, breast invasive carcinoma, cervical squamous cell carcinoma, endocervical adenocarcinoma, cholangiocarcinoma, colon adenocarcinoma, lymphoid neoplasm diffuse large B-cell lymphoma, esophageal carcinoma, glioblastoma multiforme, head and neck squamous cell carcinoma, kidney chromophobe, kidney renal clear cell carcinoma, kidney renal papillary cell carcinoma, acute myeloid leukemia, brain lower grade glioma, liver hepatocellular carcinoma, lung adenocarcinoma, lung squamous cell carcinoma, mesothelioma, ovarian serous cystadenocarcinoma, pancreatic adenocarcinoma, pheochromocytoma, paraganglioma, prostate adenocarcinoma, rectum adenocarcinoma, sarcoma, skin cutaneous melanoma, stomach adenocarcinoma, testicular germ cell tumors, thyroid carcinoma, thymoma, uterine carcinosarcoma, uveal melanoma. Other examples include breast cancer, lung cancer, lymphoma, melanoma, liver cancer, colorectal cancer, ovarian cancer, bladder cancer, renal cancer or gastric cancer. Further examples of cancer include neuroendocrine cancer, non-small cell lung cancer (NSCLC), small cell lung cancer, thyroid cancer, endometrial cancer, biliary cancer, esophageal cancer, anal cancer, salivary, cancer, vulvar cancer, cervical cancer, Acute lymphoblastic leukemia (ALL), Acute myeloid leukemia (AML), Adrenal gland tumors, Anal cancer, Bile duct cancer, Bladder cancer, Bone cancer, Bowel cancer, Brain tumors, Breast cancer, Cancer of unknown primary (CUP), Cancer spread to bone, Cancer spread to brain, Cancer spread to liver, Cancer spread to lung, Carcinoid, Cervical cancer, Children's cancers, Chronic lymphocytic leukemia (CLL), Chrome myeloid leukemia (CML), Colorectal cancer, Ear cancer, Endometrial cancer, Eye cancer, Follicular dendritic cell sarcoma, Gallbladder cancer, Gastric cancer, Gastro esophageal junction cancers, Germ cell tumors, Gestational trophoblastic disease (GIT)), Hairy cell leukemia, Head and neck cancer, Hodgkin lymphoma, Kaposi's sarcoma, Kidney cancer, Laryngeal cancer, Leukemia, Gastric linitis plastica, Liver cancer, Lung cancer, Lymphoma, Malignant schwannoma, Mediastinal germ cell tumors, Melanoma skin cancer, Men's cancer, Merkel cell skin cancer, Mesothelioma, Molar pregnancy, Mouth and oropharyngeal cancer, Myeloma, Nasal and paranasal sinus cancer, Nasopharyngeal cancer, Neuroblastoma, Neuroendocrine tumors, Non-Hodgkin lymphoma (NHL), Esophageal cancer, Ovarian cancer, Pancreatic cancer, Penile cancer, Persistent trophoblastic disease and choriocarcinoma, Pheochromocytoma, Prostate cancer, Pseudomyxoma peritonei, Rectal cancer. Retinoblastoma, Salivary gland cancer, Secondary' cancer, Signet cell cancer, Skin cancer, Small bowel cancer, Soft tissue sarcoma, Stomach cancer, T cell childhood non Hodgkin lymphoma (NHL), Testicular cancer, Thymus gland cancer, Thyroid cancer, Tongue cancer, Tonsil cancer, Tumors of the adrenal gland, Uterine cancer. Vaginal cancer, Vulval cancer, Wilms' tumor, Womb cancer and Gynaecological cancer. Examples of cancer also include, but are not limited to, Hematologic malignancies, Lymphoma, Cutaneous T-cell lymphoma, Peripheral T-cell lymphoma, Hodgkin's lymphoma, Non-Hodgkin's lymphoma, Multiple myeloma, Chrome lymphocytic leukemia, chronic myeloid leukemia, acute myeloid leukemia, Myelodysplastic syndromes, Myelofibrosis, Biliary tract cancer, Hepatocellular cancer, Colorectal cancer, Breast cancer, Lung cancer, Non-small cell lung cancer, Ovarian cancer, Thyroid Carcinoma, Renal Cell Carcinoma, Pancreatic cancer, Bladder cancer, skin cancer, malignant melanoma, merkel cell carcinoma, Uveal Melanoma or Glioblastoma multiforme. The present disclosure provides a method of treating a cancer in a subject, the method comprising administering to the subject a therapeutically effective amount of at least one compound of the present disclosure in combination with a therapeutically effective amount of at least one additional therapeutic agent. The present disclosure provides at least one compound of the present disclosure for use in the treatment of a cancer in a subject, wherein the at least one compound of the present disclosure is for administration to the subject in a therapeutically effective amount, and wherein the treatment further comprises administering to the subject a therapeutically effective amount of at least one additional therapeutic agent. The present disclosure provides at least one compound of the present disclosure for the manufacture of a medicament for the treatment of a cancer in a subject, wherein the at least one compound is for administration to the subject in a therapeutically effective amount and wherein the treatment further comprises administering to the subject a therapeutically effective amount of at least one additional therapeutic agent.

The present disclosure provides a combination comprising at least one compound of the present disclosure and at least one additional therapeutic agent for use in the treatment of a cancer in a subject, wherein the combination is for the administration to the subject in a therapeutically effective amount. The present disclosure provides a combination comprising at least one compound of the present disclosure and at least one additional therapeutic agent for the manufacture of a medicament for the treatment of a cancer in a subject, wherein the combination is for administration to the subject in a therapeutically effective amount.

Additional therapeutic agents can include, but are not limited to, chemotherapeutic agents, anti-cancer agents, DNA alkylating agents, DNA damage response (DDR) inhibitors, cell-cycle checkpoint inhibitors, PARP inhibitors, HDAC inhibitors, kinase inhibitors, Bcl-2 inhibitors, Mcl-1 inhibitors, PD-L1 targeted agents, immunotherapy agents and bioenergetics modulators. Additional therapeutic agents can include, but are not limited to cisplatin, cytarabine, doxorubicin, paclitaxel, temozolomide, dasatinib, nilotinib, fluvestrant, venetoclax, metformin, or combinations thereof.

In some aspects, anti-cancer agents can include, but are not limited to, 13-cis-Retinoic Acid, 2-CdA, 2-Chlorodeoxyadenosine, 5-Azacitidine, 5-Fluorouracil, 5-FU, 6-Mercaptopurine, 6-MP, 6-TG, 6-Thioguanine, Abemaciclib, Abiraterone acetate, Abraxane, Accutane, Actinomycin-D, Adcetris, Ado-Trastuzumab Emtansine, Adriamycin, Adrucil, Afatinib, Afinitor, Agrylin, Ala-Cort, Aldesleukin, Alemtuzumab, Alecensa, Alectinib, Alimta, Alitretinoin, Alkaban-AQ, Alkeran, All-transretinoic Acid, Alpha Interferon, Altretamine, Alunbrig, Amethopterin, Amifostine, Aminoglutethimide, Anagrelide, Anandron, Anastrozole, Apalutamide, Arabinosylcytosine, Ara-C, Aranesp, Aredia, Arimidex, Aromasin, Arranon, Arsenic Trioxide, Arzerra, Asparaginase, Atezolizumab, Atra, Avastin, Avelumab, Axicabtagene Ciloleucel, Axitinib, Azacitidine, Bavencio, Bcg, Beleodaq, Belinostat, Bendamustine, Bendeka, Besponsa, Bevacizumab, Bexarotene, Bexxar, Bicalutamide, Bicnu, Blenoxane, Bleomycin, Blinatumomab, Blincyto, Bortezomib, Bosulif, Bosutinib, Brentuximab Vedotin, Brigatinib, Busulfan, Busulfex, C225, Cabazitaxel, Cabozantinib, Calcium Leucovorin, Campath, Camptosar, Camptothecin-11, Capecitabine, Caprelsa, Carac, Carboplatin, Carfilzomib, Carmustine, Carmustine Wafer, Casodex, CCI-779, Ccnu, Cddp, Ceenu, Ceritinib, Cerubidine, Cetuximab, Chlorambucil, Cisplatin, Citrovorum Factor, Cladribine, Clofarabine, Clolar, Cobimetinib, Cometriq, Cortisone, Cosmegen, Cotellic, Cpt-11, Crizotinib, Cyclophosphamide, Cyramza, Cytadren, Cytarabine, Cytarabine Liposomal, Cytosar-U, Cytoxan, Dabrafenib, Dacarbazine, Dacogen, Dactinomycin, Daratumumab, Darbepoetin Alfa, Darzalex, Dasatinib, Daunomycin, Daunorubicin, Daunorubicin Cytarabine (Liposomal), daunorubicin-hydrochloride, Daunorubicin Liposomal, DaunoXome, Decadron, Decitabine, Degarelix, Delta-Cortef, Deltasone, Denileukin Diftitox, Denosumab, DepoCyt, Dexamethasone, Dexamethasone Acetate, Dexamethasone Sodium Phosphate, Dexasone, Dexrazoxane, Dhad, Dic, Diodex, Docetaxel, Doxil, Doxorubicin, Doxorubicin Liposomal, Droxia, DTIC, Dtic-Dome, Duralone, Durvalumab, Eculizumab, Efudex, Ellence, Elotuzumab, Eloxatin, Elspar, Eltrombopag, Emcyt, Empliciti, Enasidenib, Enzalutamide, Epirubicin, Epoetin Alfa, Erbitux, Eribulin, Erivedge, Erleada, Erlotinib, Erwinia L-asparaginase, Estramustine, Ethyol, Etopophos, Etoposide, Etoposide Phosphate, Eulexin, Everolimus, Evista, Exemestane, Fareston, Farydak, Faslodex, Femara, Filgrastim, Firmagon, Floxuridine, Fludara, Fludarabine, Fluoroplex, Fluorouracil, Fluorouracil (cream), Fluoxymesterone, Flutamide, Folinic Acid, Folotyn, Fudr, Fulvestrant, G-Csf, Gazyva, Gefitinib, Gemcitabine, Gemtuzumab ozogamicin, Gemzar, Gilotrif, Gleevec, Gleostine, Gliadel Wafer, Gm-Csf, Goserelin, Granix, Granulocyte—Colony Stimulating Factor, Granulocyte Macrophage Colony Stimulating Factor, Halaven, Halotestin, Herceptin, Hexadrol, Hexalen, Hexamethylmelamine, Hmm, Hycamtin, Hydrea, Hydrocort Acetate, Hydrocortisone, Hydrocortisone Sodium Phosphate, Hydrocortisone Sodium Succinate, Hydrocortone Phosphate, Hydroxyurea, Ibrance, Ibritumomab, Ibritumomab Tiuxetan, Ibrutinib, Iclusig, Idamycin, Idarubicin, Idelalisib, Idhifa, Ifex, IFN-alpha, Ifosfamide, IL-11, IL-2, Imbruvica, Imatinib Mesylate, Imfinzi, Imidazole Carboxamide, Imlygic, Inlyta, Inotuzumab Ozogamicin, Interferon-Alfa, Interferon Alfa-2b (PEG Conjugate), Interleukin-2, Interleukin-11, Intron A (interferon alfa-2b), Ipilimumab, Iressa, Irinotecan, Irinotecan (Liposomal), Isotretinoin, Istodax, Ixabepilone, Ixazomib, Ixempra, Jakafi, Jevtana, Kadcyla, Keytruda, Kidrolase, Kisqali, Kymriah, Kyprolis, Lanacort, Lanreotide, Lapatinib, Lartruvo, L-Asparaginase, Lbrance, Lcr, Lenalidomide, Lenvatinib, Lenvima, Letrozole, Leucovorin, Leukeran, Leukine, Leuprolide, Leurocristine, Leustatin, Liposomal Ara-C, Liquid Pred, Lomustine, Lonsurf, L-PAM, L-Sarcolysin, Lupron, Lupron Depot, Lynparza, Marqibo, Matulane, Maxidex, Mechlorethamine, Mechlorethamine Hydrochloride, Medralone, Medrol, Megace, Megestrol, Megestrol Acetate, Mekinist, Mercaptopurine, Mesna, Mesnex, Methotrexate, Methotrexate Sodium, Methylprednisolone, Meticorten, Midostaurin, Mitomycin, Mitomycin-C, Mitoxantrone, M-Prednisol, MTC, MTX, Mustargen, Mustine, Mutamycin, Myleran, Mylocel, Mylotarg, Navelbine, Necitumumab, Nelarabine, Neosar, Neratinib, Nerlynx, Neulasta, Neumega, Neupogen, Nexavar, Nilandron, Nilotinib, Nilutamide, Ninlaro, Nipent, Niraparib, Nitrogen Mustard, Nivolumab, Nolvadex, Novantrone, Nplate, Obinutuzumab, Octreotide, Octreotide Acetate, Odomzo, Ofatumumab, Olaparib, Olaratumab, Omacetaxine, Oncospar, Oncovin, Onivyde, Ontak, Onxal, Opdivo, Oprelvekin, Orapred, Orasone, Osimertinib, Otrexup, Oxaliplatin, Paclitaxel, Paclitaxel Protein-bound, Palbociclib, Pamidronate, Panitumumab, Panobinostat, Panretin, Paraplatin, Pazopanib, Pediapred, Peg Interferon, Pegaspargase, Pegfilgrastim, Peg-Intron, PEG-L-asparaginase, Pembrolizumab, Pemetrexed, Pentostatin, Perjeta, Pertuzumab, Phenylalanine Mustard, Platinol, Platinol-AQ, Pomalidomide, Pomalyst, Ponatinib, Portrazza, Pralatrexate, Prednisolone, Prednisone, Prelone, Procarbazine, Procrit, Proleukin, Prolia, Prolifeprospan 20 with Carmustine Implant, Promacta, Provenge, Purinethol, Radium 223 Dichloride, Raloxifene, Ramucirumab, Rasuvo, Regorafenib, Revlimid, Rheumatrex, Ribociclib, Rituxan, Rituxan Hycela, Rituximab, Rituximab Hyalurodinase, Roferon-A (Interferon Alfa-2a), Romidepsin, Romiplostim, Rubex, Rubidomycin Hydrochloride, Rubraca, Rucaparib, Ruxolitinib, Rydapt, Sandostatin, Sandostatin LAR, Sargramostim, Siltuximab, Sipuleucel-T, Soliris, Solu-Cortef, Solu-Medrol, Somatuline, Sonidegib, Sorafenib, Sprycel, Sti-571, Stivarga, Streptozocin, SU11248, Sunitinib, Sutent, Sylvant, Synribo, Tafinlar, Tagrisso, Talimogene Laherparepvec, Tamoxifen, Tarceva, Targretin, Tasigna, Taxol, Taxotere, Tecentriq, Temodar, Temozolomide, Temsirolimus, Teniposide, Tespa, Thalidomide, Thalomid, TheraCys, Thioguanine, Thioguanine Tabloid, Thiophosphoamide, Thioplex, Thiotepa, Tice, Tisagenlecleucel, Toposar, Topotecan, Toremifene, Torisel, Tositumomab, Trabectedin, Trametinib, Trastuzumab, Treanda, Trelstar, Tretinoin, Trexall, Trifluridine/Tipiricil, Triptorelin pamoate, Trisenox, Tspa, T-VEC, Tykerb, Valrubicin, Valstar, Vandetanib, VCR, Vectibix, Velban, Velcade, Vemurafenib, Venclexta, Venetoclax, VePesid, Verzenio, Vesanoid, Viadur, Vidaza, Vinblastine, Vinblastine Sulfate, Vincasar Pfs, Vincristine, Vincristine Liposomal, Vinorelbine, Vinorelbine Tartrate, Vismodegib, Vlb, VM-26, Vorinostat, Votrient, VP-16, Vumon, Vyxeos, Xalkori Capsules, Xeloda, Xgeva, Xofigo, Xtandi, Yervoy, Yescarta, Yondelis, Zaltrap, Zanosar, Zarxio, Zejula, Zelboraf, Zevalin, Zinecard, Ziv-aflibercept, Zoladex, Zoledronic Acid, Zolinza, Zometa, Zydelig, Zykadia, Zytiga, or any combination thereof.

Immunotherapy can comprise administering checkpoint inhibitors. Checkpoint inhibitors can comprise antibodies. Checkpoint inhibitors include, but are not limited to, anti-CTLA4 antibodies, anti-PD-1 antibodies, anti-PD-L1 antibodies, anti-A2AR antibodies, anti-B7-H3 antibodies, anti-B7-H4 antibodies, anti-BTLA antibodies, anti-IDO antibodies, anti-KIR antibodies, anti-LAG3 antibodies, anti-TIM3 antibodies and anti-VISTA (V-domain Ig suppressor of T cell activation) antibodies.

Anti-CTLA4 antibodies can include, but are not limited to, ipilimumab, tremelimumab and AGEN-1884. Anti-PD-1 antibodies include, but are not limited to, pembrolizumab, nivolumab pidilizumab, cemiplimab, REGN2810, AMP-224, MEDI0680, PDR001 and CT-001. Anti-PD-L1 antibodies include, but are not limited to atezolizumab, avelumab and durvalumab. Anti-CD137 antibodies include, but are not limited to, urelumab. Anti-B7-H3 antibodies include, but are not limited to, MGA271. Anti-KIR antibodies include, but are not limited to, Lirilumab. Anti-LAG3 antibodies include, but are not limited to, BMS-986016.

The term "immunotherapy" can refer to activating immunotherapy or suppressing immunotherapy. As will be appreciated by those in the art, activating immunotherapy refers to the use of a therapeutic agent that induces, enhances, or promotes an immune response, including, e.g., a T cell response while suppressing immunotherapy refers to the use of a therapeutic agent that interferes with, suppresses, or inhibits an immune response, including, e.g., a T cell response. Activating immunotherapy may comprise the use of checkpoint inhibitors. Activating immunotherapy may comprise administering to a subject a therapeutic agent that activates a stimulatory checkpoint molecule. Stimulatory checkpoint molecules include, but are not limited to, CD27, CD28, CD40, CD122, CD137, OX40, GITR and ICOS. Therapeutic agents that activate a stimulatory checkpoint molecule include, but are not limited to, MED10562, TGN1412, CDX-1127, lipocalin.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity. An antibody that binds to a target refers to an antibody that is capable of binding the target with sufficient affinity such that the antibody is useful as a diagnostic and/or therapeutic agent in targeting the target. In one embodiment, the extent of binding of an anti-target antibody to an unrelated, non-target protein is less than about 10% of the binding of the antibody to target as measured, e.g., by a radioimmunoassay (RIA) or biacore assay. In certain embodiments, an antibody that binds to a target has a dissociation constant (Kd) of <1 µM, <100 nM, <10 nM, <1 nM, <0.1 nM, <0.01 nM, or <0.001 nM (e.g. $10^8$ M or less, e.g. from $10^8$ M to $10^{13}$ M, e.g., from $10^9$ M to $10^{13}$ M). In certain embodiments, an anti-target antibody binds to an epitope of a target that is conserved among different species.

A "blocking antibody" or an "antagonist antibody" is one that partially or fully blocks, inhibits, interferes, or neutralizes a normal biological activity of the antigen it binds. For example, an antagonist antibody may block signaling through an immune cell receptor (e.g., a T cell receptor) so as to restore a functional response by T cells (e.g., proliferation, cytokine production, target cell killing) from a dysfunctional state to antigen stimulation.

An "agonist antibody" or "activating antibody" is one that mimics, promotes, stimulates, or enhances a normal biological activity of the antigen it binds. Agonist antibodies can also enhance or initiate signaling by the antigen to which it binds. In some embodiments, agonist antibodies cause or activate signaling without the presence of the natural ligand. For example, an agonist antibody may increase memory T cell proliferation, increase cytokine production by memory T cells, inhibit regulatory T cell function, and/or inhibit regulatory T cell suppression of effector T cell function, such as effector T cell proliferation and/or cytokine production.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')2; diabodies; linear antibodies; single-chain antibody molecules (e.g. scFv); and multispecific antibodies formed from antibody fragments.

As used herein, the term additional therapeutic agents can also comprise the administration of radiation therapy, surgery or any combination thereof.

The present disclosure provides a method of treating AML in a subject, the method comprising administering to the subject a therapeutically effective amount of at least one compound of the present disclosure in combination with a therapeutically effective amount of at least one BCL-2 inhibitor. The present disclosure provides at least one compound of the present disclosure for use in the treatment of AML in a subject, wherein the at least one compound of the present disclosure is for administration to the subject in a therapeutically effective amount, and wherein the treatment further comprises administering to the subject a therapeutically effective amount of at least one BCL-2 inhibitor. The present disclosure provides at least one compound of the present disclosure for the manufacture of a medicament for the treatment of AML in a subject, wherein the at least one compound is for administration to the subject in a therapeutically effective amount and wherein the treatment further comprises administering to the subject a therapeutically effective amount of at least one BCL-2 inhibitor.

The present disclosure a combination comprising at least one compound of the present disclosure and at least one BCL-2 inhibitor for use in the treatment of AML in a subject, wherein the combination is for the administration to the subject in a therapeutically effective amount. The present disclosure provides a combination comprising at least one compound of the present disclosure and at least one BCL-2 inhibitor for the manufacture of a medicament for the treatment of AML in a subject, wherein the combination is for administration to the subject in a therapeutically effective amount.

BCL-2 inhibitors can include, but are not limited to, venetoclax, navitoclax, and any other BCL-2 inhibitor known in the art.

The present disclosure provides a method of treating AML in a subject, the method comprising administering to the subject a therapeutically effective amount of at least one compound of the present disclosure in combination with a therapeutically effective amount of venetoclax. The present disclosure provides at least one compound of the present disclosure for use in the treatment of AML in a subject, wherein the at least one compound of the present disclosure is for administration to the subject in a therapeutically effective amount, and wherein the treatment further comprises administering to the subject a therapeutically effective amount of venetoclax. The present disclosure provides at least one compound of the present disclosure for the manufacture of a medicament for the treatment of AML in a subject, wherein the at least one compound is for administration to the subject in a therapeutically effective amount and wherein the treatment further comprises administering to the subject a therapeutically effective amount of venetoclax.

The present disclosure a combination comprising at least one compound of the present disclosure and venetoclax for use in the treatment of AML in a subject, wherein the combination is for the administration to the subject in a therapeutically effective amount. The present disclosure provides a combination comprising at least one compound of the present disclosure and venetoclax for the manufacture of a medicament for the treatment of AML in a subject, wherein the combination is for administration to the subject in a therapeutically effective amount.

The present disclosure provides a method of treating AML in a subject, the method comprising administering to the subject a therapeutically effective amount of at least one compound of the present disclosure in combination with a therapeutically effective amount of at least one hypomethylating agent. The present disclosure provides at least one compound of the present disclosure for use in the treatment of AML in a subject, wherein the at least one compound of the present disclosure is for administration to the subject in a therapeutically effective amount, and wherein the treatment further comprises administering to the subject a therapeutically effective amount of at least one hypomethylating agent. The present disclosure provides at least one compound of the present disclosure for the manufacture of a medicament for the treatment of AML in a subject, wherein the at least one compound is for administration to the subject in a therapeutically effective amount and wherein the treatment further comprises administering to the subject a therapeutically effective amount of at least one hypomethylating agent.

The present disclosure a combination comprising at least one compound of the present disclosure and at least one hypomethylating agent for use in the treatment of AML in a subject, wherein the combination is for the administration to the subject in a therapeutically effective amount. The present disclosure provides a combination comprising at least one compound of the present disclosure and at least one hypomethylating agent for the manufacture of a medicament for the treatment of AML in a subject, wherein the combination is for administration to the subject in a therapeutically effective amount.

Hypomethylating agents can include, but are not limited to, azacitidine, decitabine and any other hypomethlyating agent known in the art.

Examples of other chemotherapeutic agents that can be used in combination with the compounds of this disclosure include DNA-targeted agents, including DNA alkylating agents and topoisomerase inhibitors, including cisplatin, capecitabine, carboplatin, cyclophosphamide, cytarabine, dauoribicin, docetaxel, doxorubicin, 5-fluorouracil, gemcitabine, methotrexate, paclitaxel, premetrexed, irinotecan temozolomide, topotecan, or combinations thereof.

The disclosed compounds also may be combined with radiotherapy employing radioisotopes (such as $^{32}$P, $^{90}$Y, $^{125}$I, $^{131}$I, and $^{177}$Lu), particle beams (such as proton, neutron and electron beams) and electromagnetic radiation (such as gamma rays, x-rays and photodynamic therapy using photosensitizers and visible or ultraviolet rays).

Definitions

Unless otherwise stated, the following terms used in the specification and claims have the following meanings set out below.

Without wishing to be limited by this statement, it is understood that, while various options for variables are described herein, the disclosure intends to encompass operable embodiments having combinations of the options. The disclosure may be interpreted as excluding the non-operable embodiments caused by certain combinations of the options.

As used herein, "alkyl", "$C_1$, $C_2$, $C_3$, $C_4$, $C_5$ or $C_6$ alkyl" or "$C_1$-$C_6$ alkyl" is intended to include $C_1$, $C_2$, $C_3$, $C_4$, $C_5$ or $C_6$ straight chain (linear) saturated aliphatic hydrocarbon groups and $C_3$, $C_4$, $C_5$ or $C_6$ branched saturated aliphatic hydrocarbon groups. For example, $C_1$-$C_6$ alkyl is intends to include $C_1$, $C_2$, $C_3$, $C_4$, $C_5$ and $C_6$ alkyl groups. Examples of alkyl include, moieties having from one to six carbon atoms, such as, but not limited to, methyl, ethyl, n-propyl, i-propyl, n-butyl, s-butyl, t-butyl, n-pentyl, i-pentyl, or n-hexyl. In some embodiments, a straight chain or branched alkyl has six or fewer carbon atoms (e.g., $C_1$-$C_6$ for straight chain, $C_3$-$C_6$ for branched chain), and in another embodiment, a straight chain or branched alkyl has four or fewer carbon atoms.

As used herein, the term "optionally substituted alkyl" refers to unsubstituted alkyl or alkyl having designated substituents replacing one or more hydrogen atoms on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

As used herein, the term "alkenyl" includes unsaturated aliphatic groups analogous in length and possible substitution to the alkyls described above, but that contain at least one double bond. For example, the term "alkenyl" includes straight chain alkenyl groups (e.g., ethenyl, propenyl, butenyl, pentenyl, hexenyl, heptenyl, octenyl, nonenyl, decenyl), and branched alkenyl groups. In certain embodiments, a straight chain or branched alkenyl group has six or fewer carbon atoms in its backbone (e.g., $C_2$-$C_6$ for straight chain, $C_3$-$C_6$ for branched chain). The term "$C_2$-$C_6$" includes alkenyl groups containing two to six carbon atoms. The term "$C_3$-$C_6$" includes alkenyl groups containing three to six carbon atoms.

As used herein, the term "optionally substituted alkenyl" refers to unsubstituted alkenyl or alkenyl having designated substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, heterocyclyl, alkylaryl, or an aromatic or heteroaromatic moiety.

As used herein, the term "alkynyl" includes unsaturated aliphatic groups analogous in length and possible substitution to the alkyls described above, but which contain at least one triple bond. For example, "alkynyl" includes straight chain alkynyl groups (e.g., ethynyl, propynyl, butynyl, pentynyl, hexynyl, heptynyl, octynyl, nonynyl, decynyl), and branched alkynyl groups. In certain embodiments, a straight chain or branched alkynyl group has six or fewer carbon atoms in its backbone (e.g., $C_2$-$C_6$ for straight chain, $C_3$-$C_6$ for branched chain). The term "$C_2$-$C_6$" includes alkynyl groups containing two to six carbon atoms. The term "$C_3$-$C_6$" includes alkynyl groups containing three to six carbon atoms. As used herein, "$C_2$-$C_6$ alkenylene linker" or "$C_2$-$C_6$ alkynylene linker" is intended to include $C_2$, $C_3$, $C_4$, $C_5$ or $C_6$ chain (linear or branched) divalent unsaturated aliphatic hydrocarbon groups. For example, $C_2$-$C_6$ alkenylene linker is intended to include $C_2$, $C_3$, $C_4$, $C_5$ and $C_6$ alkenylene linker groups.

As used herein, the term "optionally substituted alkynyl" refers to unsubstituted alkynyl or alkynyl having designated substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Other optionally substituted moieties (such as optionally substituted cycloalkyl, heterocycloalkyl, aryl, or heteroaryl) include both the unsubstituted moieties and the moieties having one or more of the designated substituents. For example, substituted heterocycloalkyl includes those substituted with one or more alkyl groups, such as 2,2,6,6-tetramethyl-piperidinyl and 2,2,6,6-tetramethyl-1,2,3,6-tetrahydropyridinyl.

As used herein, the term "cycloalkyl" refers to a saturated or partially unsaturated hydrocarbon monocyclic or polycyclic (e.g., fused, bridged, or spiro rings) system having 3 to 30 carbon atoms (e.g., $C_3$-$C_{12}$, $C_3$-$C_{10}$, or $C_3$-$C_8$). Examples of cycloalkyl include, but are not limited to, cyclopropyl, cyclobutyl, cyclopentyl, cyclohexyl, cycloheptyl, cyclooctyl, cyclopentenyl, cyclohexenyl, cycloheptenyl, 1,2,3,4-tetrahydronaphthalenyl, and adamantyl. In the case of polycyclic cycloalkyl, only one of the rings in the cycloalkyl needs to be non-aromatic.

As used herein, the term "heterocycloalkyl" refers to a saturated or partially unsaturated 3-8 membered monocyclic, 7-12 membered bicyclic (fused, bridged, or spiro rings), or 11-14 membered tricyclic ring system (fused, bridged, or spiro rings) having one or more heteroatoms (such as O, N, S, P, or Se), e.g., 1 or 1-2 or 1-3 or 1-4 or 1-5 or 1-6 heteroatoms, or e.g., 1, 2, 3, 4, 5, or 6 heteroatoms, independently selected from the group consisting of nitrogen, oxygen and sulfur, unless specified otherwise. Examples of heterocycloalkyl groups include, but are not limited to, piperidinyl, piperazinyl, pyrrolidinyl, dioxanyl, tetrahydrofuranyl, isoindolinyl, indolinyl, imidazolidinyl, pyrazolidinyl, oxazolidinyl, isoxazolidinyl, triazolidinyl, oxiranyl, azetidinyl, oxetanyl, thietanyl, 1,2,3,6-tetrahydropyridinyl, tetrahydropyranyl, dihydropyranyl, pyranyl, morpholinyl, tetrahydrothiopyranyl, 1,4-diazepanyl, 1,4-oxazepanyl, 2-oxa-5-azabicyclo[2.2.1]heptanyl, 2,5-diazabicyclo[2.2.1] heptanyl, 2-oxa-6-azaspiro[3.3]heptanyl, 2,6-diazaspiro [3.3]heptanyl, 1,4-dioxa-8-azaspiro[4.5]decanyl, 1,4-dioxaspiro[4.5]decanyl, 1-oxaspiro[4.5]decanyl, 1-azaspiro[4.5] decanyl, 3'H-spiro[cyclohexane-1,1'-isobenzofuran]-yl, 7'H-spiro[cyclohexane-1,5'-furo[3,4-b]pyridin]-yl, 3'H-spiro[cyclohexane-1,1'-furo[3,4-c]pyridin]-yl, 3-azabicyclo [3.1.0]hexanyl, 3-azabicyclo[3.1.0]hexan-3-yl, 1,4,5,6-tetrahydropyrrolo[3,4-c]pyrazolyl, 3,4,5,6,7,8-hexahydropyrido[4,3-d]pyrimidinyl, 4,5,6,7-tetrahydro-TH-pyrazolo[3,4-c]pyridinyl, 5,6,7,8-tetrahydropyrido[4,3-d] pyrimidinyl, 2-azaspiro[3.3]heptanyl, 2-methyl-2-azaspiro [3.3]heptanyl, 2-azaspiro[3.5]nonanyl, 2-methyl-2-azaspiro [3.5]nonanyl, 2-azaspiro[4.5]decanyl, 2-methyl-2-azaspiro [4.5]decanyl, 2-oxa-azaspiro[3.4]octanyl, 2-oxa-azaspiro [3.4]octan-6-yl, 5,6-dihydro-4H-cyclopenta[b]thiophenyl, and the like. In the case of multicyclic heterocycloalkyl, only one of the rings in the heterocycloalkyl needs to be non-aromatic (e.g., 4,5,6,7-tetrahydrobenzo[c]isoxazolyl).

As used herein, the term "aryl" includes groups with aromaticity, including "conjugated," or multicyclic systems with one or more aromatic rings and do not contain any heteroatom in the ring structure. The term aryl includes both monovalent species and divalent species. Examples of aryl groups include, but are not limited to, phenyl, biphenyl, naphthyl and the like. Conveniently, an aryl is phenyl.

As used herein, the term "heteroaryl" is intended to include a stable 5-, 6-, or 7-membered monocyclic or 7-, 8-, 9-, 10-, 11- or 12-membered bicyclic aromatic heterocyclic ring which consists of carbon atoms and one or more heteroatoms, e.g., 1 or 1-2 or 1-3 or 1-4 or 1-5 or 1-6 heteroatoms, or e.g., 1, 2, 3, 4, 5, or 6 heteroatoms, independently selected from the group consisting of nitrogen, oxygen and sulfur. The nitrogen atom may be substituted or unsubstituted (i.e., N or NR wherein R is H or other substituents, as defined). The nitrogen and sulfur heteroatoms may optionally be oxidised (i.e., N→O and S(O)$_p$, where p=1 or 2). It is to be noted that total number of S and O atoms in the aromatic heterocycle is not more than 1.

Examples of heteroaryl groups include pyrrole, furan, thiophene, thiazole, isothiazole, imidazole, triazole, tetrazole, pyrazole, oxazole, isoxazole, isothiazole, pyridine, pyrazine, pyridazine, pyrimidine, and the like. Heteroaryl groups can also be fused or bridged with alicyclic or heterocyclic rings, which are not aromatic so as to form a multicyclic system (e.g., 4,5,6,7-tetrahydrobenzo[c]isoxazolyl). In some embodiments, the heteroaryl is thiophenyl or benzothiophenyl. In some embodiments, the heteroaryl is thiophenyl. In some embodiments, the heteroaryl benzothiophenyl.

Furthermore, the terms "aryl" and "heteroaryl" include multicyclic aryl and heteroaryl groups, e.g., tricyclic, bicyclic, e.g., naphthalene, benzoxazole, benzodioxazole, benzothiazole, benzoimidazole, benzothiophene, quinoline, isoquinoline, naphthrydine, indole, benzofuran, purine, benzofuran, deazapurine, indolizine.

The cycloalkyl, heterocycloalkyl, aryl, or heteroaryl ring can be substituted at one or more ring positions (e.g., the ring-forming carbon or heteroatom such as N) with such substituents as described above, for example, alkyl, alkenyl, alkynyl, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl and heteroaryl groups can also be fused or bridged with alicyclic or heterocyclic rings, which are not aromatic so as to form a multicyclic system (e.g., tetralin, methylenedioxyphenyl such as benzo[d][1,3]dioxole-5-yl).

As used herein, the term "substituted," means that any one or more hydrogen atoms on the designated atom is replaced with a selection from the indicated groups, provided that the designated atom's normal valency is not exceeded, and that the substitution results in a stable compound. When a substituent is oxo or keto (i.e., =O), then 2 hydrogen atoms on the atom are replaced. Keto substituents are not present on aromatic moieties. Ring double bonds, as used herein, are double bonds that are formed between two adjacent ring atoms (e.g., C=C, C=N or N=N). "Stable compound" and "stable structure" are meant to indicate a compound that is sufficiently robust to survive isolation to a useful degree of purity from a reaction mixture, and formulation into an efficacious therapeutic agent.

When a bond to a substituent is shown to cross a bond connecting two atoms in a ring, then such substituent may be bonded to any atom in the ring. When a substituent is listed without indicating the atom via which such substituent is bonded to the rest of the compound of a given formula, then such substituent may be bonded via any atom in such formula. Combinations of substituents and/or variables are permissible, but only if such combinations result in stable compounds.

When any variable (e.g., R) occurs more than one time in any constituent or formula for a compound, its definition at each occurrence is independent of its definition at every other occurrence. Thus, for example, if a group is shown to be substituted with 0-2 R moieties, then the group may optionally be substituted with up to two R moieties and R at each occurrence is selected independently from the definition of R. Also, combinations of substituents and/or variables are permissible, but only if such combinations result in stable compounds.

As used herein, the term "hydroxy" or "hydroxyl" includes groups with an —OH or —O$^-$.

As used herein, the term "halo" or "halogen" refers to fluoro, chloro, bromo and iodo.

The term "haloalkyl" or "haloalkoxyl" refers to an alkyl or alkoxyl substituted with one or more halogen atoms.

As used herein, the term "optionally substituted haloalkyl" refers to unsubstituted haloalkyl having designated substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

As used herein, the term "alkoxy" or "alkoxyl" includes substituted and unsubstituted alkyl, alkenyl and alkynyl groups covalently linked to an oxygen atom. Examples of alkoxy groups or alkoxyl radicals include, but are not limited to, methoxy, ethoxy, isopropyloxy, propoxy, butoxy and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy and trichloromethoxy.

As used herein, the expressions "one or more of A, B, or C," "one or more A, B, or C," "one or more of A, B, and C," "one or more A, B, and C," "selected from the group consisting of A, B, and C", "selected from A, B, and C", and the like are used interchangeably and all refer to a selection from a group consisting of A, B, and/or C, i.e., one or more As, one or more Bs, one or more Cs, or any combination thereof, unless indicated otherwise.

It is to be understood that the present disclosure provides methods for the synthesis of the compounds of any of the Formulae described herein. The present disclosure also provides detailed methods for the synthesis of various disclosed compounds of the present disclosure according to the following schemes as well as those shown in the Examples.

It is to be understood that, throughout the description, where compositions are described as having, including, or comprising specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps order for performing certain actions is immaterial so long as the invention remains operable. Moreover, two or more steps or actions can be conducted simultaneously.

It is to be understood that the synthetic processes of the disclosure can tolerate a wide variety of functional groups, therefore various substituted starting materials can be used. The processes generally provide the desired final compound at or near the end of the overall process, although it may be desirable in certain instances to further convert the compound to a pharmaceutically acceptable salt thereof.

It is to be understood that compounds of the present disclosure can be prepared in a variety of ways using commercially available starting materials, compounds known in the literature, or from readily prepared intermediates, by employing standard synthetic methods and procedures either known to those skilled in the art, or which will be apparent to the skilled artisan in light of the teachings herein. Standard synthetic methods and procedures for the preparation of organic molecules and functional group transformations and manipulations can be obtained from the relevant scientific literature or from standard textbooks in the field.

Although not limited to any one or several sources, classic texts such as Smith, M. B., March, J., *March's Advanced Organic Chemistry: Reactions, Mechanisms, and Structure*, 5$^{th}$ edition, John Wiley & Sons: New York, 2001; Greene, T. W., Wuts, P.G.M., *Protective Groups in Organic Synthesis*, 3$^{rd}$ edition, John Wiley & Sons: New York, 1999; R. Larock, *Comprehensive Organic Transformations*, VCH Publishers (1989); L. Fieser and M. Fieser, *Fieser and Fieser's Reagents forganic Synthesis*, John Wiley and Sons (1994); and L. Paquette, ed., *Encyclopedia of Reagents forganic Synthesis*, John Wiley and Sons (1995), incorporated by reference herein, are useful and recognised reference textbooks of organic synthesis known to those in the art One of ordinary skill in the art will note that, during the reaction sequences and synthetic schemes described herein, the order of certain steps may be changed, such as the introduction and removal of protecting groups. One of ordinary skill in the art will recognise that certain groups may require protection from the reaction conditions via the use of protecting groups. Protecting groups may also be used to differentiate similar functional groups in molecules. A list of protecting groups and how to introduce and remove these groups can be found in Greene, T. W., Wuts, P.G.M., *Protective Groups in Organic Synthesis*, 3$^{rd}$ edition, John Wiley & Sons: New York, 1999.

It is to be understood that, unless otherwise stated, any description of a method of treatment or prevention includes use of the compounds to provide such treatment or prevention as is described herein. It is to be further understood, unless otherwise stated, any description of a method of treatment or prevention includes use of the compounds to prepare a medicament to treat or prevent such condition. The treatment or prevention includes treatment or prevention of human or non-human animals including rodents and other disease models.

It is to be understood that, unless otherwise stated, any description of a method of treatment includes use of the compounds to provide such treatment as is described herein. It is to be further understood, unless otherwise stated, any description of a method of treatment includes use of the compounds to prepare a medicament to treat such condition. The treatment includes treatment of human or non-human animals including rodents and other disease models As used herein, the term "subject" is interchangeable with the term "subject in need thereof", both of which refer to a subject having a disease or having an increased risk of developing the disease. A "subject" includes a mammal. The mammal can be e.g., a human or appropriate non-human mammal, such as primate, mouse, rat, dog, cat, cow, horse, goat, camel, sheep or a pig. The subject can also be a bird or fowl. In one embodiment, the mammal is a human. A subject in need thereof can be one who has been previously diagnosed or identified as having a disease or disorder disclosed herein. A subject in need thereof can also be one who is suffering from a disease or disorder disclosed herein. Alternatively, a subject in need thereof can be one who has an increased risk of developing such disease or disorder relative to the population at large (i.e., a subject who is predisposed to developing such disorder relative to the population at large). A subject in need thereof can have a refractory or resistant a disease or disorder disclosed herein (i.e., a disease or disorder disclosed herein that does not respond or has not yet responded to treatment). The subject may be resistant at start of treatment or may become resistant during treatment. In some embodiments, the subject in need thereof received and failed all known effective therapies for a disease or disorder disclosed herein. In some embodiments, the subject in need thereof received at least one prior therapy.

As used herein, the term "treating" or "treat" describes the management and care of a patient for the purpose of combating a disease, condition, or disorder and includes the administration of a compound of the present disclosure, or a pharmaceutically acceptable salt, polymorph or solvate thereof, to alleviate the symptoms or complications of a disease, condition or disorder, or to eliminate the disease, condition or disorder. The term "treat" can also include treatment of a cell in vitro or an animal model. It is to be appreciated that references to "treating" or "treatment" include the alleviation of established symptoms of a condition. "Treating" or "treatment" of a state, disorder or condition therefore includes: (1) preventing or delaying the appearance of clinical symptoms of the state, disorder or condition developing in a human that may be afflicted with or predisposed to the state, disorder or condition but does not yet experience or display clinical or subclinical symptoms of the state, disorder or condition, (2) inhibiting the state, disorder or condition, i.e., arresting, reducing or delaying the development of the disease or a relapse thereof (in case of maintenance treatment) or at least one clinical or subclinical symptom thereof, or (3) relieving or attenuating the disease, i.e., causing regression of the state, disorder or condition or at least one of its clinical or subclinical symptoms.

It is to be understood that a compound of the present disclosure, or a pharmaceutically acceptable salt, polymorph or solvate thereof, can or may also be used to prevent a relevant disease, condition or disorder, or used to identify suitable candidates for such purposes.

As used herein, the term "preventing," "prevent," or "protecting against" describes reducing or eliminating the onset of the symptoms or complications of such disease, condition or disorder.

It is to be understood that one skilled in the art may refer to general reference texts for detailed descriptions of known techniques discussed herein or equivalent techniques. These texts include Ausubel et al., *Current Protocols in Molecular Biology*, John Wiley and Sons, Inc. (2005); Sambrook et al., *Molecular Cloning, A Laboratory Manual* ($3^{rd}$ edition), Cold Spring Harbor Press, Cold Spring Harbor, N.Y. (2000); Coligan et al., *Current Protocols in Immunology*, John Wiley & Sons, N.Y.; Enna et al., *Current Protocols in Pharmacology*, John Wiley & Sons, N.Y.; Fingl et al., *The Pharmacological Basis of Therapeutics* (1975), *Remington's Pharmaceutical Sciences*, Mack Publishing Co., Easton, PA, $18^{th}$ edition (1990). These texts can, of course, also be referred to in making or using an aspect of the disclosure.

It is to be understood that the present disclosure also provides pharmaceutical compositions comprising any compound described herein in combination with at least one pharmaceutically acceptable excipient or carrier.

As used herein, the term "pharmaceutical composition" is a formulation containing the compounds of the present disclosure in a form suitable for administration to a subject. In one embodiment, the pharmaceutical composition is in bulk or in unit dosage form. The unit dosage form is any of a variety of forms, including, for example, a capsule, an IV bag, a tablet, a single pump on an aerosol inhaler or a vial. The quantity of active ingredient (e.g., a formulation of the disclosed compound or salt, hydrate, solvate or isomer thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this disclosure include powders, sprays, ointments, pastes, creams, lotions, gels, solutions, patches and inhalants. In one embodiment, the active compound is mixed under sterile conditions with a pharmaceutically acceptable carrier, and with any preservatives, buffers, or propellants that are required.

As used herein, the term "pharmaceutically acceptable" refers to those compounds, anions, cations, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

It is to be understood that a pharmaceutical composition of the disclosure is formulated to be compatible with its intended route of administration. Examples of routes of administration include parenteral, e.g., intravenous, intradermal, subcutaneous, oral (e.g., ingestion), inhalation, transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

It is to be understood that a compound or pharmaceutical composition of the disclosure can be administered to a subject in many of the well-known methods currently used for chemotherapeutic treatment. For example, a compound of the disclosure may be injected into the blood stream or body cavities or taken orally or applied through the skin with patches. The dose chosen should be sufficient to constitute effective treatment but not so high as to cause unacceptable side effects. The state of the disease condition (e.g., a disease or disorder disclosed herein) and the health of the patient should preferably be closely monitored during and for a reasonable period after treatment.

As used herein, the term "therapeutically effective amount", refers to an amount of a pharmaceutical agent to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician.

As used herein, the term "therapeutically effective amount", refers to an amount of a pharmaceutical agent to treat or ameliorate an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician.

It is to be understood that, for any compound, the therapeutically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{05}$. Pharmaceutical compositions that exhibit large therapeutic indices are preferred. The dosage may vary within this range depending upon the dosage form employed, sensitivity of the patient, and the route of administration.

Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

The pharmaceutical compositions containing active compounds of the present disclosure may be manufactured in a manner that is generally known, e.g., by means of conventional mixing, dissolving, granulating, dragee-making, levigating, emulsifying, encapsulating, entrapping, or lyophilising processes. Pharmaceutical compositions may be formulated in a conventional manner using one or more pharmaceutically acceptable carriers comprising excipients and/or auxiliaries that facilitate processing of the active compounds into preparations that can be used pharmaceutically. Of course, the appropriate formulation is dependent upon the route of administration chosen.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants.

Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol and sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilisation. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible pharmaceutically acceptable carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, orange flavoring.

For administration by inhalation, the compounds are delivered in the form of an aerosol spray from pressured container or dispenser, which contains a suitable propellant, e.g., a gas such as carbon dioxide, or a nebuliser.

For intranasal administration, the compounds are delivered in solution or solid formulation. In some embodiments, the compounds are delivered in solution as a mist, a drip, or a swab. In some embodiments, the compounds are delivered as a powder. In some embodiments, the compound is included in a kit which further includes an intranasal applicator.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The active compounds can be prepared with pharmaceutically acceptable carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the particular therapeutic effect to be achieved.

In therapeutic applications, the dosages of the pharmaceutical compositions used in accordance with the disclosure vary depending on the agent, the age, weight, and clinical condition of the recipient patient, and the experience and judgment of the clinician or practitioner administering the therapy, among other factors affecting the selected dosage. Generally, the dose should be sufficient to result in slowing, and preferably regressing, the symptoms of the disease or disorder disclosed herein and also preferably causing complete regression of the disease or disorder. Dosages can range from about 0.01 mg/kg per day to about 5000 mg/kg per day. An effective amount of a pharmaceutical agent is that which provides an objectively identifiable improvement as noted by the clinician or other qualified observer. Improvement in survival and growth indicates regression. As used herein, the term "dosage effective manner" refers to amount of an active compound to produce the desired biological effect in a subject or cell.

It is to be understood that the pharmaceutical compositions can be included in a container, pack, or dispenser together with instructions for administration.

It is to be understood that, for the compounds of the present disclosure being capable of further forming salts, all of these forms are also contemplated within the scope of the claimed disclosure.

As used herein, the term "pharmaceutically acceptable salts" refer to derivatives of the compounds of the present disclosure wherein the parent compound is modified by making acid or base salts thereof. Examples of pharmaceutically acceptable salts include, but are not limited to, mineral organic acid salts of basic residues such as amines, alkali organic salts of acidic residues such as carboxylic acids, and the like. The pharmaceutically acceptable salts include the conventional non-toxic salts or the quaternary ammonium salts of the parent compound formed, for example, from non-toxic inorganic organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, 1,2-ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicylic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc.

In some embodiments, the pharmaceutically acceptable salt is a sodium salt, a potassium salt, a calcium salt, a magnesium salt, a diethylamine salt, a choline salt, a meglumine salt, a benzathine salt, a tromethamine salt, an ammonia salt, an arginine salt, or a lysine salt.

Other examples of pharmaceutically acceptable salts include hexanoic acid, cyclopentane propionic acid, pyruvic acid, malonic acid, 3-(4-hydroxybenzoyl)benzoic acid, cinnamic acid, 4-chlorobenzenesulfonic acid, 2-naphthalenesulfonic acid, 4-toluenesulfonic acid, camphorsulfonic acid, 4-methylbicyclo-[2.2.2]-oct-2-ene-1-carboxylic acid, 3-phenylpropionic acid, trimethylacetic acid, tertiary butylacetic acid, muconic acid, and the like. The present disclosure also encompasses salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. In the salt form, it is understood that the ratio of the compound to the cation or anion of the salt can be 1:1, or any ratio other than 1:1, e.g., 3:1, 2:1, 1:2, or 1:3.

It is to be understood that all references to pharmaceutically acceptable salts include solvent addition forms (solvates) or crystal forms (polymorphs) as defined herein, of the same salt.

The compounds, or pharmaceutically acceptable salts thereof, are administered orally, nasally, transdermally, pulmonary, inhalationally, buccally, sublingually, intraperitoneally, subcutaneously, intramuscularly, intravenously, rectally, intrapleurally, intrathecally and parenterally. In one embodiment, the compound is administered orally. One skilled in the art will recognise the advantages of certain routes of administration.

The dosage regimen utilising the compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition. An ordinarily skilled physician or veterinarian can readily determine and prescribe the effective amount of the drug required to counter or arrest the progress of the condition.

Techniques for formulation and administration of the disclosed compounds of the disclosure can be found in *Remington: the Science and Practice of Pharmacy*, 19$^{th}$ edition, Mack Publishing Co., Easton, PA (1995). In an embodiment, the compounds described herein, and the pharmaceutically acceptable salts thereof, are used in pharmaceutical preparations in combination with a pharmaceutically acceptable carrier or diluent. Suitable pharmaceutically acceptable carriers include inert solid fillers or diluents and sterile aqueous organic solutions. The compounds will be present in such pharmaceutical compositions in amounts sufficient to provide the desired dosage amount in the range described herein.

All percentages and ratios used herein, unless otherwise indicated, are by weight. Other features and advantages of the present disclosure are apparent from the different examples. The provided examples illustrate different components and methodology useful in practicing the present disclosure. The examples do not limit the claimed disclosure. Based on the present disclosure the skilled artisan can identify and employ other components and methodology useful for practicing the present disclosure.

In the synthetic schemes described herein, compounds may be drawn with one particular configuration for simplicity. Such particular configurations are not to be construed as limiting the disclosure to one or another isomer, tautomer, regioisomer or stereoisomer, nor does it exclude mixtures of isomers, tautomers, regioisomers or stereoisomers; however, it will be understood that a given isomer, tautomer, regioisomer or stereoisomer may have a higher level of activity than another isomer, tautomer, regioisomer or stereoisomer.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

EXAMPLES

Example 1. Computational-Based Modeling

BI-D1870, LJH685, LJI308, purines, and pyrrolopyrimidines were docked into the ATP-binding site of the NTKD of RSK2 (PDB: 4NUS) crystal structure, using the Glide module within Schrödinger (Release 2020-3, Schrödinger LLC, New York, NY). Prior to docking, the water molecules were removed, and the proteins were prepared by assigning bond orders, adding hydrogens, and repairing any side chains or missing amino acid sequences. To complete protein preparation a restrained minimization of the protein structure was performed using the default constraint of 0.30 Å RMSD and the OPLS_2005 force field. The prepared proteins were subjected to SiteMap analysis, that identified the ATP-binding site in the NTKD and docking grids were generated using Receptor Grid Generation. BI-D1870 and analogs were prepared using LigPrep by generating possible states at the target pH 7.0 using Epik and minimized by applying the OPLS_2005 force field. Molecular docking simulations were performed using the Glide ligand docking module in XP (extra precision) mode and included post-docking minimization. The docked structures of BI-D1870, LJH685, and LJI308 in the ATP-binding site of the RSK NTKD were used as the basis for the design of candidate RSK inhibitors, with the aim of introducing substitutions to test the importance of interactions with residues in the ATP-binding site. The synthesized purines and pyrrolopyrimidines that demonstrated potent RSK inhibition in the TR-FRET kinase activity assay were prepared and docked in the RSK crystal structure in order to identify the critical interactions that resulted in RSK inhibition.

The Phase module was used for pharmacophore modeling. Previously prepared and docked BI-D1870, LJH685, LJI308, purines, and pyrrolopyrimidines were imported with their respective $IC_{50}$ values, determined by the recombinant kinase TR-FRET assay for pharmacophore hypothesis generation. Compounds with $IC_{50}$ values accurately determined by the recombinant kinase assay were defined as active. Compounds for which the recombinant kinase assay could not accurately determine $IC_{50}$ values against RSK2 were defined as inactive. The highest-ranking docked conformation of each compound from the previously performed Glide docking was used to compose a set of pre-aligned ligands. Default values and feature settings were used for hypothesis generation and the Phase hypo scoring function was used to score and rank compounds and hypotheses. Phase calculated vector, volume, site scores, survival scores, and survival activities to score and rank 20 possible feature combinations able to produce common pharmacophores. The highest-ranking hypothesis (HHRR_1) used A1-13 (the most active molecule in the recombinant kinase assay) as the reference ligand for hypothesis generation.

Example 2. Synthesis of Exemplary Compounds

All melting points (MP) were determined using a Mettler Toledo M540 melting point apparatus. $^1$H and $^{13}$C nuclear magnetic resonance (NMR) spectra were obtained as solutions in deuterated solvents DMSO-$d_6$ or CDCl$_3$ using a 400 MHz Bruker Avance III 400 spectrometer. Chemical shifts (δ) are reported in parts per million and the spin-multiplicity abbreviated as: s (singlet), d (doublet), t (triplet), q (quartet), quin (quintet), m (multiplet), bs (broad singlet), dd (doublet of doublets), or dt (doublet of triplets) with coupling constants (J) given in Hertz (Hz). High-resolution mass spectrometry (HRMS) was performed using an Agilent 6520 tandem quadrupole-time of flight (Q-TOF) mass spectrometer coupled to an electrospray ionization source. Spray was induced with a capillary voltage of 4000V and the fragmentor voltage was 200V. Data was acquired over a range of m/z 50-1700. Fourier Transform Infrared (FTIR) spectra were obtained using a Bruker Alpha Platinum-ATR as a neat sample.

General Procedures

General Procedure A: A solution of necessary aniline (1.1-2 equiv., as indicated) in DCM or EtOH (0.5-2 M) was added drop-wise to a solution of 2,4-dichloro-5-nitropyrimidine (1.0 equiv.) in DCM (0.5-1 M) stirring at −15° C. The reaction was stirred for 15 minutes, concentrated in vacuo and purified via gel chromatography, if necessary, to afford the desired compound.

General Procedure B: To a solution of nitropyrimidine precursor (1.0 equiv.) in EtOH (0.1 M) was added tin(II) chloride (4 equiv.). The reaction was heated under reflux for 1.5 h before the solvent was removed in vacuo. The resulting residue was dissolved in EtOAc:THF (1:1, 20 mL/mmol) and a saturated aqueous solution of NaHCO$_3$ was added until the aqueous phase reached pH 9-10. The resulting precipitate was removed via filtration and the organic extracts were collected, washed with brine (20 mL/mmol), and extracted with EtOAc:THF (1:1; 3×15 mL/mmol). The combined organic extracts were dried (MgSO$_4$) and concentrated in vacuo, and the crude residue was purified via silica gel chromatography to afford the desired compound.

General Procedure C: The relevant diaminopyrimidine (1.0 equiv.), triethyl orthoformate (2.5 equiv.) and TFA (0.1 equiv.) were taken up in TFE (0.2 M) and heated under microwave irradiation conditions at 140° C. for 1.5 hours before being concentrated in vacuo.

The residue was resuspended in EtOAc:THF (1:1, 20 mL/mmol), washed with saturated NaHCO$_3$ solution (20 mL/mmol), and the aqueous phase was further extracted with EtOAc:THF (1:1, 3×15 mL/mmol). The combined organic extracts were washed with brine, dried (MgSO$_4$) and concentrated in vacuo. The resultant residue was purified via silica gel chromatography to afford the desired compound.

General Procedure D: The relevant heterocycle (1.0 equiv.), amino-difluorophenol (2.0-2.5 equiv., as indicated) and TFA (2.0-7.0 equiv.) were taken up in TFE (0.1 M) and heated under microwave irradiation conditions at 140° C. for 1.5 hours (unless otherwise indicated) before being concentrated in vacuo. The residue was resuspended in EtOAc:THF (1:1, 20 mL/mmol), washed with saturated NaHCO$_3$ solution (20 mL/mmol), and the aqueous phase was further extracted with EtOAc:THF (1:1, 3×15 mL/mmol). The combined organic extracts were washed with brine, dried (MgSO$_4$) and concentrated in vacuo. The resultant residue was purified via silica gel chromatography and/or triturated as specified to afford the desired compound.

General Procedure E: The relevant benzyl-protected difluorophenol purine (1.0 equiv.) was taken up in DMF (0.05 M) prior to the addition of ammonium formate (5.0 equiv.) and Pd/C (20% w/w). The reaction mixture was heated under microwave irradiation conditions at 80° C. for 15 minutes, filtered, washed with MeOH (10 mL/mmol) and the filtrate was concentrated in vacuo. The resultant residue was purified via silica gel chromatography and triturated with MeOH to afford the desired compound.

General Procedure F: To a stirring solution containing 2-chloro-7H-pyrrolo[2,3-d]pyrimidine (1 equiv.), the necessary boronic acid (1.3 equiv.) and copper acetate (1.1 equiv.) in CHCl$_3$ (0.1 M) was added pyridine (7.5 equiv.). The reaction was stirred for 3 days before being concentrated in vacuo. The resultant residue was purified via column chromatography to afford the desired compound.

Synthesis of Compounds

6-Chloro-2-fluoro-9H-purine. 2-Amino-6-cloropurine (1.00 g, 5.90 mmol) was taken up in HBF$_4$ (20 mL, 48 wt. % in H$_2$O, 0.3M) and cooled to 0° C. A solution of sodium nitrite (0.84 g, 11.8 mmol) in water (12 mL, 1M) was added dropwise over 30 minutes. Upon completion of addition the reaction mixture was stirred at RT for 15 min, after which the solution was cooled to 0° C. and neutralized with 6M NaOH. The product was then extracted with EtOAc (3×15 mL) and the combined organic extracts were dried (MgSO$_4$) and concentrated in vacuo to afford the desired compound as a yellow solid (0.83 g, 4.81 mmol, 82%). Rf 0.53 (17:3 DCM:MeOH); M.p. 169-173° C. (Lit.=171-173° C.); IR (cm$^{-1}$) 3071, 2953, 2922, 2849, 2786, 1616, 1582; $^1$H NMR (400 MHz, DMSO-$d_6$) 8.71 (1H, s, H-8), 14.08 (1H, bs, NH); $^{13}$C NMR (100 MHz, DMSO-$d_6$) 155.7 (Ar—C), 157.8 (Ar—C). HRMS cal. C$_5$HClFN$_4$ (ES−) m/z 170.987377 [M−H]$^-$, found 170.984486.

2-Fluoro-9H-purine. Palladium hydroxide (0.70 g, 20% wt./C) and ammonium formate (0.77 g, 12.2 mmol) were added to a solution of chloro-purine 62 (0.70 g, 4.06 mmol) in MeOH (100 ml, 0.04 M). The reaction was heated under reflux for 2 hours before the catalyst was removed via filtration over Celite. The product was concentrated in vacuo and purified via silica gel chromatography (9:1 DCM:MeOH) to afford the desired compound as a as a white solid (0.33 g, 2.42 mmol, 60%). Rf 0.32 (9:1 DCM:MeOH); M.p. 222-226° C. (Lit.=219° C.); IR (cm$^{-1}$) 3132, 3073, 3030, 2973, 2926, 2850, 2822, 2641, 2606, 1891, 1621, 1570; $^1$H NMR (400 MHz, DMSO-$d_6$) 8.68 (1H, s, H-8), 9.03 (1H, s, H-6), 13.59 (1H, br s, NH); $^{13}$C NMR (100 MHz, DMSO-$d_6$) 147.6 (Ar—C), 148.4 (Ar—C), 157.5 (Ar—C), 159.6 (Ar—C). HRMS cal. C$_5$H$_4$FN$_4$ (ES+) m/z 139.041999 [M+H]$^+$, found 139.043025.

4-((9H-Purin-2-yl)amino)-2,6-difluorophenol (Compound No. A1-1). Purine (79 mg, 0.543 mmol), aniline (158 mg, 1.09 mmol) and TFA (208 µL, 2.72 mmol) were taken up in TFE (5 mL) and reacted according to the described General Procedure D. Purification via silica gel chromatography (9:1 DCM:MeOH) and subsequent trituration with MeOH afforded the target compound as a brown solid (61.3 mg, 0.23 mmol, 43%). Rf 0.33 (9:1 DCM:MeOH); M. p. 250-251° C.; IR (cm$^{-1}$) 3383, 3259, 1639, 1594, 1559, 1529, 1505; $^1$H NMR (400 MHz, DMSO-$d_6$) 7.57 (2H, d, J=10.4 Hz, H-3'/5'), 8.22 (bs, OH), 8.82 (H-6), 9.53 (C$_2$—NH), 9.59 (H-8), 12.99 (H8-NH); $^{13}$C NMR (100 MHz, DMSO-$d_6$) 102.1 (d, J$_{CF}$=28.5 Hz, Ar—C), 127.4 (dd, J$_{CF}$=17.1, 15.7 Hz, Ar—C), 133.5 (dd, J$_{CF}$=13.5, 12.2 Hz, Ar—C), 152.8

(dd, $J_{CF}$=237.5, 9.0 Hz, Ar—C), 156.6 (Ar—C). HRMS cal. $C_{11}H_8F_2N_5O$ (ES+) m/z 264.069691 [M+H]$^+$, found 264.060232.

2-Chloro-N-isopentyl-5-nitropyrimidin-4-amine. Isopentylamine (120 µL, 1.04 mmol, 2.0 equiv.) was taken up in EtOH (0.5 mL, 2M) and reacted with a solution of 2,4-dichloro-5-nitropyrimidine (102 mg, 0.52 mmol) in DCM (0.8 mL, 0.7 M) according to the described General Procedure A. Purification via silica gel chromatography (9:1 Hexanes:EtOAc) afforded the target compound as a yellow solid (0.35 g, 1.44 mmol, 80%). Rf 0.41 (4:1 Hexanes:EtOAc); M.p. 55-57° C.; IR (cm$^{-1}$) 3349, 3046, 2953, 2867, 1604, 1567, 1509; $^1$H NMR (400 MHz, DMSO-d$_6$) 0.92 (6H, d, J=6.5 Hz, CH(CH$_3$)$_2$, 1.43-1.54 (2H, m, NHCH$_2$CH$_2$), 1.54-1.68 (1H, m, CH(CH$_3$)$_2$, 3.55 (2H, dt, J=7.0, 6.9 Hz, NHCH$_2$CH$_2$), 9.00 (1H, s, H-6), 9.05-9.17 (1H, m, NH); $^{13}$C NMR (100 MHz, DMSO-d$_6$) 22.8 (CH(CH$_3$)$_2$), 25.7 (CH(CH$_3$)$_2$), 37.7 (NHCH$_2$CH$_2$), 39.4 (NHCH$_2$CH$_2$), 127.6 (Ar—C), 155.3 (Ar—C), 157.7 (Ar—C), 162.8 (Ar—C). HRMS cal. $C_9H_{13}ClN_4O_2$ (ES+) m/z 244.072704 [M+H]$^+$, found 244.078767.

2-Chloro-N4-isopentylpyrimidine-4,5-diamine. Nitropyrimidine (0.30 g, 1.23 mmol) and tin(II) chloride (0.96 g, 4.92 mmol) were taken up in EtOH (12 mL) and reacted according to General Procedure B. Purification via silica gel chromatography (24:1 DCM:MeOH) afforded the target compound as a brown solid (0.23 g, 1.07 mmol, 89%). Rf 0.2 (24:1 DCM:MeOH); M.p. 105-107° C.; IR (cm$^{-1}$) 3433, 3357, 2950, 2869, 1650, 1585; $^1$H NMR (400 MHz, DMSO-d$_6$) 0.91 (6H, d, J=6.6 Hz, CH(CH$_3$)$_2$, 1.45 (2H, dt, J=8.2, 7.0 Hz, NHCH$_2$CH$_2$), 1.57-1.73 (1H, m, CH(CH$_3$)$_2$, 3.26-3.47 (2H, m, NHCH$_2$CH$_2$), 4.88 (2H, s, NH$_2$), 6.76 (1H, t, J=5.6 Hz, NH), 7.36 (1H, s, H-6); $^{13}$C NMR (100 MHz, DMSO-d$_6$) 22.9 (CH(CH$_3$)$_2$), 25.7 (CH(CH$_3$)$_2$), 38.0 (NHCH$_2$CH$_2$), 39.1 (NHCH$_2$CH$_2$), 127.4 (Ar—C), 136.0 (Ar—C), 147.5 (Ar—C), 154.1 (Ar—C). HRMS cal. $C_9H_{15}ClN_4$ (ES+) m/z 214.098523 [M+H]$^+$, found 214.106381.

2-chloro-9-isopentyl-9H-purine. Diaminopyrimidine (0.22 g, 1.03 mmol), triethyl orthoformate (0.43 mL, 2.58 mmol) and TFA (8 µL, 0.10 mmol) were taken up in TFE (5 mL) and reacted according to General Procedure C. Purification via silica gel chromatography (1:1 Hexanes:EtOAc) afforded the target compound as a yellow oil (0.20 g, 0.91 mmol, 88%). Rf 0.56 (19:1 DCM:MeOH); IR (cm$^{-1}$) 3083, 2955, 2873, 1582, 1506; $^1$H NMR (400 MHz, DMSO-d$_6$) 0.93 (6H, d, J=6.6 Hz, CH(CH$_3$)$_2$, 1.13-1.61 (1H, m, CH(CH$_3$)$_2$, 1.75 (2H, dt, J=8.1, 7.4 Hz, NHCH$_2$CH$_2$), 4.26 (2H, t, J=8.1 Hz, NHCH$_2$CH$_2$), 8.71 (1H, s, H-8), 9.08 (1H, s, H-6); $^{13}$C NMR (100 MHz, DMSO-d$_6$) 22.6 (CH(CH$_3$)$_2$), 25.6 (CH(CH$_3$)$_2$), 38.2 (NHCH$_2$CH$_2$), 42.2 (NHCH$_2$CH$_2$), 133.5 (Ar—C), 148.6 (Ar—C), 150.2 (Ar—C), 153.1 (Ar—C), 153.6 (Ar—C). HRMS cal. $C_{10}H_{13}ClN_4$ (ES+) m/z 224.082874 [M+H]$^+$, found 224.08914.

2,6-Difluoro-4-((9-isopentyl-9H-purin-2-yl)amino)phenol (Compound No. A1-2). Purine (81.5 mg, 0.33 mmol), aniline (98.5 mg, 0.67 mmol) and TFA (128 µL, 1.67 mmol) were taken up in TFE (3.3 mL) and reacted according to General Procedure D. Purification via silica gel chromatography (4:1 DCM:MeOH) afforded the target compound as a brown solid (56.4 mg, 0.17 mmol, 47%). Rf 0.23 (19:1 DCM:MeOH); M.p. 203-205° C.; IR (cm$^{-1}$) 3258, 3032, 2950, 1606, 1516; $^1$H NMR (400 MHz, DMSO-d$_6$) 0.97 (6H, d, J=6.7 Hz, CH(CH$_3$)$_2$, 1.48-1.64 (1H, m, CH(CH$_3$)$_2$, 1.78 (2H, dt, J=7.6, 7.2 Hz, NHCH$_2$CH$_2$), 4.20 (2H, t, J=7.6 Hz, NHCH$_2$CH$_2$), 7.60 (2H, d, J=10.1 Hz, H-3'/5'), 8.29 (1H, s, H-8), 8.82 (1H, s, H-6), 9.51 (1H, s, NH), 9.72 (1H, s, OH); $^{13}$C NMR (100 MHz, DMSO-d$_6$) 22.6 (CH(CH$_3$)$_2$), 25.7 (CH(CH$_3$)$_2$), 38.4 (NHCH$_2$CH$_2$), 41.7 (NHCH$_2$CH$_2$), 102.2 (d, $J_{CF}$=27.5 Hz, Ar—C), 127.5 (dd, $J_{CF}$=17.0, 16.5 Hz, Ar—C), 128.6 (Ar—C), 133.3 (dd, $J_{CF}$=12.9, 12.6 Hz, Ar—C), 144.6 (Ar—C), 149.5 (Ar—C), 152.5 (Ar—C), 152.7 (dd, $J_{CF}$=238.2, 9.0 Hz, Ar—C), 156.3 (Ar—C). HRMS cal. $C_{16}H_{17}F_2N_5O$ (ES+) m/z 333.140115 [M+H]$^+$, found 333.147531.

2-Chloro-N-(4-morpholinophenyl)-5-nitropyrimidin-4-amine. 4-Morpholinoaniline (0.89 g, 5.16 mmol, 2.0 equiv.) was taken up in DCM (2.6 mL, 2 M) and reacted with a solution of 2,4-dichloro-5-nitropyrimidine (0.52 g, 2.58 mmol) in DCM (3.7 mL, 0.7 M) according to the described General Procedure A. Purification via silica gel chromatography (7:3 Hexanes:EtOAc) afforded the target compound as a brown solid (0.77 g, 2.29 mmol, 89%). Rf 0.32 (2:1 Hexanes:EtOAc); M.p. 184-187° C.; IR (cm$^{-1}$) 3289, 2948, 2836, 1618, 1576, 1506; $^1$H NMR (400 MHz, DMSO-d$_6$) 3.15 (4H, t, J=4.8 Hz, N(CH$_2$CH$_2$)$_2$O), 3.75 (4H, t, J=4.8 Hz, N(CH$_2$CH$_2$)$_2$O), 7.00 (2H, d, J=8.9 Hz, H-3"/5"), 7.38 (2H, d, J=8.9 Hz, H-2"/6"), 9.11 (1H, s, H-6), 10.33 (1H, s, NH); $^{13}$C NMR (100 MHz, DMSO-d$_6$) 48.8 (NCH$_2$CH$_2$O), 66.5 (NCH$_2$CH$_2$O), 115.4 (Ar—C), 126.0 (Ar—C), 128.0 (Ar—C), 128.2 (Ar—C), 149.6 (Ar—C), 154.2 (Ar—C), 158.1 (Ar—C), 162.5 (Ar—C). HRMS cal. $C_{14}H_{14}ClN_5O_3$ (ES+) m/z 335.078515 [M+H]$^+$, found 335.083699.

4.2.9 2-Chloro-N4-(4-morpholinophenyl)pyrimidine-4,5-diamine. Nitropyrimidine (97.7 mg, 0.30 mmol) and tin(II) chloride (0.25 g, 1.20 mmol) were taken up in EtOH (3 mL) and reacted according to General Procedure B. Purification via silica gel chromatography (24:1 DCM:MeOH) afforded the target compound as a brown solid (88.1 mg, 0.29 mmol, 99%). Rf 0.19 (24:1 DCM:MeOH); M.p. 118-121° C.; IR (cm$^{-1}$) 3324, 2916, 2855, 1597, 1570, 1508; $^1$H NMR (400 MHz, DMSO-d$_6$) 3.08 (4H, m, N(CH$_2$CH$_2$)$_2$O), 3.74 (4H, m, N(CH$_2$CH$_2$)$_2$O), 5.19 (2H, s, NH$_2$), 6.95 (2H, d, J=7.0 Hz, H-3"/5"), 7.50 (2H, d, J=7.0 Hz, H-2"/6"), 7.57 (1H, s, H-6), 8.47 (1H, s, NH); $^{13}$C NMR (100 MHz, DMSO-d$_6$) 49.3 (NCH$_2$CH$_2$O), 66.6 (NCH$_2$CH$_2$O), 115.9 (Ar—C), 122.6 (Ar—C), 128.1 (Ar—C), 131.5 (Ar—C), 138.1 (Ar—C), 146.6 (Ar—C), 147.8 (Ar—C), 151.2 (Ar—C), 162.5 (Ar—C). HRMS cal. $C_{14}H_{16}ClN_5O$ (ES+) m/z 305.104336 [M+H]$^+$, found 305.112602.

4-(4-(2-Chloro-9H-purin-9-yl)phenyl)morpholine. Diaminopyrimidine (0.11 g, 0.33 mmol), triethyl orthoformate (0.14 mL, 0.82 mmol) and TFA (3 µL, 0.03 mmol) were taken up in TFE (1.6 mL) and reacted according to General Procedure C. Purification via silica gel chromatography (4:1 DCM:MeOH) afforded the target compound as a brown solid (98.0 mg, 0.31 mmol, 95%). Rf 0.58 (19:1 DCM MeOH); M.p. 195-197° C.; IR (cm$^{-1}$) 3107, 1613, 1595, 1560, 1520; $^1$H NMR (400 MHz, DMSO-d$_6$) 3.22 (4H, t, J=4.7 Hz, N(CH$_2$CH$_2$)$_2$O), 3.78 (4H, t, J=4.7 Hz, N(CH$_2$CH$_2$)$_2$O), 7.17 (2H, d, J=8.5 Hz, H-3"/5"), 7.64 (2H, d, J=8.5 Hz, H-2"/6"), 8.94 (1H, s, H-8), 9.19 (1H, s, H-6); $^{13}$C NMR (100 MHz, DMSO-d$_6$) δ5.4 (NCH$_2$CH$_2$O), 66.4 (NCH$_2$CH$_2$O), 115.8 (Ar—C), 125.3 (Ar—C), 125.3 (Ar—C), 133.9 (Ar—C), 147.7 (Ar—C), 150.8 (Ar—C), 151.5 (Ar—C), 153.2 (Ar—C), 153.7 (Ar—C). HRMS cal. $C_{15}H_{14}ClN_5O$ (ES+) m/z 315.088686 [M+H]$^+$, found 315.096302.

2,6-Difluoro-4-((9-(4-morpholinophenyl)-9H-purin-2-yl)amino)phenol (Compound No. A1-3). Purine (76.9 mg, 0.24 mmol), aniline (69.5 mg, 0.48 mmol) and TFA (136 µL, 1.19 mmol) were taken up in TFE (2.4 mL) and reacted according to General Procedure D. Purification via silica gel chromatography (19:1 DCM:MeOH) afforded the target compound as a brown solid (30.1 mg, 0.07 mmol, 29%). Rf 0.24 (19:1 DCM:MeOH); M.p. 284-288° C.; IR (cm$^{-1}$) 3260, 3095, 2963, 1610, 1524; $^1$H NMR (400 MHz, DMSO-d$_6$) 3.19 (4H, t, J=4.8 Hz, N(CH$_2$CH$_2$)$_2$O), 3.78 (4H, t, J=4.8 Hz, N(CH$_2$CH$_2$)$_2$O), 7.13 (2H, d, J=8.4 Hz, H-3"/5"), 7.56 (2H, d, J=10.1 Hz, H-3'/5'), 7.70 (2H, d, J=8.4 Hz, H-2"/6"), 8.55 (1H, s, H-8), 8.93 (1H, s, H-6), 9.52 (1H, s, NH), 9.77 (1H, s, OH); $^{13}$C NMR (100 MHz, DMSO-d$_6$) 48.7 (NCH$_2$CH$_2$O), 66.5 (NCH$_2$CH$_2$O), 102.4 (d, J$_{CF}$=27.7 Hz, Ar—C), 115.8 (Ar—C), 124.8 (Ar—C), 126.4 (Ar—C), 127.6 (dd, J$_{CF}$=16.9, 16.4 Hz, Ar—C), 128.8 (Ar—C), 133.1 (dd, J$_{CF}$=14.1, 13.5 Hz, Ar—C), 143.4 (Ar—C), 150.0 (Ar—C), 151.0 (Ar—C), 152.2 (Ar—C), 152.7 (dd, J$_{CF}$=238.8, 7.9 Hz, Ar—C), 156.7 (Ar—C). HRMS cal. C$_{21}$H$_{18}$F$_2$N$_6$O$_2$ (ES+) m/z 424.145930 [M+H]$^+$, found 424.15231.

N-(4-(Benzyloxy)phenyl)-2-chloro-5-nitropyrimidin-4-amine. 4-(Benzyloxy)aniline (0.47 g, 2.33 mmol, 1.5 equiv.) was taken up in DCM (2.3 mL, 1 M) and reacted with a solution of 2,4-dichloro-5-nitropyrimidine (0.31 g, 1.55 mmol) in DCM (3.1 mL, 0.5 M) according to the described General Procedure A. Purification via silica gel chromatography (9:1 Hexanes:EtOAc) afforded the target compound as an orange solid (0.46 g, 1.29 mmol, 83%). Rf 0.37 (4:1 Hexanes:EtOAc); M.p. 134-136° C.; IR (cm$^{-1}$) 3322, 1575, 1499; $^1$H NMR (400 MHz, DMSO-d$_6$) 5.14 (2H, s, OCH$_2$), 7.08 (2H, d, J=8.8 Hz, H-3"/5"), 7.29-7.54 (7H, m, H-2"/6", H-2'''/6''', H-3'''/5''', H-4'''), 9.12 (1H, s, H-6), 10.37 (1H, s, NH); $^{13}$C NMR (100 MHz, DMSO-d$_6$) δ69.9 (OCH$_2$), 115.3 (Ar—C), 126.8 (Ar—C), 128.1 (Ar—C), 128.2 (Ar—C), 128.4 (Ar—C), 128.9 (Ar—C), 129.6 (Ar—C), 137.4 (Ar—C), 154.4 (Ar—C), 157.1 (Ar—C), 158.0 (Ar—C), 162.5 (Ar—C). HRMS cal. C$_{17}$H$_{13}$ClN$_4$O$_3$ (ES+) m/z 356.067618 [M+H]$^+$, found 356.074017.

N4-(4-(Benzyloxy)phenyl)-2-chloropyrimidine-4,5-diamine. Nitropyrimidine (0.40 g, 1.12 mmol) and tin(II) chloride (0.85 g, 4.52 mmol) were taken up in EtOH (12 mL) and reacted according to General Procedure B. Purification via silica gel chromatography (10:1 DCM:MeOH) afforded the target compound as a purple oil (0.43 g, 1.32 mmol, 93%). Rf 0.33 (97:3 DCM:MeOH); M.p. 142-145° C.; IR (cm$^{-1}$) 3340, 3259, 3157, 1652, 1610, 1568, 1502; $^1$H NMR (400 MHz, DMSO-d$_6$) 5.10 (2H, s, OCH$_2$), 5.21 (2H, bs, NH$_2$), 7.02 (2H, d, J=8.9 Hz, H-3"/5"), 7.29-7.51 (5H, m, H-2'''/6''', H-3'''/5''', H-4'''), 7.54 (2H, d, J=8.9 Hz, H-2"/6"), 7.60 (1H, s, H-6), 8.52 (1H, s, NH); $^{13}$C NMR (100 MHz, DMSO-d$_6$) δ69.9 (OCH$_2$), 115.4 (Ar—C), 122.9 (Ar—C), 128.2 (Ar—C), 128.3 (Ar—C), 128.9 (Ar—C), 132.7 (Ar—C), 137.7 (Ar—C), 138.3 (Ar—C), 146.5 (Ar—C), 151.1 (Ar—C), 154.5 (Ar—C). HRMS cal. C$_{17}$H$_{15}$ClN$_4$O (ES+) m/z 326.093438 [M+H]$^+$, found 326.100746.

9-(4-(Benzyloxy)phenyl)-2-chloro-9H-purine. Diaminopyrimidine (0.34 g, 1.05 mmol), triethyl orthoformate (0.44 mL, 2.63 mmol) and TFA (8 μL, 0.11 mmol) were taken up in TFE (5 mL) and reacted according to General Procedure C. Purification via silica gel chromatography (3:2 Hexanes: EtOAc) afforded the target compound as a brown solid (0.32 g, 0.96 mmol, 91%). Rf 0.60 (97:3 DCM:MeOH); M.p. 152-154° C.; IR (cm$^{-1}$) 3133, 3088, 3023, 2930, 2870, 1728, 1589, 1513; $^1$H NMR (400 MHz, DMSO-d$_6$) 5.22 (2H, s, OCH$_2$), 7.27 (2H, d, J=9.0 Hz, H-3"/5"), 7.32-7.55 (5H, m, H-2'''/6''', H-3'''/5''', H-4'''), 7.73 (2H, d, J=9.0 Hz, H-2"/6"), 8.96 (1H, s, H-8), 9.20 (1H, s, H-6); $^{13}$C NMR (100 MHz, DMSO-d$_6$) 70.1 (OCH$_2$), 116.2 (Ar—C), 126.0 (Ar—C), 127.1 (Ar—C), 128.2 (Ar—C), 128.4 (Ar—C), 129.0 (Ar—C), 133.9 (Ar—C), 137.2 (Ar—C), 147.7 (Ar—C), 150.8 (Ar—C), 153.2 (Ar—C), 153.7 (Ar—C), 158.7 (Ar—C). HRMS cal. C$_{18}$H$_{13}$ClN$_4$O (ES+) m/z 336.0777887 [M+H]$^+$, found 336.083129.

4-((9-(4-(Benzyloxy)phenyl)-9H-purin-2-yl)amino)-2,6-difluorophenol (Compound No. A1-9). Purine (0.20 g, 0.59 mmol), aniline (0.27 g, 1.78 mmol) and TFA (0.2 mL, 2.97 mmol) were taken up in TFE (4.8 mL) and reacted according to General Procedure D. Purification via silica gel chromatography (19:1 DCM:MeOH) afforded the target compound as a brown solid (78 mg, 0.18 mmol, 30%). Rf 0.28 (19:1 DCM:MeOH); M.p. 228-230° C.; IR (cm$^{-1}$) 3124, 1610, 1589, 1516; $^1$H NMR (400 MHz, DMSO-d$_6$) 5.22 (2H, s, OCH$_2$), 7.24 (2H, d, J=8.8 Hz, H-3"/5"), 7.31-7.62 (7H, m, H3'/5', H-2"/6''', H-3'''/5''', H-4'''), 7.79 (2H, d, J=8.8 Hz, H-2"/6"), 8.57 (1H, s, H-8), 8.94 (1H, s, H-6), 9.53 (1H, s, NH), 9.77 (1H, s, OH); $^{13}$C NMR (100 MHz, DMSO-d$_6$) 70.0 (OCH$_2$), 102.4 (d, J$_{CF}$=29.5 Hz, Ar—C), 116.0 (Ar—C), 125.5 (Ar—C), 127.7 (Ar—C), 128.1 (Ar—C), 128.2 (Ar—C), 128.4 (Ar—C), 128.8 (Ar—C), 129.0 (Ar—C), 137.3 (Ar—C), 143.5 (Ar—C), 150.0 (Ar—C), 152.3 (Ar—C), 152.7 (dd, J$_{CF}$=237.8, 9.1 Hz, Ar—C), 156.7 (Ar—C), 158.2 (Ar—C). HRMS cal. C$_{24}$H$_{17}$F$_2$N$_5$O$_2$ (ES+) m/z 445.13503 [M+H]$^+$, found 445.140838.

42,6-Difluoro-4-((9-(4-hydroxyphenyl)-9H-purin-2-yl) amino)phenol (Compound No. A1-11). Benzyl-protected purine (77.0 mg, 0.17 mmol), ammonium formate (56.8 mg, 0.87 mmol) and Pd/C (18.0 mg, 20% w/w) were reacted in DMF (3.5 mL) according to General Procedure E. Purification via silica gel chromatography (3:7 DCM:MeOH) followed by subsequent trituration with MeOH afforded the target compound as a brown solid (43 mg, 0.12 mmol, 70%). Rf 0.29 (9:1 DCM:MeOH); M.p.>300° C.; IR (cm$^{-1}$) 3106, 1735, 1605, 1519; $^1$H NMR (400 MHz, DMSO-d$_6$) 6.97 (2H, d, J=8.8 Hz, H-3"/5"), 7.54 (2H, d, J=10.1 Hz, H-3'/5'), 7.65 (2H, d, J=8.8 Hz, H-2"/6"), 8.53 (1H, s, H-8), 8.93 (1H, s, H-6), 9.51 (1H, s, NH), 9.76 (1H, s, OH); 9.87 (1H, s, benzyl-OH); $^{13}$C NMR (100 MHz, DMSO-d$_6$) 102.4 (d, J$_{CF}$=28.1 Hz, Ar—C), 116.3 (Ar—C), 125.5 (Ar—C), 126.4 (Ar—C), 127.7 (Ar—C), 128.7 (Ar—C), 133.0 (Ar—C), 143.5 (Ar—C), 150.0 (Ar—C), 152.2 (Ar—C), 152.7 (dd, J$_{CF}$=237.6, 9.1 Hz, Ar—C), 156.7 (Ar—C), 157.5 (Ar—C). C$_{17}$H$_{11}$F$_2$N$_5$O$_2$ (ES+) m/z 355.088080 [M+H]$^+$, found 355.096407.

N-(3-(Benzyloxy)phenyl)-2-chloro-5-nitropyrimidin-4-amine. 3-(Benzyloxy)aniline (0.47 g, 2.33 mmol, 1.5 equiv.) was taken up in DCM (2.3 mL, 1 M) and reacted with a solution of 2,4-dichloro-5-nitropyrimidine (0.31 g, 1.55 mmol) in DCM (3.1 mL, 0.5 M) according to the described General Procedure A. Purification via silica gel chromatography (9:1 Hexanes:EtOAc) afforded the target compound as an orange solid (0.46 g, 1.29 mmol, 82%). Rf 0.38 (4:1 Hexanes:EtOAc); M.p. 124-126° C.; $^1$H NMR (400 MHz, DMSO-d$_6$) 5.13 (2H, s, OCH$_2$), 6.95 (1H, ddd, J=8.4, 2.3, 0.92 Hz, H-4"), 7.17 (1H, dd, J=8.0, 1.5 Hz, H-4'''), 7.30 (1H, dd, J=2.3, 2.2 Hz, H-2"), 7.31-7.50 (6H, m, H-5", H-6", H-2'''/H-6''', H3'''/H-5'''), 9.15 (1H, s, H-6), 10.39 (1H, s, NH); $^{13}$C NMR (100 MHz, DMSO-d$_6$) δ69.9 (OCH$_2$), 111.7 (Ar—C), 113.1 (Ar—C), 117.4 (Ar—C), 128.2 (Ar—C), 128.3 (Ar—C), 128.4 (Ar—C), 129.0 (Ar—C), 130.0 (Ar—C), 137.3 (Ar—C), 137.9 (Ar—C), 154.2 (Ar—C), 158.1 (Ar—C), 159.0 (Ar—C), 162.4 (Ar—C). HRMS cal. C$_{17}$H$_{13}$ClN$_4$O$_3$ (ES+) m/z 356.0676181 [M+H]$^+$, found 356.073123.

N4-(3-(Benzyloxy)phenyl)-2-chloropyrimidine-4,5-diamine. Nitropyrimidine (0.42 g, 1.18 mmol) and tin(II) chloride (0.89 g, 4.72 mmol) were taken up in EtOH (12 mL) and reacted according to General Procedure B. Purification via silica gel chromatography (97:3 DCM:MeOH) afforded the target compound as a purple solid (0.34 g, 1.02 mmol, 86%). Rf 0.43 (97:3 DCM:MeOH); M.p. 132-134° C.; IR (cm$^{-1}$) 3420, 3347, 3261, 3178, 1659, 1607, 1568; $^1$H NMR (400 MHz, DMSO-d$_6$) 5.11 (2H, s, OCH$_2$), 5.32 (2H, s, NH$_2$), 6.68-6.78 (1H, m, H-4"), 7.21-7.63 (8H, m, H-2", H-5", H-6", H-2'''/H-6''', H3'''/H-5'''), 7.68 (1H, s, H-6), 8.60 (1H, s, NH); $^{13}$C NMR (100 MHz, DMSO-d$_6$) δ9.7 (OCH$_2$), 107.5 (Ar—C), 109.7 (Ar—C), 113.4 (Ar—C), 128.2 (Ar—C), 128.3 (Ar—C), 128.6 (Ar—C), 128.9 (Ar—C), 129.9 (Ar—C), 137.5 (Ar—C), 139.1 (Ar—C), 140.9 (Ar—C), 146.2 (Ar—C), 150.5 (Ar—C), 159.1 (Ar—C). HRMS cal. C$_{17}$H$_{15}$ClN$_4$O (ES+) m/z 326.0934373 [M+H]$^+$, found 326.101306.

9-(3-(Benzyloxy)phenyl)-2-chloro-9H-purine. Diaminopyrimidine (0.25 g, 0.78 mmol), triethyl orthoformate (0.32 mL, 1.94 mmol) and TFA (6 µL, 0.08 mmol) were taken up in TFE (4 mL) and reacted according to General Procedure C. Purification via silica gel chromatography (7:3 Hexanes:EtOAc) afforded the target compound as a brown solid (0.22 g, 0.65 mmol, 84%). Rf 0.36 (97:3 DCM:MeOH); M.p. 127-128° C.; IR (cm$^{-1}$) 3094, 3043, 1739, 1595, 1583, 1495; $^1$H NMR (400 MHz, DMSO-d$_6$) 5.21 (2H, s, OCH$_2$), 7.19 (1H, ddd, J=8.2, 2.5, 2.5 Hz, H-4"), 7.30-7.67 (8H, m, H-2", H-5", H-6", H-2'''/H-6''', H3'''/H-5''', H-4"), 9.07 (1H, s, H-8), 9.22 (1H, s, H-6); $^{13}$C NMR (100 MHz, DMSO-d$_6$) 70.2 (OCH$_2$), 111.0 (Ar—C), 115.1 (Ar—C), 116.3 (Ar—C), 128.4 (Ar—C), 128.5 (Ar—C), 129.0 (Ar—C), 131.1 (Ar—C), 134.2 (Ar—C), 135.2 (Ar—C), 137.0 (Ar—C), 147.4 (Ar—C), 151.0 (Ar—C), 153.0 (Ar—C), 153.8 (Ar—C), 159.6 (Ar—C). HRMS cal. C$_{18}$H$_{15}$ClN$_4$O (ES+) m/z 336.0777870 [M+H]$^+$, found 336.083655.

4-((9-(3-(Benzyloxy)phenyl)-9H-purin-2-yl)amino)-2,6-difluorophenol (Compound No. A1-8). Purine (0.13 g, 0.40 mmol), aniline (0.13 g, 0.80 mmol) and TFA (61 µL, 0.80 mmol) were taken up in TFE (4 mL) and reacted according to General Procedure D. Purification via silica gel chromatography (1:1 Hexanes:EtOAc) afforded the target compound as a brown solid (0.13 g, 0.29 mmol, 52%). Rf 0.28 (1:1 Hexanes:EtOAc); M.p. 216-219° C.; IR (cm$^{-1}$) 3074, 1593, 1513; $^1$H NMR (400 MHz, DMSO-d$_6$) 5.20 (2H, s, OCH$_2$), 7.10-7.18 (1H, m, H-4"), 7.30-7.66 (8H, m, H-3'/5', H-2", H-5", H-6", H-2'''/H-6''', H3'''/H-5''', H-4"'), 8.68 (1H, s, H-8), 8.96 (1H, s, H-6), 9.55 (1H, s, NH), 9.82 (1H, s, OH); $^{13}$C NMR (100 MHz, DMSO-d$_6$) 70.2 (OCH$_2$), 102.4 (d, J$_{CF}$=27.7 Hz, Ar—C), 110.2 (Ar—C), 114.5 (Ar—C), 115.8 (Ar—C), 127.8 (dd, J$_{CF}$=16.9, 16.7 Hz, Ar—C), 128.3 (Ar—C), 128.5 (Ar—C), 129.0 (Ar—C), 130.9 (Ar—C), 132.9 (dd, J$_{CF}$=12.8, 12.8 Hz, Ar—C), 136.2 (Ar—C), 137.1 (Ar—C), 143.2 (Ar—C), 150.3 (Ar—C), 152.1 (Ar—C), 153.8 (dd, J$_{CF}$=237.8, 8.7 Hz, Ar—C), 156.8 (Ar—C), 159.7 (Ar—C). HRMS cal. C$_{24}$H$_{17}$F$_2$N$_5$O$_2$ (ES+) m/z 445.1350306 [M+H]$^+$, found 445.140626.

2,6-Difluoro-4-((9-(3-hydroxyphenyl)-9H-purin-2-yl)amino)phenol (Compound No. A1-10). Benzyl-protected purine (71.7 mg, 0.16 mmol), ammonium formate (54.3 mg, 0.80 mmol) and Pd/C (18.1 mg, 20% w/w) were reacted in DMF (3.2 mL) according to General Procedure E. Purification via silica gel chromatography (9:1 DCM:MeOH) followed by subsequent trituration with MeOH afforded the target compound as a purple solid (9.8 mg, 0.03 mmol, 19%). Rf 0.34 (9:1 DCM:MeOH); M.p.>300° C.; IR (cm$^{-1}$) 3429, 3279, 3111, 1615, 1524; $^1$H NMR (400 MHz, DMSO-d$_6$) 6.90 (1H, ddd, J=8.2, 2.4, 2.3 Hz, H-4"), 7.28 (1H, dd, J=2.3, 2.2 Hz, H-2") 7.30-7.35 (1H, m, H-6"), 7.40 (1H, dd, J=8.0, 8.0 Hz, H-5"), 7.56 (2H, d, J=10.1 Hz, H-3'/5'), 8.61 (1H, s, H-8), 8.95 (1H, s, H-6); 9.55 (1H, s, NH), 9.80 (1H, s, OH), 9.96 (1H, s, OH); $^{13}$C NMR (100 MHz, DMSO-d$_6$) 102.4 (d, J$_{CF}$=27.7 Hz, Ar—C), 110.8 (Ar—C), 114.1 (Ar—C), 115.2 (Ar—C), 127.8 (dd, J$_{CF}$=16.8, 16.5 Hz, Ar—C), 128.9 (Ar—C), 130.7 (Ar—C), 133.0 (dd, J$_{CF}$=12.5, 12.4 Hz, Ar—C), 136.0 (Ar—C), 143.2 (Ar—C), 150.2 (Ar—C), 152.1 (Ar—C), 153.8 (dd, J$_{CF}$=237.7, 8.7 Hz, Ar—C), 156.7 (Ar—C), 158.9 (Ar—C). HRMS cal. C$_{17}$H$_{11}$F$_2$N$_5$O$_2$ (ES+) m/z 355.088080 [M+H]$^+$, found 355.095157.

2-Chloro-7-isopentyl-7H-pyrrolo[2,3-d]pyrimidine. To a stirring solution of 2-chloro-7H-pyrrolo[2,3-d]pyrimidine (52.7 mg, 0.33 mmol, 1.0 equiv.) in MeCN (0.65 mL, 0.5 M) was added NaH (21.7 mg, 0.36 mmol, 1.1 equiv., 60% w/w). The reaction was allowed to stir for 30 minutes prior to the addition of 1-bromo-3-methylbutane (43 µL, 0.36 mmol, 1.1 equiv.). The reaction was allowed to stir for 16 hours, an additional 1.1 equivalents of alkyl halide was added, and the reaction was stirred for an additional 24 hours before being concentrated in vacuo. The crude residue was resuspended in EtOAc (10 mL), washed with H$_2$O (10 mL) and extracted with EtOAc (3×10 mL). The combined organic extracts were dried (MgSO$_4$), concentrated in vacuo and purified via silica gel chromatography (85:15 Hexanes:EtOAc) to afford the desired yellow oil (71.2 mg, 0.32 mmol, 93%). Rf 0.27 (1:1 Hexanes:EtOAc); IR (cm$^{-1}$) 3103, 2954, 2872, 1587, 1552, 1512; $^1$H NMR (400 MHz, DMSO-d$_6$) 0.90 (6H, d, J=6.6 Hz, CH(CH$_3$)$_2$, 1.36-1.52 (1H, m, CH(CH$_3$)$_2$), 1.75 (2H, dt, J=7.3, 7.1 Hz, NCH$_2$CH$_2$), 4.22 (2H, t, J=7.3 Hz, NCH$_2$CH$_2$), 6.68 (1H, d, J=3.6 Hz, H-5), 7.71 (1H, d, J=3.6 Hz, H-6), 8.90 (1H, s, H-4); $^{13}$C NMR (100 MHz, DMSO-d$_6$) 22.6 (CH(CH$_3$)$_2$), 25.6 (CH(CH$_3$)$_2$), 38.7 (NHCH$_2$CH$_2$), 42.7 (NHCH$_2$CH$_2$), 100.2 (Ar—C), 118.1 (Ar—C), 131.8 (Ar—C), 151.7 (Ar—C), 152.6 (Ar—C). HRMS cal. C$_{11}$H$_{14}$ClN$_3$ (ES+) m/z 223.0876259 [M+H]$^+$, found 223.095173.

2,6-Difluoro-4-((7-isopentyl-7H-pyrrolo[2,3-d]pyrimidin-2-yl)amino)phenol (Compound No. A1-15). Pyrrolopyrimidine (102 mg, 0.45 mmol), aniline(138 mg, 0.89 mmol) and TFA (171 µL, 2.24 mmol) were taken up in TFE (4.5 mL) and reacted according to General Procedure D. Purification via silica gel chromatography (4:1 Hexanes:EtOAc) afforded the target compound as a white solid (31.4 mg, 0.10 mmol, 21%). Rf 0.22 (3:1 Hexanes:EtOAc); M.p. 175-177° C.; IR (cm$^{-1}$) 3452, 2952, 2872, 1612, 1571, 1533; $^1$H NMR (400 MHz, DMSO-d$_6$) 0.95 (6H, d, J=6.7 Hz, CH(CH$_3$)$_2$, 1.48-1.60 (1H, m, CH(CH$_3$)$_2$), 1.71 (2H, dt, J=7.2, 6.9 Hz, NCH$_2$CH$_2$), 4.17 (2H, t, J=7.2 Hz, NCH$_2$CH$_2$), 6.43 (1H, d, J=3.5 Hz, H-5), 7.30 (1H, d, J=3.5 Hz, H-6), 7.62 (2H, d, J=11.2 Hz, H-3'/5'), 8.68 (1H, s, H-4), 9.41 (1H, s, NH), 9.47 (1H, s, OH); $^{13}$C NMR (100 MHz, DMSO-d$_6$) 22.7 (CH (CH$_3$)$_2$), 25.7 (CH(CH$_3$)$_2$), 38.8 (NHCH$_2$CH$_2$), 42.5 (NHCH$_2$CH$_2$), 99.9(Ar—C), 102.2 (d, J$_{CF}$=27.6 Hz, Ar—C), 112.8 (Ar—C), 127.0 (dd, J$_{CF}$=16.9, 16.7 Hz, Ar—C), 127.4 (Ar—C), 133.8 (dd, J$_{CF}$=12.9, 12.9 Hz, Ar—C), 150.9 (Ar—C), 151.4 (Ar—C), 152.7 (dd, J$_{CF}$=237.7, 8.9 Hz, Ar—C), 155.8 (Ar—C). HRMS cal. C$_{17}$H$_{18}$F$_2$N$_4$O (ES+) m/z 332.1448678 [M+H]$^+$, found 332.151989.

4-((7H-Pyrrolo[2,3-d]pyrimidin-2-yl)amino)-2,6-difluorophenol (Compound No. A1-14). 2-Chloro-7H-pyrrolo[2,3-d]pyrimidine (79.1 mg, 0.45 mmol), aniline (149 mg, 0.98 mmol) and TFA (75 µL, 0.98 mmol) were taken up in TFE (4.8 mL) and reacted according to General Procedure D. Purification via silica gel chromatography (19:1 DCM:MeOH) afforded the target compound as a brown solid (21.9 mg, 0.08 mmol, 16%). Rf 0.25 (19:1 DCM:MeOH); M.p. 244-248° C.; IR (cm$^{-1}$) 3397, 3377, 3114, 1606, 1510; $^1$H NMR (400 MHz, DMSO-d$_6$) 6.41 (1H, d, J=2.7 Hz, H-5), 7.19 (1H, t, J=2.7 Hz, H-6), 7.59 (2H, d, J=10.4 Hz, H-3'/5'), 8.70 (1H, s, H-4), 9.39 (2H, bs, OH, NH), 11.59 (1H, s, NH); $^{13}$C NMR (100 MHz, DMSO-d$_6$) 100.22 (Ar—C), 102.4 (d, J$_{CF}$=27.2 Hz, Ar—C), 112.6 (Ar—C), 124.3 (Ar—C), 126.9 (dd, J$_{CF}$=17.2, 16.7 Hz, Ar—C), 133.9 (dd, J$_{CF}$=12.5, 13.1 Hz, Ar—C), 150.6 (Ar—C), 152.7 (dd, J$_{CF}$=237.9, 9.4 Hz, Ar—C), 152.8 (Ar—C), 156.0 (Ar—C). HRMS cal. C$_{12}$H$_8$F$_2$N$_4$O (ES+) m/z 262.0666173 [M+H]$^+$, found 262.074309.

4-(4-(2-Chloro-7H-pyrrolo[2,3-d]pyrimidin-7-yl)phenyl)morpholine. 2-Chloro-7H-pyrrolo[2,3-d]pyrimidine (0.25 g, 1.63 mmol), 4-morpholinophenylboronic acid (0.44 g, 2.12 mmol) and copper acetate (0.33 g, 1.80 mmol) in CHCl$_3$ (16 mL) was added pyridine (1 mL) and the solution was reacted according to General Procedure F. Purification via silica gel chromatography (13:7 Hexanes:EtOAc) afforded the target compound as a white solid (0.15 g, 0.47 mmol, 28%). Rf 0.29 (1:1 Hexanes:EtOAc); M.p. 70-73° C.; IR (cm$^{-1}$) 2955, 2829, 1581, 1526; $^1$H NMR (400 MHz, DMSO-d$_6$) 3.19 (4H. t, J=5.0 Hz, N(CH$_2$CH$_2$)$_2$O), 3.78 (4H, t, J=4.7 Hz, N(CH$_2$CH$_2$)$_2$O), 6.87 (1H, d, J=3.7 Hz, H-5), 7.13 (2H, d, J=8.9 Hz, H-2"/6"), 7.59 (2H, d, J=8.9 Hz, H-3'/5'), 7.93 (1H, d, J=3.7 Hz, H-6), 9.02 (1H, s, H-4); $^{13}$C NMR (100 MHz, DMSO-d$_6$) 48.7 (NCH$_2$CH$_2$O), 66.5 (NCH$_2$CH$_2$O), 101.5 (Ar—C), 115.8 (Ar—C), 118.8 (Ar—C), 125.3 (Ar—C), 128.3 (Ar—C), 131.8 (Ar—C), 150.7 (Ar—C), 151.4 (Ar—C), 152.4 (Ar—C), 153.2 (Ar—C). HRMS cal. C$_{16}$H$_{15}$ClN$_4$O (ES+) m/z 314.0934373 [M+H]$^+$, found 314.101475.

2,6-Difluoro-4-((7-(4-morpholinophenyl)-7H-pyrrolo[2,3-d]pyrimidin-2-yl)amino)phenol (Compound No. A1-16). Pyrrolopyrimidine (77 mg, 0.25 mmol), aniline (73 mg, 0.51 mmol) and TFA (39 µL, 0.51 mmol) were taken up in TFE (2.5 mL) and reacted according to General Procedure D. Purification via silica gel chromatography (49:1 DCM:MeOH) afforded the target compound as an off-white solid (16.3 mg, 0.04 mmol, 15%). Rf 0.27 (97:3 DCM:MeOH); M.p. 276-279° C.; IR (cm$^{-1}$) 3369, 2943, 1721, 1607, 1521; $^1$H NMR (400 MHz, DMSO-d$_6$) 3.17 (4H. t, J=4.7 Hz, N(CH$_2$CH$_2$)$_2$O), 3.79 (4H, t, J=4.7 Hz, N(CH$_2$CH$_2$)$_2$O), 6.64 (1H, d, J=3.7 Hz, H-5), 7.11 (2H, d, J=9.0 Hz, H-2"/6"), 7.53-7.64 (3H, m, H-6, H-3'/5'), 7.68 (2H, d, J=8.9 Hz, H-3'/5"), 8.80 (1H, s, H-4), 9.43 (1H, s, NH), 9.56 (1H, s, OH); $^{13}$C NMR (100 MHz, DMSO-d$_6$) 49.0 (N(CH$_2$CH$_2$)$_2$O), 66.5 (N(CH$_2$CH$_2$)$_2$O), 101.6 (Ar—C), 102.0 (d, J$_{CF}$=28.2 Hz, Ar—C), 113.2 (Ar—C), 115.9 (Ar—C), 124.8 (Ar—C), 127.0 (dd, J$_{CF}$=16.9, 16.7 Hz, Ar—C), 129.5 (Ar—C), 133.8 (dd, J$_{CF}$=12.9, 12.9 Hz, Ar—C), 150.1 (Ar—C), 151.2 (Ar—C), 151.6 (Ar—C), 152.7 (dd, J$_{CF}$=237.7, 9.6 Hz, Ar—C), 156.2 (Ar—C). HRMS cal. C$_{22}$H$_{19}$F$_2$N$_5$O$_2$ (ES+) m/z 423.1506825 [M+H]$^+$, found 423.157436.

2-Chloro-7-(4-(4-methylpiperazin-1-yl)phenyl)-7H-pyrrolo[2,3-d]pyrimidine. 2-Chloro-7H-pyrrolo[2,3-d]pyrimidine (0.30 g, 1.95 mmol), (4-(4-methylpiperazin-1-yl)boronic acid (0.57 g, 2.54 mmol) and copper acetate (0.39 g, 2.15 mmol) in CHCl$_3$ (20 mL) was added pyridine (1.2 mL) and the solution was reacted according to General Procedure F. Purification via silica gel chromatography (13:7 Hexanes:EtOAc) and subsequent purification via amine chromatography (9:1 Hexanes:EtOAc) afforded the target compound as a white solid (0.16 g, 0.48 mmol, 24%). Rf 0.23 (19:1 DCM:MeOH); M.p. 84-87° C.; IR (cm$^{-1}$) 2932, 2833, 2796, 1583, 1515; $^1$H NMR (400 MHz, CDCl$_3$) 2.37 (3H, s, NCH$_3$), 2.60 (4H, t, J=5.0 Hz, N(CH$_2$CH$_2$)$_2$NCH$_3$), 3.28 (4H, t, J=5.0 Hz, N(CH$_2$CH$_2$)$_2$NCH$_3$), 6.68 (1H, d, J=3.7 Hz, H-5), 7.04 (2H, d, J=9.0 Hz, H-3'/5"), 7.43 (1H, d, J=3.7 Hz, H-6), 7.52 (2H, d, J=9.0 Hz, H-2"/6"), 8.86 (1H, s, H-4); $^{13}$C NMR (100 MHz, CDCl$_3$) 46.2 (NCH$_3$), 48.9 (N(CH$_2$CH$_2$)$_2$NCH$_3$), 55.0 (N(CH$_2$CH$_2$)$_2$NCH$_3$), 100.8 (Ar—C), 116.4 (Ar—C), 118.3 (Ar—C), 125.0 (Ar—C), 128.3 (Ar—C), 130.1 (Ar—C), 150.6 (Ar—C), 151.3 (Ar—C), 151.6 (Ar—C), 154.1 (Ar—C). HRMS cal. C$_{17}$H$_{18}$ClN$_5$ (ES+) m/z 327.125073 [M+H]$^+$, found 327.133098.

2,6-Difluoro-4-((7-(4-(4-methylpiperazin-1-yl)phenyl)-7H-pyrrolo[2,3-d]pyrimidin-2-yl)amino)phenol (Compound No. A1-17). Pyrrolopyrimidine (101 mg, 0.31 mmol), aniline (95 mg, 0.61 mmol) and TFA (47 µL, 0.61 mmol) were taken up in TFE (3 mL) and reacted according to General Procedure D. Purification via silica gel chromatography (93:7 DCM:MeOH) afforded the target compound as a brown solid (14 mg, 0.03 mmol, 10%). Rf 0.3 (9:1 DCM:MeOH); $^1$H NMR (400 MHz, DMSO-d$_6$) 2.25 (3H, s, NCH$_3$), 2.47-2.52 (4H, m, N(CH$_2$CH$_2$)$_2$NCH$_3$), 320 (4H, t, J=5.0 Hz, N(CH$_2$CH$_2$)$_2$NCH$_3$), 6.64 (1H, d, J=3.8 Hz, H-5), 7.09 (2H, d, J=8.8 Hz, H-3'/5'), 7.55 (1H, d, J=3.8 Hz, H-6), 7.56-7.74 (4H, m, H-3'/5', H-2"/6"), 8.79 (1H, s, H-4), 9.44 (1H, bs, NH), 9.55 (1H, s, OH); $^{13}$C NMR (100 MHz, DMSO-d$_6$) 46.2 (NCH$_3$), 48.6 [(NCH$_2$CH$_2$N)CH$_3$]$_{55.0}$ [(NCH$_2$CH$_2$N)CH$_3$]$_{101.6}$ (Ar—C), 102.4 (d, J$_{CF}$=28.6 Hz, Ar—C), 113.2 (Ar—C), 116.1 (Ar—C), 124.8 (Ar—C), 127.1 (dd, J$_{CF}$=17.2, 13.8 Hz, Ar—C), 129.2 (Ar—C), 133.5 (dd, J$_{CF}$=12.9, 12.0 Hz, Ar—C), 150.1 (Ar—C), 151.22 (Ar—C), 151.6 (Ar—C), 152.7 (dd, J$_{CF}$=236.5, 9.5 Hz, Ar—C), 156.2 (Ar—C). HRMS cal. C$_{23}$H$_{22}$F$_2$N$_6$O (ES+) m/z 436.182317 [M+H]$^+$, found 436.189815.

2-Chloro-5-nitro-N-(3-phenoxyphenyl)pyrimidin-4-amine. 3-Phenoxy aniline (0.35 g, 1.86 mmol, 1.2 equiv.) was taken up in DCM (2.0 mL, 1 M) and reacted with a solution of 2,4-dichloro-5-nitropyrimidine (0.31 g, 1.55 mmol) in DCM (3.0 mL, 0.5 M) according to the described General Procedure A. Purification via silica gel chromatography (9:1 Hexanes:EtOAc) afforded the target compound as an orange solid (0.28 g, 0.80 mmol, 51%). Rf 0.31 (17:3 Hexanes:EtOAc); M.p. 236-237° C.; IR (cm$^{-1}$) 3300, 3055, 1610, 1567, 1518; $^1$H NMR (400 MHz, DMSO-d$_6$) 6.89-6.98 (1H, m, H-4"), 7.04-7.12 (2H, m, H-2"'/6"'), 7.17 (1H, t, J=7.9 Hz, H-2"), 7.24-7.34 (2H, m, H-5", H-4"'), 7.36-7.48 (3H, m, H-6", H-3"'/5"'), 9.14 (1H, s, H-6), 10.43 (1H, s, NH); $^{13}$C NMR (100 MHz, DMSO-d$_6$) 115.1 (Ar—C), 116.7 (Ar—C), 119.1 (Ar—C), 119.4 (Ar—C), 119.9 (Ar—C), 124.3 (Ar—C), 130.5 (Ar—C), 130.6 (Ar—C), 138.1 (Ar—C), 154.2 (Ar—C), 156.6 (Ar—C), 157.2 (Ar—C), 158.1 (Ar—C), 162.3 (Ar—C). HRMS cal. C$_{16}$H$_{11}$ClN$_4$O$_3$ (ES+) m/z 342.051968 [M+H]$^+$, found 342.058201.

2-Chloro-N4-(3-phenoxyphenyl)pyrimidine-4,5-diamine. Nitropyrimidine 0.24 g, 0.71 mmol) and tin(II) chloride (0.54 g, 2.84 mmol) were taken up in EtOH (8 mL) and reacted according to General Procedure B. Purification via silica gel chromatography (85:15 DCM:MeOH) afforded the target compound as a brown solid (0.18 g, 0.57 mmol, 80%). Rf 0.21 (97:3 DCM:MeOH); M.p. 146-147° C.; IR (cm$^{-1}$) 3419, 3363, 3271, 3210, 1670, 1608, 1566; $^1$H NMR (400 MHz, DMSO-d$_6$) 5.30 (2H, bs, NH$_2$), 6.67-6.75 (1H, m, H-4"), 7.04-7.12 (2H, m, H-2"'/6"'), 7.16 (1H, t, J=7.2 Hz, H-2"), 7.31-7.48 (5H, m, H-5", H-6", H-4"', H-3"'/5"'), 7.67 (1H, s, H-6), 8.67 (1H, bs, NH); $^{13}$C NMR (100 MHz, DMSO-d$_6$) 110.4 (Ar—C), 113.1 (Ar—C), 115.4 (Ar—C), 119.5 (Ar—C), 124.1 (Ar—C), 128.7 (Ar—C), 130.4 (Ar—C), 130.6 (Ar—C), 139.3 (Ar—C), 141.3 (Ar—C), 146.0 (Ar—C), 150.3 (Ar—C), 156.7 (Ar—C), 157.6 (Ar—C). HRMS cal. C$_{16}$H$_{11}$ClN$_4$O$_3$ (ES+) m/z 342.051968 [M+H]$^+$, found 342.058201.

2-Chloro-9-(3-phenoxyphenyl)-9H-purine. Diaminopyrimidine (0.15 g, 0.49 mmol), triethyl orthoformate (0.20 mL, 1.22 mmol) and TFA (4 µL, 0.05 mmol) were taken up in TFE (2.5 mL) and reacted according to General Procedure C. Purification via silica gel chromatography (85:15 DCM:MeOH) afforded the target compound as a white solid (0.15 g, 0.47 mmol, 97%). Rf 0.37 (97:3 DCM:MeOH); M.p. 149-151° C.; IR (cm$^{-1}$) 3047, 1577; $^1$H NMR (400 MHz, DMSO-d$_6$) 7.08-7.17 (3H, m, H-2", H2'''/6'''), 7.18-7.24 (1H, m, H-4'''), 7.41-7.50 (2H, m, H-3'''/5'''), 7.62-7.71 (3H, m, H-4", H-5", H-6"), 9.08 (1H, s, H-8), 9.21 (1H, s, H-6); $^{13}$C NMR (100 MHz, DMSO-d$_6$) 114.2 (Ar—C), 118.3 (Ar—C), 118.6 (Ar—C), 119.5 (Ar—C), 124.6 (Ar—C), 130.7 (Ar—C), 131.6 (Ar—C), 134.2 (Ar—C), 135.6 (Ar—C), 147.3 (Ar—C), 151.0 (Ar—C), 153.0 (Ar—C), 153.8 (Ar—C), 156.3 (Ar—C), 158.0 (Ar—C). HRMS cal. C$_{17}$H$_{11}$ClN$_4$O (ES+) m/z 322.0621367 [M+H]$^+$, found 322.068607.

2,6-Difluoro-4-((9-(3-phenoxyphenyl)-9H-purin-2-yl)amino)phenol (Compound No. A1-6). Purine (76.2 mg, 0.23 mmol), aniline (68.6 mg, 0.47 mmol) and TFA (36 µL, 0.46 mmol) were taken up in TFE (2.3 mL) and reacted according to General Procedure D. Purification via silica gel chromatography (19:1 DCM:MeOH) afforded the target compound as a brown solid (32.5 mg, 0.08 mmol, 33%). Rf 0.25 (19:1 DCM:MeOH); M.p. 163-167° C.; IR (cm$^{-1}$) 1587, 1517; $^1$H NMR (400 MHz, DMSO-d$_6$) 7.03 (1H, dd, J=8.9, 2.2 Hz, H-2"), 7.10-7.16 (2H, m, H-2'''/6'''), 7.16-7.23 (1H, m, H-4'''), 7.42 (2H, dt, J=8.3, 7.7 Hz, H-3'''/5'''), 7.49-7.65 (3H, m, H-3'/5', H-5"), 8.70 (1H, s, H-8), 8.95 (1H, s, H-6), 9.55 (1H, s, NH), 9.82 (1H, s, OH); $^{13}$C NMR (100 MHz, DMSO-d$_6$) 102.4 (d, J$_{CF}$=28.1 Hz, Ar—C), 113.7 (Ar—C), 117.3 (Ar—C), 118.1 (Ar—C), 119.6 (Ar—C), 124.6 (Ar—C), 127.8 (dd, J$_{CF}$=18.7, 16.2 Hz, Ar—C), 130.7 (Ar—C), 131.4 (Ar—C), 132.9 (dd, J$_{CF}$=12.8, 12.8 Hz, Ar—C), 136.5 (Ar—C), 143.1 (Ar—C), 150.3 (Ar—C), 152.0 (Ar—C), 152.7 (dd, J$_{CF}$=236.3, 8.7 Hz, Ar—C), 156.4 (Ar—C), 156.8 (Ar—C), 158.2 (Ar—C).

2-Chloro-5-nitro-N-(4-phenoxyphenyl)pyrimidin-4-amine. 4-Phenoxyaniline (0.29 g, 1.55 mmol, 1.2 equiv.) was taken up in DCM (1.6 mL, 1 M) and reacted with a solution of 2,4-dichloro-5-nitropyrimidine (0.25 g, 1.29 mmol) in DCM (2.6 mL, 0.5 M) according to the described General Procedure A. Purification via silica gel chromatography (9:1 Hexanes:EtOAc) afforded the target compound as an orange solid (0.32 g, 0.94 mmol, 72%). Rf 0.4 (17:3 Hexanes:EtOAc); M.p. 103-104° C.; IR (cm$^{-1}$) 3318, 1616, 1577; $^1$H NMR (400 MHz, DMSO-d$_6$) 7.02-7.10 (4H, m, H-3'/5'', H-2'''/6'''), 7.17 (1H, dd, J=7.4, 7.2 Hz, H-4'''), 7.42 (2H, dt, J=7.4, 6.3 Hz, H-3'''/5'''), 7.50-7.57 (2H, m, H-2"/6"), 9.14 (1H, s, H-6), 10.43 (1H, s, NH); $^{13}$C NMR (100 MHz, DMSO-d$_6$) 119.0 (Ar—C), 119.3 (Ar—C), 124.2 (Ar—C), 127.1 (Ar—C), 130.6 (Ar—C), 131.9 (Ar—C), 154.4 (Ar—C), 155.4 (Ar—C), 156.9 (Ar—C), 158.1 (Ar—C), 162.5 (Ar—C). HRMS cal. C$_{16}$H$_{11}$ClN$_4$O$_3$ (ES+) m/z 342.0519689 [M+H]$^+$, found 342.057842.

2-Chloro-N4-(4-phenoxyphenyl)pyrimidine-4,5-diamine. Nitropyrimidine (0.27 g, 0.79 mmol) and tin(II) chloride (0.60 g, 3.15 mmol) were taken up in EtOH (8 mL) and reacted according to General Procedure B. Purification via silica gel chromatography (19:1 DCM:MeOH) afforded the target compound as a brown solid (0.26 g, 0.82 mmol, >99%). Rf 0.26 (19:1 DCM:MeOH); M.p. 66-71° C.; IR (cm$^{-1}$) 3350, 3045, 1568; $^1$H NMR (400 MHz, DMSO-d$_6$) 5.27 (2H, bs, NH$_2$), 6.95-7.08 (4H, m, H-3''/5'', H-2'''/6'''), 7.12 (1H, dd, J=7.3, 7.3 Hz, H-4'''), 7.42 (2H, dt, J=7.7, 7.4 Hz, H-3'''/5'''), 7.62-7.73 (3H, m, H-6, H-2"/6"), 8.65 (1H, s, NH); $^{13}$C NMR (100 MHz, DMSO-d$_6$) 118.5 (Ar—C), 119.8 (Ar—C), 122.6 (Ar—C), 123.5 (Ar—C), 128.4 (Ar—C), 130.5 (Ar—C), 135.5 (Ar—C), 138.8 (Ar—C), 146.3 (Ar—C), 150.8 (Ar—C), 152.3 (Ar—C), 157.8 (Ar—C). HRMS cal. C$_{16}$H$_{13}$ClN$_4$O (ES+) m/z 312.0777896 [M+H]$^+$, found 312.084621.

2-Chloro-9-(4-phenoxyphenyl)-9H-purine. Diaminopyrimidine (0.23 g, 0.74 mmol), triethyl orthoformate (0.31 mL, 1.84 mmol) and TFA (6 µL, 0.07 mmol) were taken up in TFE (3.7 mL) and reacted according to General Procedure C. Purification via silica gel chromatography (85:15 DCM:MeOH) afforded the target compound as a white solid (0.23 g, 0.72 mmol, 98%). Rf 0.3 (97:3 DCM:MeOH); M.p. 146-147° C.; IR (cm$^{-1}$) 3069, 1583, 1503; $^1$H NMR (400 MHz, DMSO-d$_6$) 7.10-7.16 (2H, m, H-3''/5''), 7.18-7.30 (3H, m, H-4''', H-2'''/6'''), 7.42-7.51 (2H, m, H-3'''/5'''), 7.80-7.89 (3H, m, H-6, H-2"/6"), 9.01 (1H, s, H-8), 9.22 (1H, s, H-6); $^{13}$C NMR (100 MHz, DMSO-d$_6$) 119.6 (Ar—C), 119.8 (Ar—C), 124.6 (Ar—C), 126.4 (Ar—C), 129.3 (Ar—C), 130.7 (Ar—C), 134.0 (Ar—C), 147.7 (Ar—C), 150.9 (Ar—C), 153.2 (Ar—C), 153.8 (Ar—C), 156.6 (Ar—C), 157.3 (Ar—C). HRMS cal. C$_{17}$H$_1$ClN$_4$O (ES+) m/z 322.0621386 [M+H]$^+$, found 322.067034.

2,6-Difluoro-4-((9-(4-phenoxyphenyl)-9H-purin-2-yl)amino)phenol (Compound No. A1-7). Purine (83.4 mg, 0.25 mmol), aniline (76.7 mg, 0.50 mmol) and TFA (38 µL, 0.50 mmol) were taken up in TFE (2.5 mL) and reacted according to General Procedure D. Purification via silica gel chromatography (19:1 DCM; MeOH) afforded the target compound as a brown solid (47.7 mg, 0.11 mmol, 43%). Rf 0.25 (19:1 DCM:MeOH); M.p. 228-230° C.; IR (cm$^{-1}$) 1618, 1590, 1517; $^1$H NMR (400 MHz, DMSO-d$_6$) 7.08-7.15 (2H, m, H-3''/5''), 7.17-7.27 (3H, m, H-4''', H-2'''/6'''), 7.41-7.51 (2H, m, H-3'''/5'''), 7.49-7.65 (2H, m, H-3'/5'), 7.85-7.95 (2H, m, H-2"/6"), 8.63 (1H, s, H-8), 8.96 (1H, s, H-6), 9.52 (1H, s, NH), 9.80 (1H, s, OH); $^{13}$C NMR (100 MHz, DMSO-d$_6$) 102.4 (d, J$_{CF}$=28.5 Hz, Ar—C), 119.4 (Ar—C), 119.7 (Ar—C), 124.5 (Ar—C), 125.8 (Ar—C), 127.7 (dd, J$_{CF}$=16.5, 15.9 Hz, Ar—C), 128.8 (Ar—C), 130.2 (Ar—C), 130.7 (Ar—C), 133.0 (dd, J$_{CF}$=13.7, 13.7 Hz, Ar—C), 143.3 (Ar—C), 150.2 (Ar—C), 152.2 (Ar—C), 152.6 (dd, J$_{CF}$=238.0, 8.8 Hz, Ar—C), 156.6 (Ar—C), 156.8 (Ar—C), 156.8 (Ar—C). HRMS cal. C$_{23}$H$_{15}$F$_2$N$_5$O$_2$ (ES+) m/z 431.1193801 [M+H]$^+$, found 431.125252.

2-Chloro-N-(4-(2-morpholinoethyl)phenyl)-5-nitropyrimidin-4-amine. 4-[2-(Morpholin-4-yl)ethyl]aniline (0.35 g, 1.71 mmol, 1.1 equiv.) was taken up in EtOH (1.7 mL, 0.5 M) and reacted with a solution of 2,4-dichloro-5-nitropyrimidine (0.30 g, 1.55 mmol) in DCM (3.0 mL, 0.5 M) according to the described General Procedure A. Purification via silica gel chromatography (19:1 DCM:MeOH) afforded the target compound as an orange solid (0.63 g, >99%). Rf 0.36 (19:1 DCM:MeOH); M.p. 193-220° C. decomposed; IR (cm$^{-1}$) 3311, 2525, 2416, 1704, 1615, 1577, 1516; $^1$H NMR (400 MHz, DMSO-d$_6$) 3.01-3.16 (4H, m, N(CH$_2$CH$_2$)$_2$)O, 3.31-3.41 (4H, m, N(CH$_2$CH$_2$)$_2$)O, 3.84 (2H, t, J=12.1 Hz, (CH$_2$CH$_2$N(CH$_2$CH$_2$)$_2$)O), 3.98 (2H, t, J=12.1 Hz, (CH$_2$CH$_2$N(CH$_2$CH$_2$)$_2$)O), 7.35 (2H, d, J=8.5 Hz, H-3"/5"), 7.52 (2H, d, J=8.5 Hz, H-2"/6"), 9.16 (1H, s, H-6), 10.44 (1H, s, NH); $^{13}$C NMR (100 MHz, DMSO-d$_6$) 29.0 (CH$_2$CH$_2$N(CH$_2$CH$_2$)$_2$)O), 51.4 (CH$_2$CH$_2$N(CH$_2$CH$_2$)$_2$)O), 56.8 (CH$_2$CH$_2$N(CH$_2$CH$_2$)$_2$)O), 63.7 (CH$_2$CH$_2$N(CH$_2$CH$_2$)$_2$)O), 125.5 (Ar—C), 128.3 (Ar—C), 129.4 (Ar—C), 135.4 (Ar—C), 135.6 (Ar—C), 154.3 (Ar—C), 158.1 (Ar—C), 162.4 (Ar—C). HRMS cal. C$_{16}$H$_{18}$ClN$_5$O$_3$ (ES+) m/z 363.10981688 [M+H]$^+$, found 363.1177.

2-Chloro-N4-(4-(2-morpholinoethyl)phenyl)pyrimidine-4,5-diamine. Nitropyrimidine (0.20 g, 0.55 mmol) and tin (II) chloride (0.43 g, 2.20 mmol) were taken up in EtOH (5.5 mL) and reacted according to General Procedure B. Purification via silica gel chromatography (9:1 DCM:MeOH) afforded the target compound as a brown oil (71.5 mg, 0.21 mmol, 39%). Rf 0.09 (19:1 DCM:MeOH); IR (cm$^{-1}$) 3349, 3264, 2934, 2855, 2813, 1602, 1565, 1508; $^1$H NMR (400 MHz, DMSO-d$_6$) 2.38-2.45 (4H, m, N(CH$_2$CH$_2$)$_2$O), 2.58 (2H, t, J=8.4 Hz, (CH$_2$CH$_2$N(CH$_2$CH$_2$)$_2$)O), 2.85 (2H, t, J=8.4 Hz, (CH$_2$CH$_2$N(CH$_2$CH$_2$)$_2$)O), 3.59 (4H, t, J=4.5 Hz, N(CH$_2$CH$_2$)$_2$O, 5.26 (2H, s, NH$_2$), 7.20 (2H, d, J=8.5 Hz, H-3"/5"), 7.54 (2H, d, J=8.5 Hz, H-2"/6"), 7.63 (1H, s, H-6), 8.56 (1H, s, NH); $^{13}$C NMR (100 MHz, DMSO-d$_6$) 32.3 (CH$_2$CH$_2$N(CH$_2$CH$_2$)$_2$O), 53.8 (CH$_2$CH$_2$N(CH$_2$CH$_2$)$_2$O), 60.6 (CH$_2$CH$_2$N(CH$_2$CH$_2$)$_2$O), 66.7 (CH$_2$CH$_2$N(CH$_2$CH$_2$)$_2$O), 121.1 (Ar—C), 128.4 (Ar—C), 129.3 (Ar—C), 135.6 (Ar—C), 137.5 (Ar—C), 138.7 (Ar—C), 146.4 (Ar—C), 150.8 (Ar—C). HRMS cal. C$_{16}$H$_{20}$ClN$_5$O (ES+) m/z 333.1356369 [M+H]$^+$, found 333.144052.

4-(4-(2-Chloro-9H-purin-9-yl)phenethyl)morpholine. Diaminopyrimidine (65.0 mg, 0.20 mmol), triethyl orthoformate (81 μL, 0.49 mmol) and TFA (2 μL, 0.02 mmol) were taken up in TFE (1.2 mL) and reacted according to General Procedure C. Purification via silica gel chromatography (19:1 DCM:MeOH) afforded the target compound as a white solid (59.6 mg, 0.17 mmol, 89%). Rf 0.26 (19:1 DCM:MeOH); M.p. 181-183° C.; IR (cm$^{-1}$) 3049, 2943, 2854, 2807, 1588, 1517; $^1$H NMR (400 MHz, DMSO-d$_6$) 2.40-2.48 (4H, m, N(CH$_2$CH$_2$)$_2$O), 3.84 (2H, t, J=7.8 Hz, (CH$_2$CH$_2$N(CH$_2$CH$_2$)$_2$O), 3.27-3.37 (2H, m, (CH$_2$CH$_2$N(CH$_2$CH$_2$)$_2$O), 3.58 (4H, t, J=4.5 Hz, N(CH$_2$CH$_2$)$_2$O, 7.51 (2H, d, J=8.1 Hz, H-3"/5"), 7.74 (2H, d, J=8.1 Hz, H-2"/6"), 9.02 (1H, s, H-8), 9.22 (1H, s, H-6); $^{13}$C NMR (100 MHz, DMSO-d$_6$) 32.3 (CH$_2$CH$_2$N(CH$_2$CH$_2$)$_2$O), 53.7 (CH$_2$CH$_2$N(CH$_2$CH$_2$)$_2$O), 60.2 (CH$_2$CH$_2$N(CH$_2$CH$_2$)$_2$O), 66.7 (CH$_2$CH$_2$N(CH$_2$CH$_2$)$_2$O), 124.1 (Ar—C), 130.4 (Ar—C), 132.1 (Ar—C), 134.1 (Ar—C), 141.6 (Ar—C), 147.6 (Ar—C), 150.9 (Ar—C), 153.1 (Ar—C), 153.8 (Ar—C). HRMS cal. C$_{17}$H$_{18}$ClN$_5$O (ES+) m/z 343.1199889 [M+H]$^+$, found 343.128766.

2,6-Difluoro-4-((9-(4-(2-morpholinoethyl)phenyl)-9H-purin-2-yl)amino)phenol (Compound No. A1-4). Purine (102.1 mg, 0.29 mmol), aniline (88.7 mg, 0.58 mmol) and TFA (44 μL, 0.58 mmol) were taken up in TFE (2.9 mL) and reacted according to General Procedure D. Purification via silica gel chromatography (19:1 DCM; MeOH) afforded the target compound as a purple solid (26.6 mg, 0.06 mmol, 20%). Rf 0.26 (9:1 DCM:MeOH); M.p. 216-219° C.; IR (cm$^{-1}$) 3255, 3093, 2954, 2862, 2817, 1606, 1518; $^1$H NMR (400 MHz, DMSO-d$_6$) 2.45 (4H, t, J=4.5 Hz, N(CH$_2$CH$_2$)$_2$O, 2.58 (2H, t, J=7.8 Hz, (CH$_2$CH$_2$N(CH$_2$CH$_2$)$_2$)O), 2.85 (2H, t, J=7.8 Hz, (CH$_2$CH$_2$N(CH$_2$CH$_2$)$_2$)O), 3.59 (4H, t, J=4.5 Hz, N(CH$_2$CH$_2$)$_2$O, 7.47 (2H, d, J=8.4 Hz, H-3"/5"), 7.55 (2H, d, J=10.2 Hz, H-3'/5'), 7.81 (2H, d, J=8.4 Hz, H-2"/6"), 8.64 (1H, s, H-8), 8.95 (1H, s, H-6), 9.54 (1H, s, NH), 9.80 (1H, s, OH); $^{13}$C NMR (100 MHz, DMSO-d$_6$) 32.3 (CH$_2$CH$_2$N(CH$_2$CH$_2$)$_2$O), 53.7 (CH$_2$CH$_2$N(CH$_2$CH$_2$)$_2$O), 60.3 (CH$_2$CH$_2$N(CH$_2$CH$_2$)$_2$O), 66.7 (CH$_2$CH$_2$N(CH$_2$CH$_2$)$_2$O), 102.6 (d, J$_{CF}$=28.8 Hz, Ar—C), 123.5 (Ar—C), 127.7 (dd, J$_{CF}$=17.8, 17.3 Hz, Ar—C), 128.9 (Ar—C), 130.2 (Ar—C), 132.9 (Ar—C), 140.8 (Ar—C), 143.3 (Ar—C), 150.2 (Ar—C), 151.8 (dd, J$_{CF}$=238.0, 8.8 Hz, Ar—C), 156.7 (Ar—C). HRMS cal. C$_{23}$H$_{22}$F$_2$N$_6$O$_2$ (ES+) m/z 452.17723067 [M+H]$^+$, found 452.185917.

Methyl 3-(4-((2-chloro-5-nitropyrimidin-4-yl)amino)phenyl)propanoate. Methyl 3-(4-aminophenyl)propanoate (0.42 g, 2.2 mmol, 1.1 equiv.) was taken up in DCM (4.5 mL, 0.5 M) and reacted with a solution of 2,4-dichloro-5-nitropyrimidine (0.4 g, 2.1 mmol) in DCM (4.1 mL, 0.5 M) according to the described General Procedure A. Purification via silica gel chromatography (19:1 DCM:MeOH) afforded the target compound as a yellow solid (0.25 g, 0.74 mmol, 36%). Rf 0.29 (4:1 Hexanes:EtOAc); M.p. 113-116° C.; IR (cm$^{-1}$) 3306, 3262, 2949, 1744, 1614, 1575, 1513; $^1$H NMR (400 MHz, DMSO-d$_6$) 2.68 (2H, t, J=7.6 Hz, CH$_2$CH$_2$COOCH$_3$), 2.89 (2H, t, J=7.6 Hz, CH$_2$CH$_2$COOCH$_3$), 3.60 (3H, s, COOCH$_3$), 7.30 (2H, d, J=8.5 Hz, H-3"/5"), 7.45 (2H, d, J=8.5 Hz, H-2"/6"), 9.14 (1H, s, H-6), 10.40 (1H, s, NH); $^{13}$C NMR (100 MHz, DMSO-d$_6$) 30.2 (CH$_2$CH$_2$COOCH$_3$), 35.1 (CH$_2$CH$_2$COOCH$_3$), 51.8 (CH$_2$CH$_2$COOCH$_3$), 125.2 (Ar—C), 128.2 (Ar—C), 129.0 (Ar—C), 134.7 (Ar—C), 139.2 (Ar—C), 154.3 (Ar—C), 158.1 (Ar—C), 162.5 (Ar—C), 173.1 (CH$_2$CH$_2$COOCH$_3$). HRMS cal. C$_{14}$H$_{13}$ClN$_6$O$_4$ (ES+) m/z 336.0625306 [M+H]$^+$, found 336.069094.

Methyl 3-(4-((5-amino-2-chloropyrimidin-4-yl)amino)phenyl)propanoate. Nitropyrimidine (0.50 g, 1.48 mmol) and tin(II) chloride (1.12 g, 5.92 mmol) were taken up in EtOH (15 mL) and reacted according to General Procedure B. Purification via silica gel chromatography (19:1 DCM:MeOH) afforded the target compound as a brown solid (135 mg, 0.39 mmol, 53%). Rf 0.31 (19:1 DCM MeOH); M.p. 132-135° C.; IR (cm$^{-1}$) 3391, 3220, 2945, 1712, 1607, 1561, 1510; $^1$H NMR (400 MHz, DMSO-d$_6$) 2.63 (2H, t, J=7.7 Hz, CH$_2$CH$_2$COOCH$_3$), 2.83 (2H, t, J=7.7 Hz, CH$_2$CH$_2$COOCH$_3$), 3.59 (3H, s, COOCH$_3$), 5.27 (2H, s, NH$_2$), 7.21 (2H, d, J=8.6 Hz, H-3"/5"), 7.57 (2H, d, J=8.6 Hz, H-2"/6"), 7.65 (1H, s, H-6), 8.58 (1H, s, NH); $^{13}$C NMR (100 MHz, DMSO-d$_6$) 30.2 (CH$_2$CH$_2$COOCH$_3$), 35.4 (CH$_2$CH$_2$COOCH$_3$), 51.8 (CH$_2$CH$_2$COOCH$_3$), 121.1 (Ar—C), 128.4 (Ar—C), 128.9 (Ar—C), 135.7 (Ar—C), 137.7 (Ar—C), 138.8 (Ar—C), 146.3 (Ar—C), 150.8 (Ar—C), 173.2 (CH$_2$CH$_2$COOCH$_3$). HRMS cal. C$_{15}$H$_{17}$ClN$_4$O$_2$ (ES+) m/z 320.10400382 [M+H]$^+$, found 320.111315.

Methyl 3-(4-(2-chloro-9H-purin-9-yl)phenyl)propanoate. Diaminopyrimidine (0.32 g, 1.04 mmol), triethyl orthoformate (0.44 mL, 2.61 mmol) and TFA (8 μL, 0.11 mmol) were taken up in TFE (5 mL) and reacted according to General Procedure C. Purification via silica gel chromatography (1:1 Hexanes:EtOAc) afforded the target compound as an orange solid (269 mg, 0.85 mmol, 81%). Rf (0.35 (19:1 DCM: MeOH); M.p. 126-129° C.; IR (cm$^{-1}$) 1724, 1581, 1515; $^1$H NMR (400 MHz, DMSO-d$_6$) 2.72 (2H, t, J=7.6 Hz, CH$_2$CH$_2$COOCH$_3$), 2.96 (2H, t, J=7.6 Hz, CH$_2$CH$_2$COOCH$_3$), 3.61 (3H, s, COOCH$_3$), 7.51 (2H, d, J=8.5 Hz, H-3"/5"), 7.75 (2H, d, J=8.5 Hz, H-2"/6"), 9.02 (1H, s, H-8), 9.21 (1H, s, H-6); $^{13}$C NMR (100 MHz, DMSO-d$_6$) 30.2 (CH$_2$CH$_2$COOCH$_3$), 35.1 (CH$_2$CH$_2$COOCH$_3$), 51.8 (CH$_2$CH$_2$COOCH$_3$), 124.2 (Ar—C), 130.0 (Ar—C), 132.2 (Ar—C), 134.1 (Ar—C), 141.7 (Ar—C), 147.5 (Ar—C), 150.9 (Ar—C), 153.1 (Ar—C), 153.7 (Ar—C), 173.0 (CH$_2$CH$_2$COOCH$_3$); HRMS cal. C$_{15}$H$_{13}$ClN$_4$O$_2$ (ES+) m/z 316.07270227 [M+H]$^+$, found 316.079324.

Methyl 3-(4-(2-((3,5-difluoro-4-hydroxyphenyl)amino)-9H-purin-9-yl)phenyl)-propanoate (Compound No. A1-12). Purine (83.3 mg, 0.25 mmol), aniline (74.7 mg, 0.51 mmol) and TFA (39 μL, 0.51 mmol) were taken up in TFE (2.5 mL) and reacted according to General Procedure D. Purification via silica gel chromatography (19:1 DCM; MeOH) afforded the target compound as a brown solid (46.6 mg, 0.11 mmol, 42%). Rf 0.15 (19:1 DCM:MeOH); M.p. 255-259° C.; IR (cm$^1$) 3361, 2966, 1723, 1613, 1579, 1521; $^1$H NMR (400

MHz, DMSO-d$_6$) 2.72 (2H, t, J=7.6 Hz, CH$_2$CH$_2$COOCH$_3$), 2.97 (2H, t, J=7.6 Hz, CH$_2$CH$_2$COOCH$_3$), 3.61 (3H, s, COOCH$_3$), 7.47 (2H, d, J=8.4 Hz, H-3"/5"), 7.55 (2H, d, J=10.8 Hz, H-3'/5'), 7.82 (2H, d, J=8.4 Hz, H-2"/6"), 8.64 (1H, s, H-8), 8.95 (1H, s, H-6), 9.53 (1H, s, NH), 9.80 (1H, s, OH); $^{13}$C NMR (100 MHz, DMSO-d$_6$) 30.2 (CH$_2$CH$_2$COOCH$_3$), 35.2 (CH$_2$CH$_2$COOCH$_3$), 51.8 (CH$_2$CH$_2$COOCH$_3$), 102.5 (d, J$_{CF}$=27.8 Hz, Ar—C), 128.9 (Ar—C), 129.8 (Ar—C), 127.7 (dd, J$_{CF}$=17.1, 17.1 Hz, Ar—C), 128.9 (Ar—C), 129.8 (Ar—C), 140.8 (Ar—C), 143.2 (Ar—C), 150.1 (Ar—C), 152.1 (Ar—C), 152.6 (dd, J$_{CF}$=238.0, 8.8 Hz, Ar—C), 156.7 (Ar—C), 173.1 (CH$_2$CH$_2$COOCH$_3$). HRMS cal. C$_{21}$H$_{17}$F$_2$N$_5$O$_3$ (ES+) m/z 425.12994429 [M+H]$^+$, found 425.137163.

Methyl 4-(4-((2-chloro-5-nitropyrimidin-4-yl)amino)phenyl)butanoate. Methyl 4-(4-aminophenyl)butanoate (0.15 g, 0.78 mmol, 1.1 equiv.) was taken up in DCM (1.6 mL, 0.5 M) and reacted with a solution of 2,4-dichloro-5-nitropyrimidine (0.14 g, 0.71 mmol) in DCM (1.4 mL, 0.5 M) according to the described General Procedure A. Purification via silica gel chromatography (4:1 Hexanes:EtOAc) afforded the target compound as an orange solid (135 mg, 0.38 mmol, 53%). Rf 0.31 (4:1 Hexanes:EtOAc); M.p. 78-79° C.; IR (cm$^{-1}$) 3309, 3043, 2935, 2857, 1728, 1617, 1573, 1510; $^1$H NMR (400 MHz, DMSO-d$_6$) 1.86 (2H, tt, J=7.5, 7.5 Hz, CH$_2$CH$_2$CH$_2$COOCH$_3$), 2.34 (2H, t, J=7.5 Hz, CH$_2$CH$_2$CH$_2$COOCH$_3$), 2.63 (2H, t, J=7.5 Hz, CH$_2$CH$_2$CH$_2$COOCH$_3$), 3.60 (3H, s, OCH$_3$), 7.27 (2H, d, J=8.0 Hz, H-3"/5"), 7.45 (2H, d, J=8.0 Hz, H-2"/6"), 9.15 (1H, s, H-6), 10.40 (1H, s, NH); $^{13}$C NMR (100 MHz, DMSO-d$_6$) 26.6 (CH$_2$CH$_2$CH$_2$COOCH$_3$), 33.2 (CH$_2$CH$_2$CH$_2$COOCH$_3$), 34.3 (CH$_2$CH$_2$CH$_2$COOCH$_3$), 51.7 (CH$_2$CH$_2$CH$_2$COOCH$_3$), 125.2 (Ar—C), 128.2 (Ar—C), 129.1 (Ar—C), 134.5 (Ar—C), 140.1 (Ar—C), 154.3 (Ar—C), 158.1 (Ar—C), 162.5 (Ar—C), 173.6 (CH$_2$CH$_2$CH$_2$COOCH$_3$). HRMS cal. C$_{15}$H$_{15}$ClN$_4$O$_4$ (ES+) m/z 350.07818314 [M+H]$^+$, found 350.084271.

Methyl 4-(4-((5-amino-2-chloropyrimidin-4-yl)amino)phenyl)butanoate. Nitropyrimidine (0.14 g, 0.41 mmol) and tin(II) chloride (0.31 g, 1.62 mmol) were taken up in EtOH (4 mL) and reacted according to General Procedure B. Purification via silica gel chromatography (97:3 DCM:MeOH) afforded the target compound as a brown oil (101 mg, 0.32 mmol, 78%). Rf 0.25 (97:3 DCM:MeOH); IR (cm$^1$) 3358, 3268, 3025, 2942, 2857, 1717, 1599, 1564, 1506; $^1$H NMR (400 MHz, DMSO-d$_6$) 1.83 (2H, tt, J=7.4, 7.4 Hz, CH$_2$CH$_2$CH$_2$COOCH$_3$), 2.32 (2H, t, J=7.4 Hz, CH$_2$CH$_2$CH$_2$COOCH$_3$), 2.57 (2H, t, J=7.4 Hz, CH$_2$CH$_2$CH$_2$COOCH$_3$), 3.59 (3H, s, OCH$_3$), 5.27 (2H, s, NH$_2$), 7.18 (2H, d, J=8.3 Hz, H-3"/5"), 7.57 (2H, d, J=8.3 Hz, H-2"/6"), 7.64 (1H, s, H-6), 8.57 (1H, s, NH); $^{13}$C NMR (100 MHz, DMSO-d$_6$) 26.7 (CH$_2$CH$_2$CH$_2$COOCH$_3$), 33.2 (CH$_2$CH$_2$CH$_2$COOCH$_3$), 34.2 (CH$_2$CH$_2$CH$_2$COOCH$_3$), 51.7 (CH$_2$CH$_2$CH$_2$COOCH$_3$), 121.2 (Ar—C), 128.4 (Ar—C), 129.0 (Ar—C), 136.6 (Ar—C), 137.5 (Ar—C), 138.7 (Ar—C), 146.4 (Ar—C), 150.8 (Ar—C), 173.7 (CH$_2$CH$_2$CH$_2$COOCH$_3$).

Methyl 4-(4-(2-chloro-9H-purin-9-yl)phenyl)butanoate. Diaminopyrimidine (0.18 g, 0.56 mmol), triethyl orthoformate (0.23 mL, 1.39 mmol) and TFA (4.3 µL, 0.06 mmol) were taken up in TFE (2.8 mL) and reacted according to General Procedure C. Purification via silica gel chromatography (49:1 DCM:MeOH) afforded the target compound as a brown solid (166 mg, 0.50 mmol, 90%). Rf 0.46 (19:1 DCM:MeOH); M.p. 85-88° C.; IR (cm$^{-1}$) 3104, 2951, 1723, 1576, 1517; $^1$H NMR (400 MHz, DMSO-d$_6$) 1.90 (2H, tt, J=7.5, 7.5 Hz, CH$_2$CH$_2$CH$_2$COOCH$_3$), 2.36 (2H, t, J=7.5 Hz, CH$_2$CH$_2$CH$_2$COOCH$_3$), 2.71 (2H, t, J=7.5 Hz, CH$_2$CH$_2$CH$_2$COOCH$_3$), 3.61 (3H, s, OCH$_3$), 7.47 (2H, d, J=8.5 Hz, H-3"/5"), 7.76 (2H, d, J=8.5 Hz, H-2"/6"), 9.02 (1H, s, H-8), 9.21 (1H, s, H-6); $^{13}$C NMR (100 MHz, DMSO-d$_6$) 26.6 (CH$_2$CH$_2$CH$_2$COOCH$_3$), 33.1 (CH$_2$CH$_2$CH$_2$COOCH$_3$), 34.3 (CH$_2$CH$_2$CH$_2$COOCH$_3$), 51.8 (CH$_2$CH$_2$CH$_2$COOCH$_3$), 124.3 (Ar—C), 130.0 (Ar—C), 132.1 (Ar—C), 134.1 (Ar—C), 142.5 (Ar—C), 147.5 (Ar—C), 150.9 (Ar—C), 153.1 (Ar—C), 153.8 (Ar—C), 173.6 (CH$_2$CH$_2$CH$_2$COOCH$_3$). HRMS cal. C$_{16}$H$_{15}$ClN$_4$O$_2$ (ES+) m/z 330.0883546 [M+H]$^+$, found 330.095138.

Methyl 4-(4-(2-((3,5-difluoro-4-hydroxyphenyl)amino)-9H-purin-9-yl)phenyl)butanoate (Compound No. A1-13). Purine (61.8 mg, 0.18 mmol), aniline (54.2 mg, 0.36 mmol) and TFA (28 µL, 0.36 mmol) were taken up in TFE (1.8 mL) and reacted according to General Procedure D. Purification via silica gel chromatography (19:1 DCM; MeOH) afforded the target compound as a brown solid (21.5 mg, 0.05 mmol, 26%). Rf 0.28 (19:1 DCM:MeOH); M.p. 193-196° C.; IR (cm-1) 3359, 2948, 1716, 1612, 1580, 1520; $^1$H NMR (400 MHz, DMSO-d$_6$) 1.83-1.95 (2H, m, CH$_2$CH$_2$CH$_2$COOCH$_3$), 2.37 (2H, t, J=7.5 Hz, CH$_2$CH$_2$CH$_2$COOCH$_3$), 2.71 (2H, t, J=7.5 Hz, CH$_2$CH$_2$CH$_2$COOCH$_3$), 3.61 (3H, s, OCH$_3$), 7.44 (2H, d, J=8.2 Hz, H-3"/5"), 7.55 (2H, d, J=10.5 Hz, H-3'/5'), 7.83 (2H, d, J=8.4 Hz, H-2"/6"), 8.65 (1H, s, H-8), 8.95 (1H, s, H-6), 9.52 (1H, s, NH), 9.80 (1H, s, OH); $^{13}$C NMR (100 MHz, DMSO-d$_6$) 26.7 (CH$_2$CH$_2$CH$_2$COOCH$_3$), 33.1 (CH$_2$CH$_2$CH$_2$COOCH$_3$), 34.3 (CH$_2$CH$_2$CH$_2$COOCH$_3$), 51.8 (CH$_2$CH$_2$CH$_2$COOCH$_3$), 102.4 (d, J$_{CF}$=27.3 Hz, Ar—C), 123.7 (Ar—C), 127.7 (dd, J$_{CF}$=17.0, 17.0 Hz, Ar—C), 128.9 (Ar—C), 129.8 (Ar—C), 133.0 (Ar—C), 141.7 (Ar—C), 143.2 (Ar—C), 150.2 (Ar—C), 152.1 (Ar—C), 152.6 (dd, J$_{CF}$=239.1, 9.0 Hz, Ar—C), 156.7 (Ar—C), 173.6 (CH$_2$CH$_2$CH$_2$COOCH$_3$). HRMS cal. C$_{22}$H$_{19}$F$_2$N$_5$O$_3$ (ES+) m/z 439.1455939 [M+H]$^+$, found 439.151922.

N-([1,1'-Biphenyl]-4-yl)-2-chloro-5-nitropyrimidin-4-amine. 4-Aminobiphenyl (0.39 g, 2.32 mmol, 1.5 equiv.) was taken up in DCM (2.3 mL, 0.5 M) and reacted with a solution of 2,4-dichloro-5-nitropyrimidine (0.30 g, 1.55 mmol) in DCM (1.6 mL, 1 M) according to the described General Procedure A. Purification via silica gel chromatography (9:1 Hexanes:EtOAc) afforded the target compound as an orange solid (390 mg, 1.19 mmol, 77%). Rf 0.2 (9:1 Hexanes:EtOAc); M.p. 177-179° C.; IR (cm$^{-1}$) 3295, 2918, 1614, 1569; $^1$H NMR (400 MHz, DMSO-d$_6$) 7.39 (1H, dd, J=7.4, 7.2 Hz, H-4'''), 7.49 (2H, dd, J=7.4, 7.4 Hz, H-3'''/5'''), 7.66 (2H, d, J=8.4 Hz, H-3"/5"), 7.69-7.74 (2H, m, H-2'''/6'''), 7.76 (2H, d, J=8.4 Hz, H-2"/6"), 9.18 (1H, s, H-6), 10.51 (1H, s, NH); $^{13}$C NMR (100 MHz, DMSO-d$_6$) 119.7 (Ar—C), 124.4 (Ar—C), 126.9 (Ar—C), 127.2 (Ar—C), 127.8 (Ar—C), 129.4 (Ar—C), 136.9 (Ar—C), 137.4 (Ar—C), 139.9 (Ar—C), 150.5 (Ar—C), 153.6 (Ar—C), 154.7 (Ar—C). HRMS cal. C$_{16}$H$_{11}$ClN$_4$O$_2$ (ES+) m/z 326.05705365 [M+H]$^+$, found 326.062251.

N4-([1,1'-Biphenyl]-4-yl)-2-chloropyrimidine-4,5-diamine. Nitropyrimidine (0.39 g, 1.19 mmol) and tin(II) chloride (0.91 g, 4.76 mmol) were taken up in EtOH (6.6 mL) and reacted according to General Procedure B. Purification via silica gel chromatography (97:3 DCM:MeOH) afforded the target compound as a white solid (254 mg, 0.86 mmol, 72%). Rf 0.22 (97:3 DCM:MeOH); M.p. 111-114° C.; IR (cm$^{-1}$) 3355, 3030, 1590, 1562; $^1$H NMR (400 MHz, DMSO-d$_6$) 5.35 (2H, s, NH$_2$), 7.34 (1H, dd, J=7.4, 7.2 Hz, H-4'''), 7.46 (2H, dd, J=7.6, 7.4 Hz, H-3'''/5'''), 7.66-7.71 (5H, m, H-6, H-3"/5", H-2"/6'''), 7.80 (2H, d, J=8.6 Hz, H-2"/6"), 8.74 (1H, s, NH); $^{13}$C NMR (100 MHz, DMSO-d$_6$) 121.2 (Ar—C), 126.7 (Ar—C), 127.3 (Ar—C), 127.5 (Ar—C), 128.6 (Ar—C), 129.4 (Ar—C), 135.0 (Ar—C), 139.0 (Ar—C), 139.2 (Ar—C), 140.2 (Ar—C), 146.2 (Ar—C), 150.5 (Ar—C). HRMS cal. $C_{16}H_{13}ClN_4$ (ES+) m/z 296.0828753 [M+H]$^+$, found 296.089179.

9-([1,1'-Biphenyl]-4-yl)-2-chloro-9H-purine. Diaminopyrimidine (0.25 g, 0.84 mmol), triethyl orthoformate (0.35 mL, 2.11 mmol) and TFA (6.5 µL, 0.08 mmol) were taken up in TFE (4.2 mL) and reacted according to General Procedure C. Purification via silica gel chromatography (1:1 Hexanes:EtOAc) afforded the target compound as a white solid (225 mg, 0.73 mmol, 86%). Rf 0.41 (97:3 Hexanes:EtOAc); M.p. 169-171° C.; IR (cm$^{-1}$) 1724, 1578; $^1$H NMR (400 MHz, DMSO-d$_6$) 7.43 (1H, dd, J=7.4, 7.3 Hz, H-4'''), 7.53 (2H, dd, J=7.9, 7.4 Hz, H-3'''/5'''), 7.72 (2H, d, J=7.4, H-3''/5''), 7.91-8.00 (4H, m, H-2''/6'', H-2'''/6'''), 9.11 (1H, s, H-8), 9.24 (1H, s, H-6); $^{13}$C NMR (100 MHz, DMSO-d$_6$) 124.5 (Ar—C), 127.3 (Ar—C), 128.4 (Ar—C), 128.4 (Ar—C), 129.6 (Ar—C), 133.4 (Ar—C), 134.2 (Ar—C), 139.4 (Ar—C), 140.7 (Ar—C), 147.4 (Ar—C), 151.0 (Ar—C), 153.1 (Ar—C), 153.8 (Ar—C). HRMS cal. $C_{17}H_{11}ClN_4$ (ES+) m/z 306.06722495 [M+H]$^+$, found 306.073331.

4-((9-([1,1'-Biphenyl]-4-yl)-9H-purin-2-yl)amino)-2,6-difluorophenol (Compound No. A1-5). Purine (80.5 mg, 0.26 mmol), aniline (76.5 mg, 0.52 mmol) and TFA (49 µL, 0.52 mmol) were taken up in TFE (2.6 mL) and reacted according to General Procedure D. Purification via silica gel chromatography (19:1 DCM; MeOH) afforded the target compound as a brown solid (26.7 mg, 0.06 mmol, 25%). Rf 0.15 (19:1 DCM:MeOH); M.p. 270-271° C.; IR (cm$^{-1}$) 3073, 1603, 1512; $^1$H NMR (400 MHz, DMSO-d$_6$) 7.43 (1H, dd, J=7.4, 7.3 Hz, H-4'''), 7.48-7.61 (4H, m, H-3'''/5''', H-3'/5'), 7.76 (2H, d, J=7.6, H-3''/5''), 7.90 (2H, d, J=8.6 Hz, H-2'''/6'''), 8.04 (2H, d, J=8.6 Hz, H-2''/6''), 8.74 (1H, s, H-8), 8.98 (1H, s, H-6), 9.54 (1H, s, NH), 9.84 (1H, s, OH); $^{13}$C NMR (100 MHz, DMSO-d$_6$) 102.5 (d, $J_{CF}$=26.8 Hz, Ar—C), 124.0 (Ar—C), 127.8 (dd, $J_{CF}$=17.0, 17.0 Hz, Ar—C), 128.1 (Ar—C), 128.4 (Ar—C), 128.9 (Ar—C), 129.6 (Ar—C), 132.9 (Ar—C), 134.3 (Ar—C), 139.5 (Ar—C), 143.1 (Ar—C), 150.3 (Ar—C), 152.1 (Ar—C), 152.4 (dd, $J_{CF}$=237.9, 9.0 Hz, Ar—C), 156.8 (Ar—C). HRMS cal. $C_{23}H_{15}F_2N_5O$ (ES+) m/z 415.124465 [M+H]$^+$, found 415.129974.

Example 3. Kinase Inhibition Activity of Exemplary Compounds

LANCE (Lanthanide Chelate Excite)® Eu time-resolved fluorescence resonance energy transfer (TR-FRET) kinase assay (PerkinElmer) was performed in 384-well OptiPlates (Corning) using recombinant RSK2 kinase (CarnaBio), ULight™-phospho-40S ribosomal protein S6 (Ser235/236) peptide substrate (PerkinElmer), and ATP (Sigma) according to the supplier protocols. All reagents were prepared in kinase buffer containing 2 mM DTT, 50 mM HEPES, 1 mM EGTA, 10 mM MgCl$_2$, 0.01% Tween 20, pH 7.5. Inhibitor solutions were prepared such that the final DMSO concentration did not exceed 0.5%, which was shown to have no impact on kinase activity. RSK2 was used at a final concentration of 500 µM. ULight™-rpS6 substrate was used at a final concentration of 250 nM and ATP was administered at a final concentration of 3 µM. Assays were performed at 25° C. in a reaction mixture consisting of 2 µL serially diluted inhibitor solution, 4 µL kinase, 2 µL substrate, and 2 µL ATP. Reagents were incubated at room temperature for 1 h before the reaction was stopped through the addition of 5 µL of EDTA at a final concentration of 10 mM. After a 5 min incubation period, 5 µL of Eu anti-phospho-40S Ribosomal Protein S6 (Ser235/236) antibody (PerkinElmer) at a final concentration of 2 nM was added. The plate was read using a Biotek Synergy H1 Hybrid plate reader (Excitation=340 nm; Substrate emission=665 nm; Antibody emission=615 nm; Delay=100 µs; Integration=200 µs). Emission ratios (665 nm/615 nm) were calculated for each well and half-maximal inhibitory concentrations (IC$_{50}$) were determined for each inhibitor through non-linear regression analysis of the log dose-response curves.

Figure 4A:
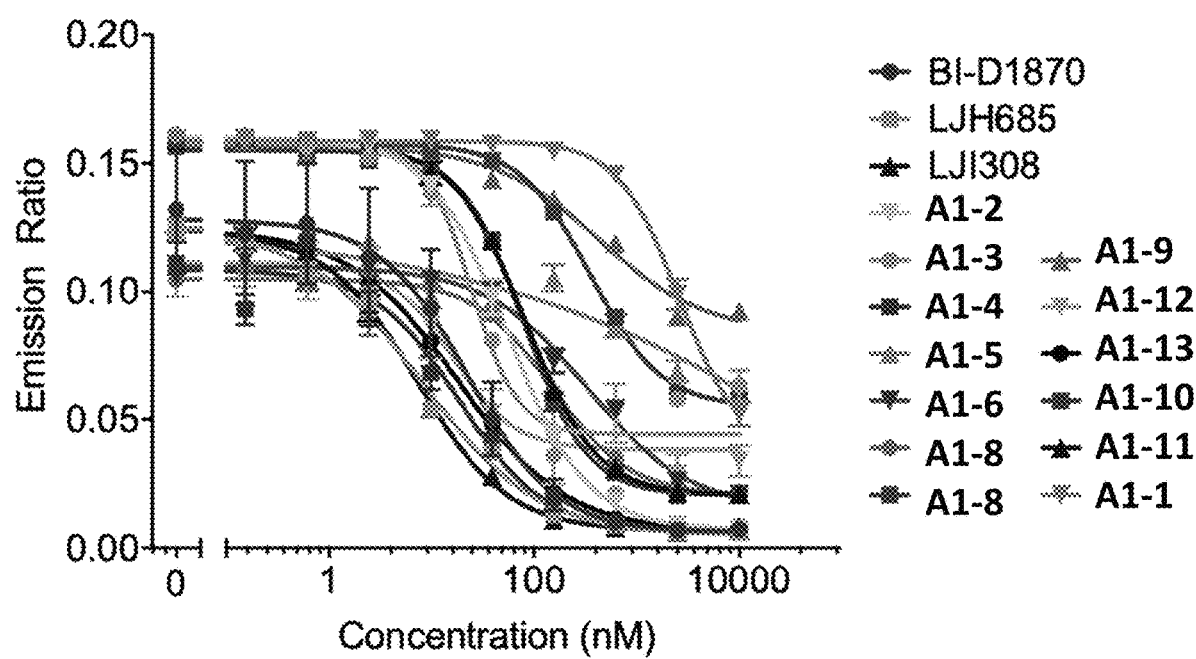
FIGS. 4A and 4B are a set of graphs showing in vitro inhibition of RSK2 as measured by TR-FRET recombinant kinase activity assay. Inhibitory $IC_{50}$ curves for (FIG. 4A) N-substituted purines and (FIG. 4B) pyrrolopyrimidines (n=3, error bars=S.E.M.).
Figure 4B:
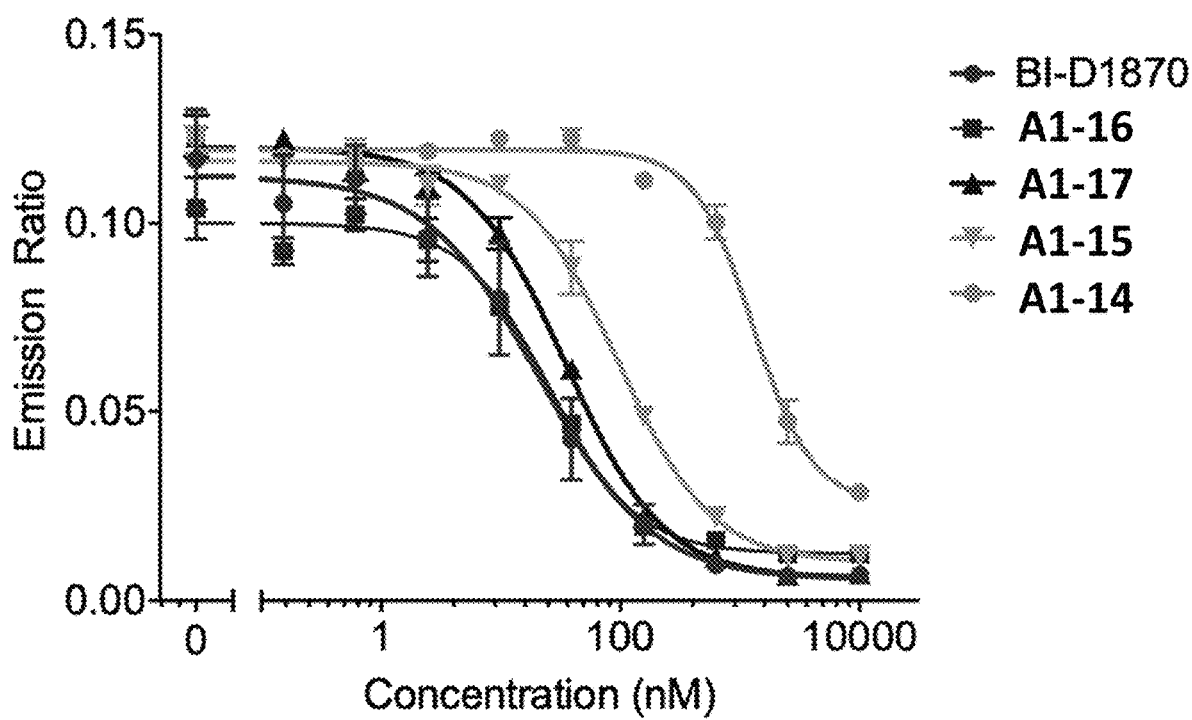

The exemplary compounds were evaluated for their effect on RSK2 activity in the recombinant TR-FRET kinase inhibition assay and their half-maximal inhibitory potency values (IC$_{50}$) were calculated using nonlinear regression analysis of the log dose-response. See Tables 1A and 1B (values are the mean± S.D. (n=3)), and FIGS. 4A and 4B.

TABLE 1A

| Compound No. | RSK2 IC$_{50}$ (nM) |
|---|---|
| BI-D1870 | 22.6 ± 6.0 |
| A1-1 | 67% @ 10 µM |
| A1-2 | 55.5 ± 5.6 |
| A1-3 | 24.6 ± 3.0 |
| A1-4 | 18.4 ± 4.0 |
| A1-5 | 49% @ 10 µM |
| A1-6 | 329 ± 37 |
| A1-7 | 148 ± 27 |
| A1-8 | 63% @ 10 µM |
| A1-9 | 42% @ 10 µM |
| A1-10 | 79.8 ± 4.6 |
| A1-11 | 81.8 ± 0.7 |
| A1-12 | 15.7 ± 4.0 |
| A1-13 | 17.8 ± 1.0 |

TABLE 1B

| Compound No. | RSK2 IC$_{50}$ (nM) |
|---|---|
| A1-14 | 77% @ 10 µM |
| A1-15 | 95.8 ± 11 |
| A1-16 | 25.7 ± 2.4 |
| A1-17 | 34.7 ± 1.3 |

Example 4. Cell Viability Effects of Exemplary Compounds

Cell Culture: MOLM-13 (DSMZ) cells were cultured in RPMI1640 (Gibco) supplemented with 10% FBS (Sigma Aldrich) and 1% penicillin/streptomycin solution (Cellgro) at 37° C. in an incubator humidifier with 95% air and 5% CO$_2$. HEK293 cells (ATCC) were cultured in Dulbecco's Modified Eagle Medium (DMEM; Gibco) supplemented with 10% FBS (Sigma Aldrich) and 1% penicillin/streptomycin solution (Cellgro) at 37° C. in an incubator humidifier with 95% air and 5% CO$_2$. HEK293 cells were allowed to adhere for 24 h prior to use in assays. In all assays, the final DMSO concentration did not exceed 0.5% for all treatment conditions.

MTS Cellular Viability Assay: MOLM-13 cells were seeded into sterile 96-well plates (Corning) at 60,000 cells per well in 100 µL of media. Inhibitor solutions were administered in 50 µL over a concentration range from 60 µM to 247 nM and cells were incubated at 37° C. for 24 to 72 h. Following 3 h incubation with 30 µL CellTiter 96® Aqueous One Cell Proliferation Reagent (Promega), cell viability was measured by formazan concentration assessment through colorimetric analysis using a BioTek Synergy H1 Hybrid plate reader (Absorption=490).

Figure 2:
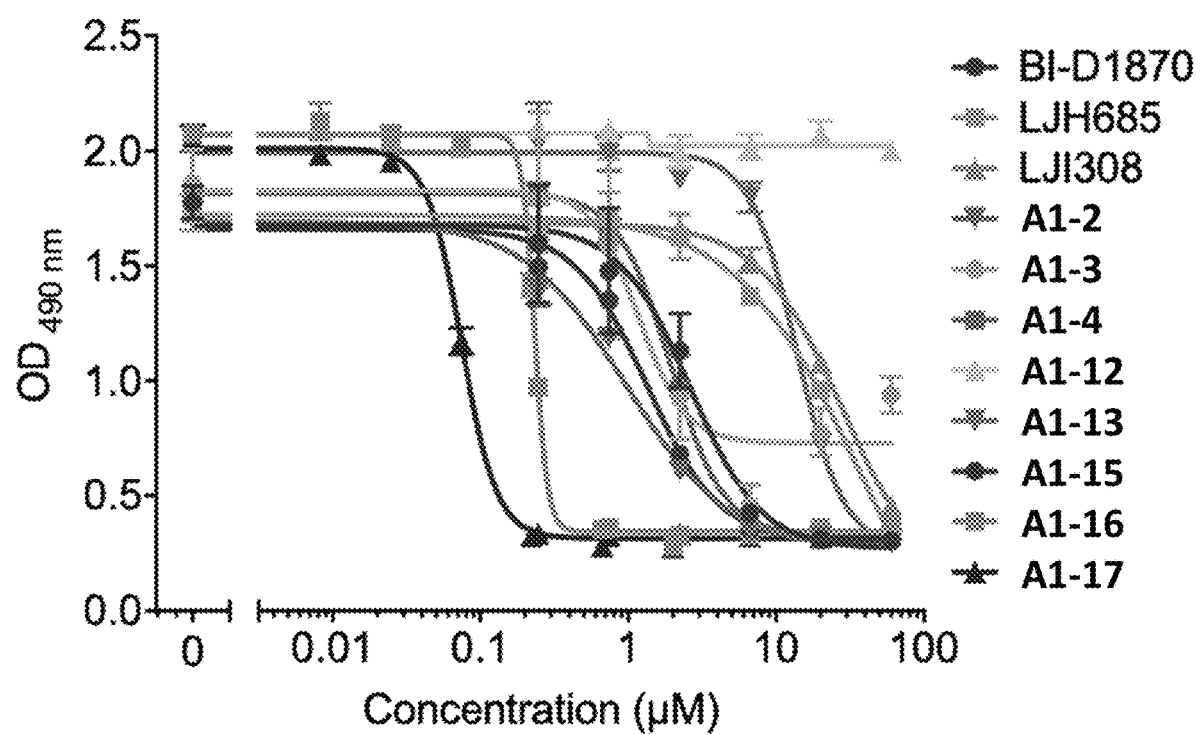
FIG. 2 is a graph showing the cellular effects of exemplary compounds on viability in MOLM-13 cells. Dose-response curves for RSK inhibitors treated over a concentration range from 60 μM to 250 nM in an MTS assay (n=3, error bars: ±S.D.).

Exemplary compounds were assessed in cell systems for effects on cell viability, as well as their ability to inhibit cellular RSK2 activity. See Table 2 (calculated $EC_{50}$ for RSK inhibitors treated over a concentration range from 60 μM to 250 nM in an MTS assay (n=3, error bars: ±S.D.)) and FIG. 2.

TABLE 2

| Compound No. | MTS 72 hr $EC_{50}$ (μM) |
| --- | --- |
| BI-D1870 | 2.60 ± 0.6 |
| LJH685 | 96% @ 60 μM |
| LJI308 | 87% @ 60 μM |
| A1-15 | 1.30 ± 0.06 |
| A1-16 | 0.23 ± 0.003 |
| A1-17 | 0.07 ± 0.003 |
| A1-2 | 0.97 ± 0.1 |
| A1-3 | 53% @ 60 μM |
| A1-4 | 1.9 ± 0.07 |
| A1-12 | 5% @ 60 μM |
| A1-13 | 13.9 ± 0.7 |

Example 5. Effects of Exemplary Compounds in Inhibition of Cellular RSK2 Activity Intracellular RSK2 Kinase Activity: The nanoBRET intracellular kinase assay was performed by Reaction Biology Corporation. HEK293 cells were cultured according to their specified protocol and transfected with NanoLuc®-RPS6KA3 fusion vector containing 1 μg RPS6KA3 fusion DNA and 9 μg transfection carrier DNA. Transfected cells were treated with supplied compounds (10 mM stock in DMSO) at a starting concentration of 100 μM using 2-fold dilutions. BRET ratios were calculated by dividing the acceptor (Acceptor=610 nm) emission by the donor (Donor=450 nm) emission, correcting for background by subtracting the 'no tracer' BRET ratio from each sample.

Figure 3A:
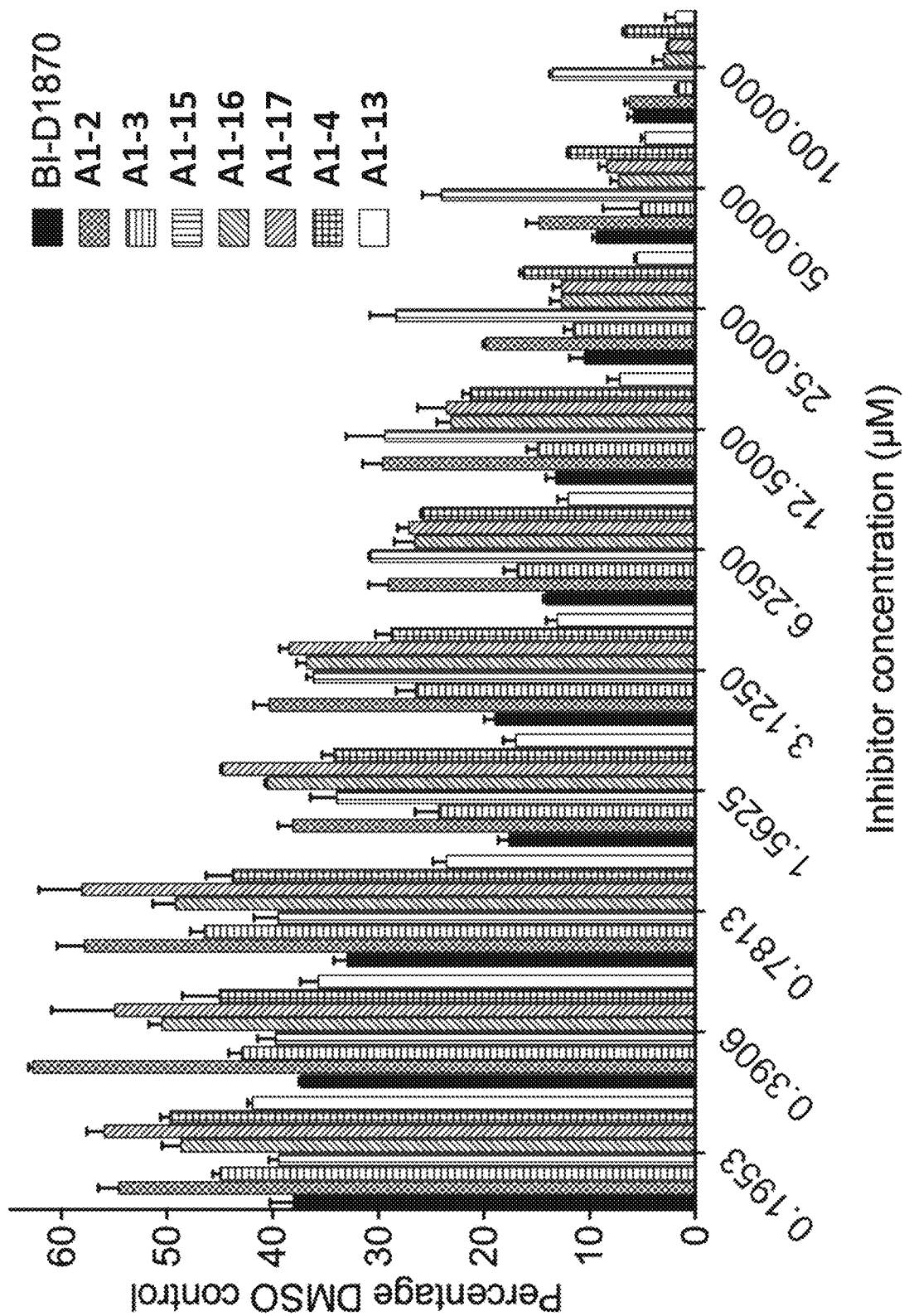
FIGS. 3A and 3B are a set of graphs showing inhibition of cellular RSK2 activity by exemplary compounds as measured by nanoBRET assay. Representative BRET ratios are compared to DMSO and reported as percentage DMSO control. Inhibitors were treated over a concentration range of 195 nM to 100 μM for 2 h (n=4, error bars: ±S.D.). For FIG. 3A, all compounds were analyzed in relation to BI-D1870. For FIG. 3B, BI-D1870, Compound No. A1-3, and Compound No. A1-13 were analyzed in multiple comparisons by two-way ANOVA, *P<0.001; **P<0.0001.
Figure 3B:
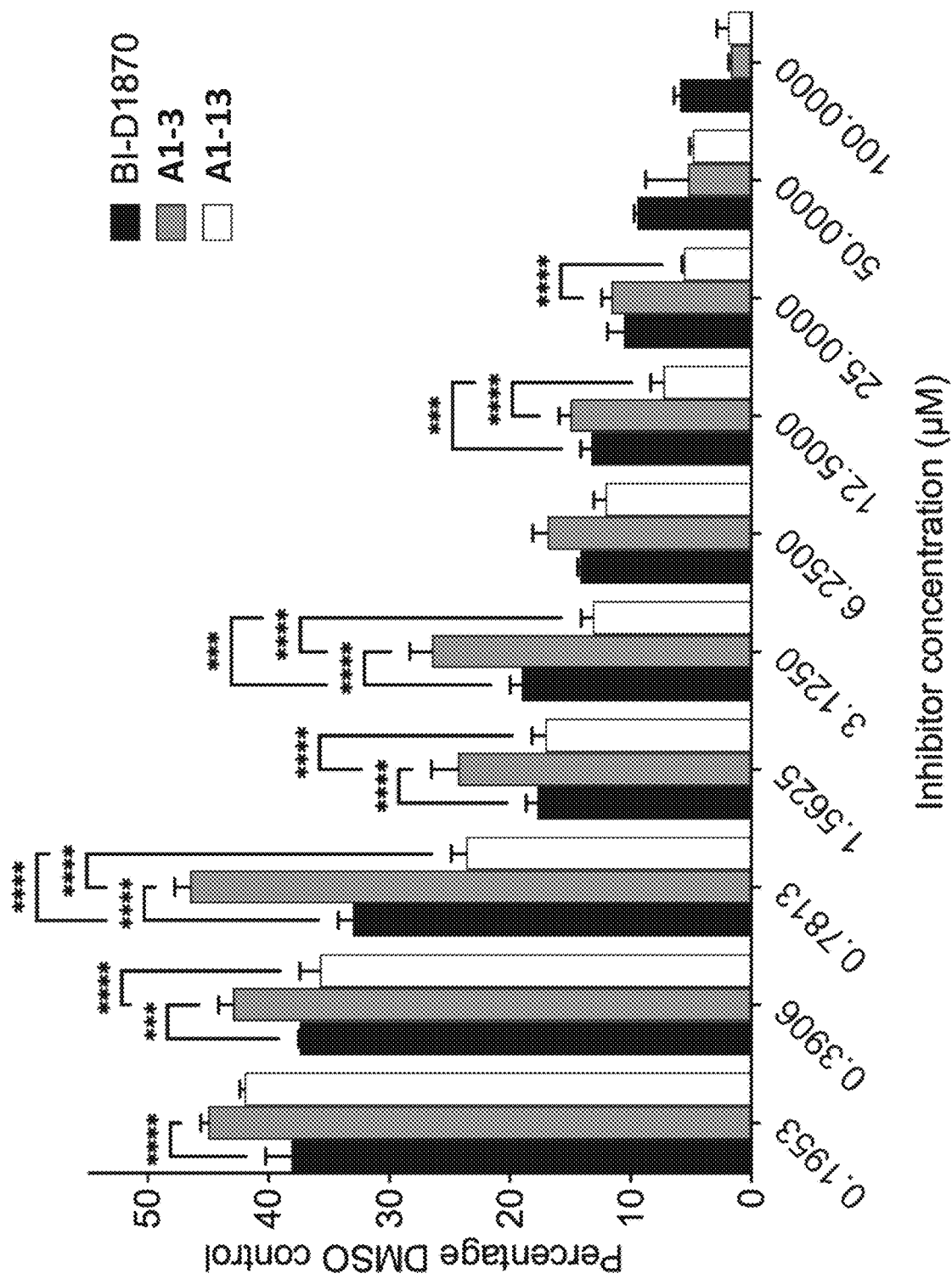

Exemplary compounds were assessed for their capacity to inhibit cellular RSK2 using the NanoBRET intracellular kinase assay. See FIGS. 3A and 3B.

EQUIVALENTS

The details of one or more embodiments of the disclosure are set forth in the accompanying description above. Although any methods and materials similar or equivalent to those described herein can be used in the practice or testing of the present disclosure, the preferred methods and materials are now described. Other features, objects, and advantages of the disclosure will be apparent from the description and from the claims. In the specification and the appended claims, the singular forms include plural referents unless the context clearly dictates otherwise. Unless defined otherwise, all technical and scientific terms used herein have the same meaning as commonly understood by one of ordinary skill in the art to which this disclosure belongs. All patents and publications cited in this specification are incorporated by reference.

The foregoing description has been presented only for the purposes of illustration and is not intended to limit the disclosure to the precise form disclosed, but by the claims appended hereto.

What is claimed is:

1. A compound of Formula (0):

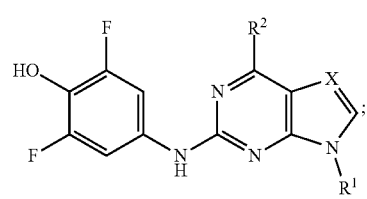

a stereoisomer thereof, a prodrug thereof, or a pharmaceutically acceptable salt thereof, wherein:

X is N or CH;

$R^1$ is H, $C_1$-$C_6$ alkyl, or $C_5$-$C_{10}$ aryl, wherein the $C_5$-$C_{10}$ aryl is substituted with one or more $R^{1a}$;

each $R^{1a}$ independently is -$T^1$-$R^{1b}$;

each $T^1$ independently is absent, —O—*, —($C_1$-$C_6$ alkyl)-*, or —O—($C_1$-$C_6$ alkyl)-*, wherein * denotes attachment to $R^{1b}$;

each $R^{1b}$ independently is —OH, —C(=O)OH, —C(=O)O—($C_1$-$C_6$ alkyl), $C_5$-$C_{10}$ aryl, or 3- to 8-membered heterocycloalkyl, wherein the $C_5$-$C_{10}$ aryl or 3- to 8-membered heterocycloalkyl is optionally substituted with one or more OH or $C_1$-$C_6$ alkyl;

$R^2$ is H or 3- to 8-membered heterocycloalkyl optionally substituted with one or more $R^{2a}$;

each $R^{2a}$ independently is —$NH_2$, —NH(C=O)O—($C_1$-$C_6$ alkyl), —C(=O)OH, or —C(=O)NH—$R^{2b}$; and each $R^{2b}$ independently is $C_1$-$C_6$ alkyl or —($C_1$-$C_6$ alkyl)-($C_5$-$C_{10}$ aryl), wherein the $C_1$-$C_6$ alkyl or —($C_1$-$C_6$ alkyl)-($C_5$-$C_{10}$ aryl) is optionally substituted with one or more halogen or OH.

2. The compound of claim 1, being of Formula (I):

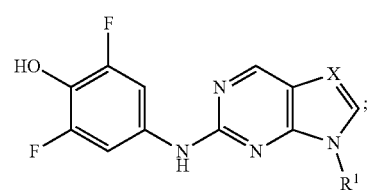

a stereoisomer thereof, a prodrug thereof, or a pharmaceutically acceptable salt thereof, wherein:

X is N or CH;

$R^1$ is H, $C_1$-$C_6$ alkyl, or $C_5$-$C_{10}$ aryl, wherein the $C_5$-$C_{10}$ aryl is substituted with one or more $R^{1a}$;

each $R^{1a}$ independently is -$T^1$-$R^{1b}$;

each $T^1$ independently is absent, —O—*, —($C_1$-$C_6$ alkyl)-*, or —O—($C_1$-$C_6$ alkyl)-*, wherein * denotes attachment to $R^{1b}$; and each $R^{1b}$ independently is —OH, —C(=O)OH, —C(=O)O—($C_1$-$C_6$ alkyl), $C_5$-$C_{10}$ aryl, or 3- to 8-membered heterocycloalkyl, wherein the $C_5$-$C_{10}$ aryl or 3- to 8-membered heterocycloalkyl is optionally substituted with one or more OH or $C_1$-$C_6$ alkyl.

3. The compound of claim 1, being of Formula (II):

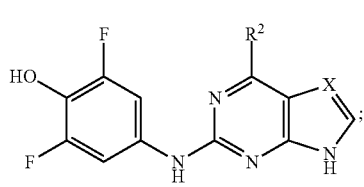

(II)

a stereoisomer thereof, a prodrug thereof, or a pharmaceutically acceptable salt thereof, wherein:

X is N or CH;

$R^2$ is H or 3- to 8-membered heterocycloalkyl optionally substituted with one or more $R^{2a}$;

each $R^{2a}$ independently is $-NH_2$, $-NH(C=O)O-(C_1-C_6$ alkyl), $-C(=O)OH$, or $-C(=O)NH-R^{2b}$; and each $R^{2b}$ independently is $C_1-C_6$ alkyl or $-(C_1-C_6$ alkyl)-$(C_5-C_{10}$ aryl), wherein the $C_1-C_6$ alkyl or $-(C_1-C_6$ alkyl)-$(C_5-C_{10}$ aryl) is optionally substituted with one or more halogen or OH.

4. The compound of claim 1, wherein X is N.

5. The compound of claim 1, wherein X is CH.

6. The compound of claim 1, wherein $R^1$ is $C_1-C_6$ alkyl.

7. The compound of claim 1, wherein $R^1$ is phenyl substituted with one or more $R^{1a}$.

8. The compound of claim 1, wherein at least one $R^{1b}$ is $-OH$, $-C(=O)OH$, or $-C(=O)O-(C_1-C_6$ alkyl).

9. The compound of claim 1, wherein at least one $R^{1b}$ is $C_5-C_{10}$ aryl or 3- to 8-membered heterocycloalkyl, wherein the $C_5-C_{10}$ aryl or 3- to 8-membered heterocycloalkyl is optionally substituted with one or more OH or $C_1-C_6$ alkyl.

10. The compound of claim 1, wherein $R^2$ is

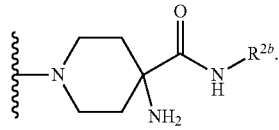

11. The compound of claim 1, wherein at least one $R^{2b}$ is $-(C_1-C_6$ alkyl)-$(C_5-C_{10}$ aryl) optionally substituted with one or more halogen or OH.

12. The compound of claim 1, wherein at least one $R^{2b}$ is

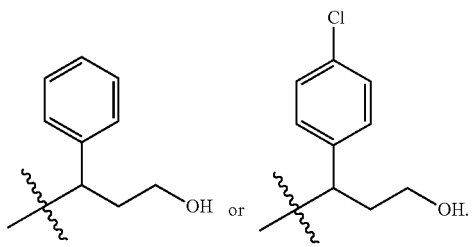 [SMILES: *C(CCO)c1ccccc1 ; *C(CCO)c1ccc(Cl)cc1 ; "or"]

13. The compound of claim 1, wherein $R^2$ is

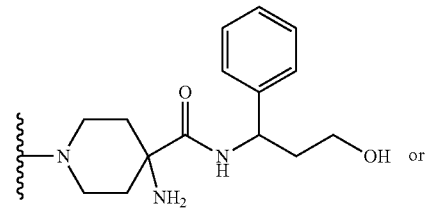

or

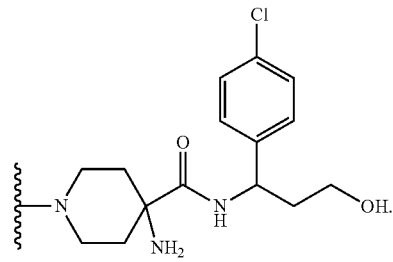

14. A compound selected from:

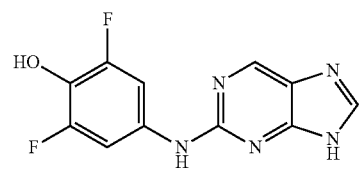

A1-1

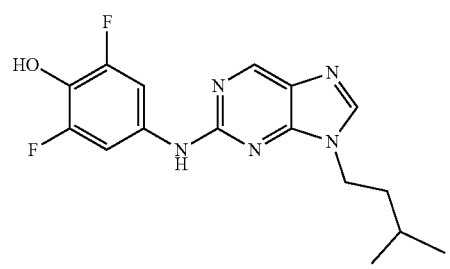

A1-2

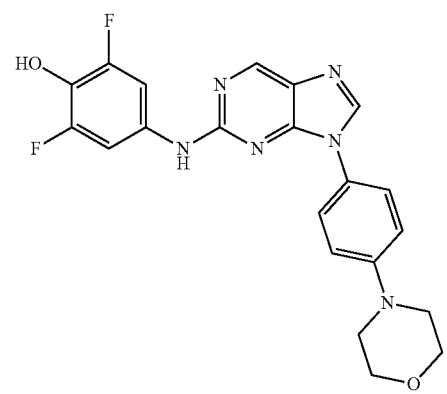

A1-3

A1-4
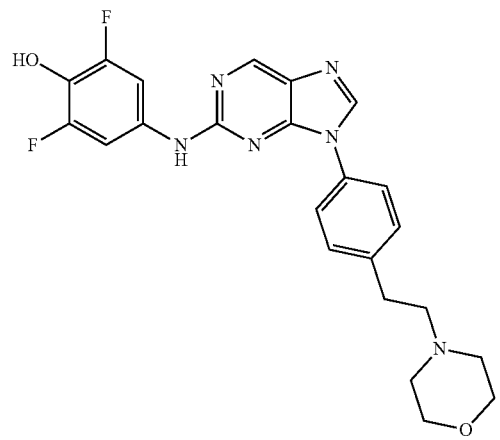
A1-5
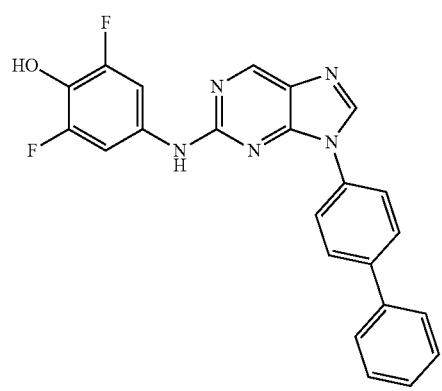
A1-6
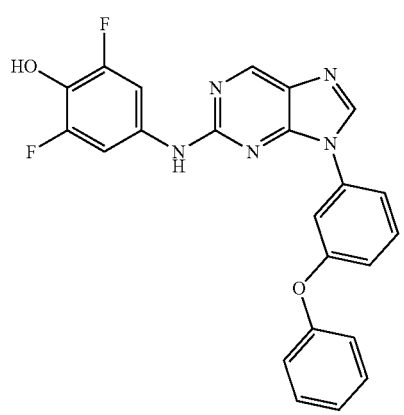
A1-7
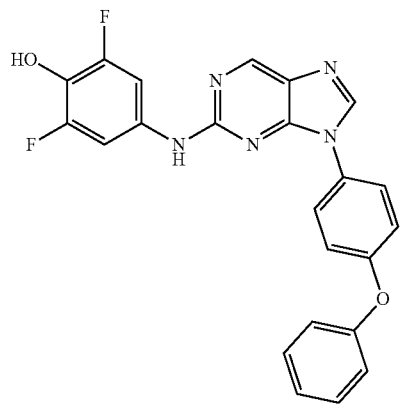
A1-8
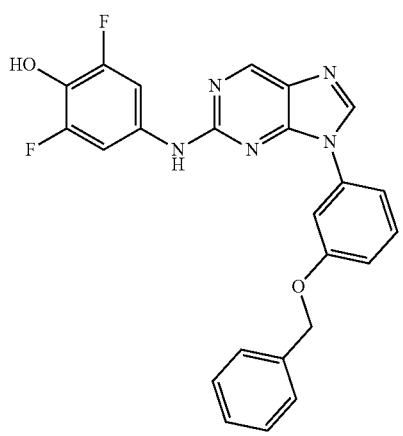
A1-9
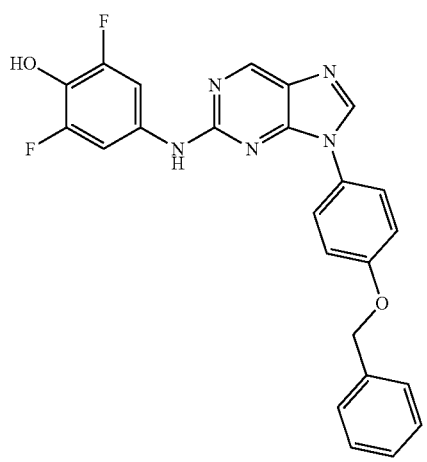
A1-10
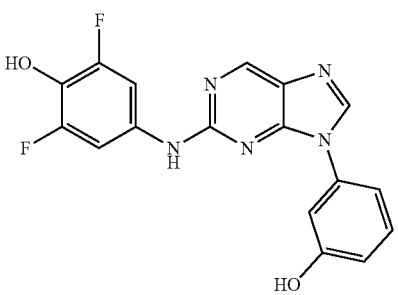
A1-11
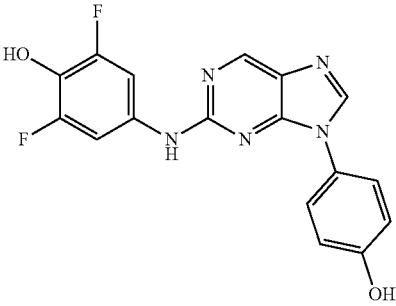

A1-12
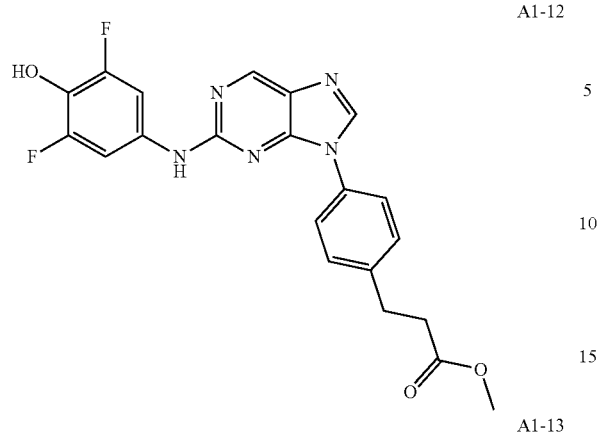
A1-13
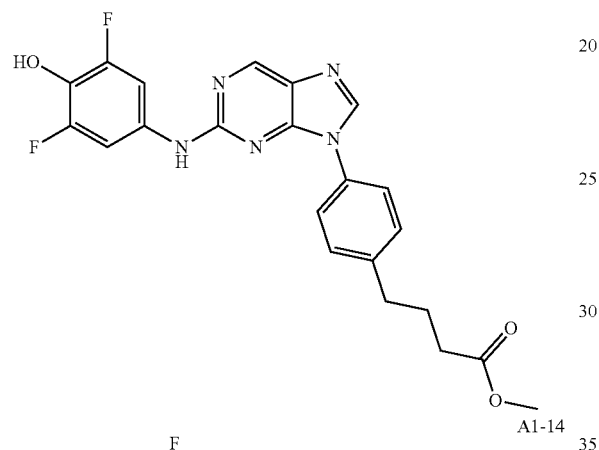
A1-14
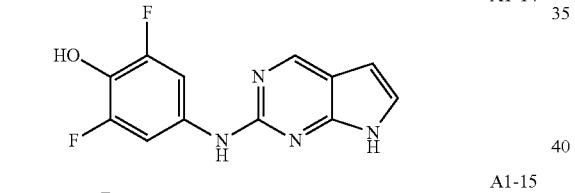
A1-15
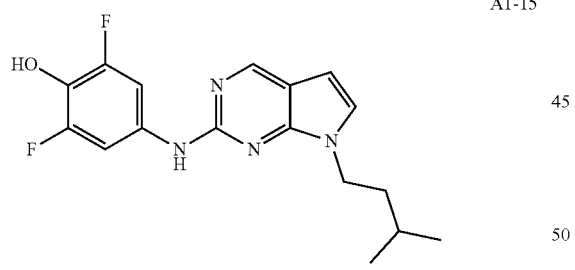
A1-16
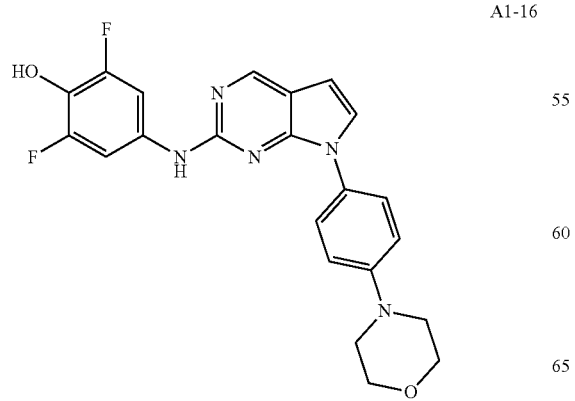
A1-17
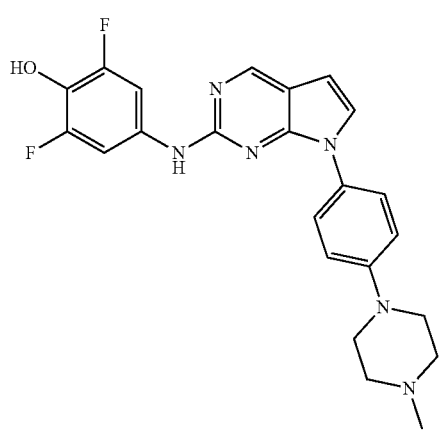
A2-1
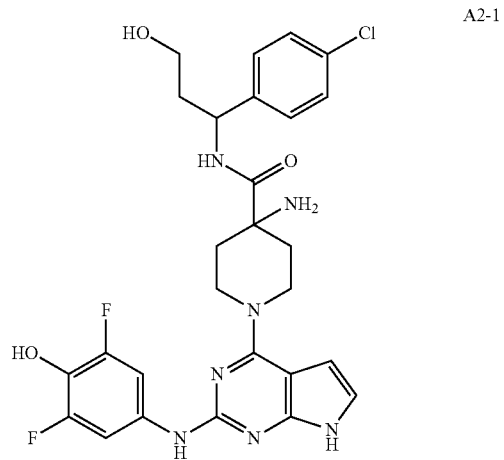
A2-2
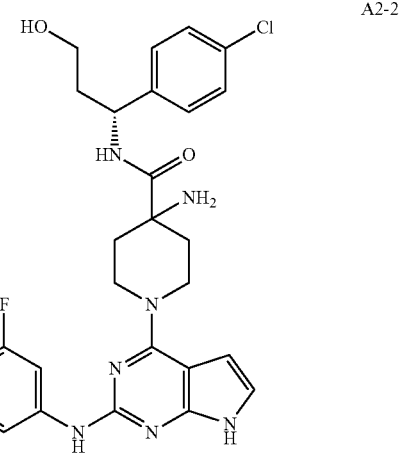

-continued

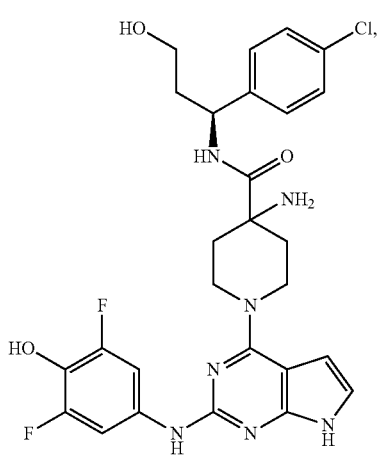

A2-3 stereoisomers thereof, prodrugs thereof, and pharmaceutically acceptable salts thereof.

15. A compound being an isotopic derivative of the compound of claim 1.

16. A pharmaceutical composition comprising the compound of claim 1, and one or more pharmaceutically acceptable carriers or excipients.

17. A method for modulating RSK activity in a subject, the method comprising administering to the subject a therapeutically effective amount of the compound of claim 1.

18. A method of treating or preventing cancer in a subject, the method comprising administering to the subject a therapeutically effective amount of the compound of claim 1, wherein said cancer is selected from the group consisting of breast cancer, colorectal cancer, head and neck squamous cell carcinoma (HNSCC), leukemia, lung, cancer, malignant melanoma, multiple myeloma, acute myeloid leukemia (AML), ovarian carcinoma, and prostate cancer.

* * * * *